United States Patent [19]
Lee et al.

[11] Patent Number: 5,807,996
[45] Date of Patent: Sep. 15, 1998

[54] FUSED POLYPEPTIDES COMPRISING INTERLEUKIN-4 POLYPEPTIDE FRAGMENTS

[75] Inventors: Frank Lee; Takashi Yokota; Ken-ichi Arai, all of Palo Alto; Timothy Mosmann, Atherton; Donna Rennick, Los Altos, all of Calif.

[73] Assignee: Schering Corporation, Kenilworth, N.J.

[21] Appl. No.: 468,735

[22] Filed: Jun. 6, 1995

Related U.S. Application Data

[62] Division of Ser. No. 221,551, Apr. 1, 1994, abandoned, which is a continuation of Ser. No. 27,601, Mar. 5, 1993, abandoned, which is a continuation-in-part of Ser. No. 854,771, Mar. 20, 1992, abandoned, which is a continuation of Ser. No. 615,902, Nov. 20, 1990, abandoned, which is a division of Ser. No. 908,215, Sep. 17, 1986, Pat. No. 5,017,691, which is a continuation-in-part of Ser. No. 881,553, Jul. 3, 1986, abandoned, which is a continuation-in-part of Ser. No. 843,958, Mar. 25, 1986, Pat. No. 5,552,304, which is a continuation-in-part of Ser. No. 799,668, Nov. 19, 1985, abandoned.

[51] Int. Cl.$^6$ .......................... C07K 14/54; C07K 14/00
[52] U.S. Cl. .......................... 530/351; 530/350; 530/397; 435/69.7
[58] Field of Search .................... 530/350, 395, 530/351; 435/69.7

[56] References Cited

U.S. PATENT DOCUMENTS

| | | | |
|---|---|---|---|
| 4,411,993 | 10/1983 | Gillis | 435/68 |
| 4,518,584 | 5/1985 | Mak et al. | 424/85 |
| 4,613,459 | 9/1986 | Cantor et al. | 530/351 |
| 5,013,824 | 5/1991 | Abrams et al. | 530/300 |
| 5,017,691 | 5/1991 | Lee et al. | 530/351 |
| 5,496,924 | 3/1996 | Habermann et al. | 530/350 |

FOREIGN PATENT DOCUMENTS

| | | |
|---|---|---|
| 0 218 431 A2 | 9/1986 | European Pat. Off. . |
| 60-232091 | 11/1985 | Japan . |
| WO 87/04723 | 1/1981 | WIPO . |

OTHER PUBLICATIONS

Daniel et al. Virology 202:540–549, 1994.
Bowie et al. Science 247:1306–1310, 1990.
Ngo et al. The Protein Folding Problem and Tertiary Structure Prediction, Merz et al, eds, Birkhauser, Boston, 1994.
Acres, et al., "Regulation of Human T–Cell Proliferation and CTL Development by Human Recombinant Interleukin–4," *Ann. N.Y. Acad. Sci.*, vol. 532, pp. 1–7, 1988.
Ambrus, et al., *J. Exp. Med.*, vol. 162, pp. 1319–1335, 1985.
Ambrus, *J. Clin. Investigations*, vol. 75, pp. 732–739, 1985a.
ATCC Catalog Excerpt, 6th Edition, p. 316, 1988.
ATCC, *ATCC Catalogue of Cell Lines & Hybridomas* (5th Ed.), p. 228, 1985.
Berman, et al., *Biotechnology*, vol. 3, pp. 51–53, 1985.
Berzofsky, *Science*, vol. 229, pp. 932–940, 1985.
Bowie, et al., Bowie, et al., *Science*, vol. 247, pp. 1306–1310, 1990.
Brandis, et al., *Genetic Engineering*, vol. 8, pp. 299–316, 1986.
Burgess, et al., *Blood*, vol. 69, pp. 43–51, 1987.
Butler, et al., "Characterization of Monoclonal B Cell Growth Factor (BCGF) Produced by Human T–T Hybridoma," *The Journal of Immunology*, vol. 133, pp. 251–255, 1984.
Butler, et al., "Development of a Human T–Cell Hybridoma Secreting Separate B–Cell Growth and Differentiation Factors," *Proc. Natl. Acad. Sci. USA*, vol. 81, pp. 2475–2478, Apr. 1984.
Cantrell, et al., *Proc. Natl. Acad. Sci.*, vol. 82, pp. 6250–6254, 1985.
Clark–Lewis, et al., *J. Immunol.*, vol. 127, p. 1941, 1981.
Coffman, et al., "B Cell Stimulatory Factor–1 Enhances the IgE Response of Lipopolysaccharide–Activated B Cells," *J. Immunol.*, vol. 136, No. 12, pp. 4538–4541, Jun. 1986.
Dayhoff, Chapter 9, *Atlas of Protein Sequence and Structure*, vol. 5, Natl. Biomed. Res. Found., Washington, D.C., 1972.
Dayhoff, et al., Chapter 22 in *Atlas of Protein Sequence and Structure*, vol. 5, Suppl. 3, 1978.
Dexter, "From the Laboratory to the Clinic," *Nature*, vol. 321, p. 198, May 1986.
Dubois, et al., "Requirement for BSF–1 in the Induction of Antigen–Specific B Cell Proliferation by a Thymus–Dependent Antigen and Carrier–Reactive T Cell Line," *J. Immunol.*, vol. 139, No. 6, pp. 1927–1934, Sep. 1987.
Falkoff, et al., "Separate Signals for Human B Cell Proliferation and Differentiation in Response to *Staphylococcus aureus*: Evidence for . . . ," *The Journal of Immunology*, vol. 129, pp. 97–102, 1982.
Falkoff, et al., "The Effects of Interleukin 1 on Human B Cell Activation and Proliferation," *J. Immunol.*, vol. 131, No. 2, pp. 801–805, Aug. 1983.
Farrar, et al., "Biochemical and Physiochemical Characteriza–tion of Mouse B Cell Growth Factor: A Lymphokine Distinct from Interleukin–2," *The Journal of Immunology*, vol. 131, pp. 1838–1842, 1983.
Farrar, et al., "The Biochemistry, Biology, and Role of Interleukin 2 in the Induction of Cytotoxic T Cell and Antibody–Forming B Cell Responses," *Immunol. Rev.*, vol. 63, pp. 129–166, 1982.

(List continued on next page.)

*Primary Examiner*—Elizabeth C. Kemmerer
*Attorney, Agent, or Firm*—Norman C. Dulak; Immac J. Thampoe

[57] ABSTRACT

Mammalian proteins and muteins thereof, designated interleukin-4s (IL-4s), are provided which exhibit both B cell growth factor activity and T cell growth factor activity. Compounds of the invention include native human and murine IL-4s, muteins thereof, and nucleic acids which are effectively homologous to disclosed cDNAs, and/or which are capable of coding for mammalian IL-4s and their muteins.

2 Claims, 24 Drawing Sheets

OTHER PUBLICATIONS

Finkelman, et al., *Proc. Natl. Acad. Sci*, vol. 83, pp. 9675–9678, 1986.
Fraga, *Can. J. Chem.*, vol. 60, pp. 2606–2610, 1982.
Fuse, et al., *Nucleic Acids Research*, vol. 12, pp. 9323–9331, 1984.
Gillis, et al., *Immun. Rev.*, vol. 63, pp. 167–209, 1982.
Gillis, et al., *J. Immunol.*, vol. 124, pp. 1954–1962, 1980.
Grabstein, et al., "Purification to Homogeneity of B Cell Stimulating Factor: A Molecule that Stimulates Proliferation of Multiple Lymphokine–Dependent . . . ," *J. Exp. Med.*, vol. 163, pp. 1405–1414, 1986.
Grantham, *Science*, vol. 185, pp. 862–864, 1974.
Harada, et al., "BCGFII Activity on Activated B Cells of a Purified Murine T Cell–Replacing Factor (TRF) from a T Cell Hybridoma (B151K12)," *J. Immunol.*, vol. 134, No. 6, pp. 3944–3951, Jun. 1985.
Hirano, et al. *Nature*, vol. 324, pp. 73–76, 1986.
Hopp, et al., *Proc. Natl. Acad. Sci.*, vol. 78, pp. 3824–3828, 1981.
Howard, et al., "B Cell Growth and Differentiation Factors," *Immunol. Rev.*, No. 78, pp. 185–210, 1984.
Howard, et al., "Identification of a T Cell–Derived B Cell Growth Factor Distinct from Interleukin 2," *J. Exp. Med.*, vol. 155, pp. 914–923, 1982.
Howard, et al., "Regulation of B–Cell Growth and Differentiation by Soluble Factors," *Ann. Rev. Immunol.*, vol. 1, pp. 307–333, 1983.
Hudak, et al., "Murine B–Cell Stimulatory Factor 1 (Interluekin 4) Increases Expression of the Fc Receptor for IgE on Mouse B Cells," *Proc. Natl. Acad. Sci. USA*, vol. 84, pp. 4606–4610, Jul. 1987.
Hunt, et al., *Atlas of Protein Sequence and Structure*, pp. 67–82, 1972.
Ihle, et al., *J. Immunol.*, vol. 129, pp. 2431–2436, 1982.
Jaenisch, *Science*, vol. 240, pp. 1468–1474, 1988.
Kashima, et al., *Nature*, vol. 312, pp. 402–404, 1985.
Kehrl, et al., "Human B Cell Activation, Proliferation and Differentiation," *Immunol. Rev.*, No., 78, pp. 75–96, 1984.
Kishimoto, "Factors Affecting B–Cell Growth and Differentiation," *Ann. Rev. Immunol.*, vol. 3, pp. 133–157, 1985.
Kishimoto, et al., "B Cell Growth and Differentiation Factors and Mechanism of B Cell Activation," *Immunol. Rev.*, No. 78, pp. 97–118, 1984.
Kornfeld, et al., *Ann. Rev. Biochem.*, vol. 45, pp. 217–237, 1976.
Kriegler, et al., *Exp. Hematol.*, vol. 12, pp. 844–849, 1984.
Lee, et al., "Isolation and Characterization of a Mouse Interleukin cDNA Clone That Expresses B–cell Stimulatory Factor 1 Activities and T–cell–and Mast–cell–stimulating Activities," *Proc. Natl. Acad. Sci. USA*, vol. 83, pp. 2061–2065, Apr. 1986.
Lee, et al., "Molecular Cloning of a Mouse T Cell Lymphokine with T Cell, B Cell and Mast Cell Stimulatory Activities," *Immune Regulation by Characterized Polypeptides*, Alan R. Less, Inc., pp. 397–405, 1987.
Lee, et al., *Proc. Natl. Acad. Sci.*, vol. 82, p. 4360, 1985.
Lerner, et al., *Proc. Natl. Acad. Sci.*, vol. 78, pp. 3404–3407, 1981.
Lewontin, *The Genetic Basis of Evolutionary Change*, Chapter 3.
Maizel, et al., "Long–Term Growth of Human B Cells and Their Use in a Microassay for B–Cell Growth Factor," *Proc. Natl. Acad. Sci. U.S.A.*, vol. 80, pp. 5047–5051, 1983.
Martens, et al., *Proc. Natl. Acad. Sci.*, vol. 84, pp. 809–813, 1987.
Marx, *Science*, vol. 226, pp. 819–821, 1984.
Mehta, et al., "Purification of Human B Cell Growth Factor," *The Journal of Immunology*, vol. 135, pp. 3298–3302, 1985.
Metcalf, *The Hematopoietic Colony Stimulating Factors*, Elseveir, Amsterdam, 1984.
Milanese et al., "Identification of T Helper Cell–Derived Lymphokine that Activates Resting T Lymphocytes," *Science*, vol. 231, pp. 1118–1122, 1986.
Minty et al., "Interleukin–13 Is a New Human Lymphokine Regulating Inflammatory and Immune Responses," *Nature*, vol. 362, pp. 248–250, Mar. 1993.
Mond, et al., "Affinity–Purified Interleukin 2 Induces Proliferation of Large but Not Small B Cells," *Proc. Natl. Acad. Sci. USA*, vol. 82, pp. 1518–1521, Mar. 1985.
Morrissey, et al., "Granulocyte–Macrophage Colony–Stimulating Factor Augments the Primary Antibody Response by Enhancing the Function of Antigen–Presenting Cells," *J. Immunol.*, vol. 139, No. 4, pp. 1113–1119, Aug. 1987.
Mosmann, et al., "T–Cell and Mast Cell Lines Respond to B–Cell Stimulatory Factor 1," *Proc. Natl. Acad. Sci USA*, vol. 83, pp. 5654–5658, Aug. 1986.
Muraguchi, et al., "Proliferative Responses of Normal Human B Lymphocytes, Development of an Assay System for Human B Cell Growth . . . ," *The Journal of Immunology*, vol. 129, pp. 1104–1108, 1982.
Nabel, et al., "Inducer T Lymphocytes Synthesize a Factor That Stimulates Proliferation of Cloned Mast Cells," *Nature*, vol. 291, pp. 332–334, May 1981.
Nabel, et al., "Multiple Biologic Activities of a Cloned Inducer T–Cell Population," *Proc. Natl. Acad. Sci. USA*, vol. 78, No. 2, pp. 1157–1161, Feb. 1981.
Nagata, et al., *Nature*, vol. 287, pp. 401–408, 1980.
Noma, et al., *Nature*, vol. 319, pp. 640–646, 1986.
Novotny, et al., *Proc. Natl. Acad. Sci.*, vol. 83, pp. 226–230, 1986.
O'Garra, et al., "Interleukin 4 (B–Cell Growth Factor II/Eosinophil Differentiation Factor) Is a Mitogen and Differentiation Factor for Preactivated Murine B Lymphocytes," *Proc. Natl. Acad. Sci. USA*, vol. 83, pp. 5228–5232, Jul. 1986.
O'Garra, et al., *Immunol. Today*, vol. 9, pp. 45–54, 1988.
Ohara, et al., "High–Efficiency Purification ahd Chemical Characterization of B Cell Stimulatory Factor–1/Interleukin 4," *J. Immunol.*, vol. 139, No. 4, pp. 1127–1134, Aug. 1987.
Ohara, et al., "Partial Purification of Murine B Cell Stimulatory Factor (BSF–1)," *The Journal of Immunology*, vol. 135, pp. 2518–2523, 1985.
Ohara, et al., "Production of a Monoclonal Antibody to and Molecular Characterization of B–Cell Stimulatory Factor–1," *Nature*, vol. 315, pp. 333–336, 1985.
Okada, et al., "B Cell Growth Factors and B Cell Differen–tiation Factor from Human T Hybridomas," *J. Exp. Med.*, vol. 157, pp. 583–590, 1983.
Oliver, et al., "B–Cell Growth Factor (B–Cell Growth Factor I or B–Cell–Stimulating Factor, Provisional 1) is a Diff. Factor for Resting B Cells . . . ," *Proc. Natl. Acad. Sci. U.S.A.*, vol. 82, pp. 2465–2467, 1985.
Otsuka, et al., "Structural Analysis of the Mouse Chromosomal Gene Encoding Interleukin 4 Which Expresses B Cell, T Cell and Mast Cell Stimulating Activities," *Nucleic Acids Research*, vol. 15, No. 1, pp. 333–344, 1987.

Palfreyman, et al., *J. Immunol. Meth.*, vol. 75, pp. 383–393, 1984.

Paul, "Nomenclature of Lymphokines Which Regulate B–Lymphocytes," *Molecular Immunology*, vol. 21, No. 4, p. 343, 1984.

Paul, "Proposed Nomenclature for B–Cell Stimulating Factors," *Immunology Today*, vol. 4, No. 12, p. 332, 1983.

Puré, et al., "Induction of B Cell Differentiation by T Cell Factors," *J. Immunol.*, vol. 127, No. 5. pp. 1953–1958, Nov. 1981.

Rabin, et al., "B–Cell Stimulatory Factor 1 Activates Resting B Cells," *Proc. Natl. Acad. Sci. U.S.A.*, vol. 82, pp. 2935–2939, 1985.

Rennick, et al., *J. Immunol.*, vol. 134, pp. 910–919, 1985.

Robson, et al., *Introduction to Proteins and Protein Engineering*, pp. 323–327, 1988.

Roehm, et al., "Interleukin–Induced Increase in Ia Expression by Normal Mouse B Cells," *J. Exp. Med.*, vol. 160, pp. 679–694, Sep. 1984.

Roitsch, et al., *Immunol. Meth.*, vol. 3, pp. 85–109, 1985.

Rosenberg, et al., "A New Approach to the Adoptive Immunotherapy of Cancer with Tumor–Infiltrating Lymphocytes," *Sciences*, vol. 233, pp. 1318–1321, Sep. 1986.

Rosenberg, et al., "Cancer Immunotherapy Using Interleukin–2 and Interleukin–2–Activated Lymphocytes," *Ann. Rev. Immunol.*, vol. 4, pp. 681–709, 1986.

Sahasrabuddhe, et al., "Purification and Partial Character–ization of Human Intracellular B Cell Growth Factor," *Lymphokine Research*, vol. 5, pp. 127–140, 1986.

Sanderson, et al., "Eosinophil Differentiation Factor Also has B–Cell Growth Factor Activity: Proposed Name Interleukin–4," *Proc. Natl. Acad. Sci. U.S.A*, vol. 83, pp. 437–440, 1986.

Sensabaugh, *Isozymes*, vol. 11, pp. 137–154, 1983.

Sharma et al., "ISCU Short Rep. 2," *Adv. Gene Technol.*, pp. 295–296, 1985.

Sharma et al., *Science*, vol. 235, pp., 1489–1492, 1987.

Sharon et al., *Chemical & Engineering News*, pp. 21–44, Mar. 30, 1981.

Sideras, et al., "Partial Biochemical Characterization of $IgG_1$–inducing Factor," *Eur. J. Immunol.*, vol. 15, pp. 593–598, 1985.

Sideras, et al., "Secretion of $IgG_1$ Induction Factor by T Cell Clones on Hybridomas," *Eur. J. Immunol.*, vol. 15, pp. 586–593, 1985.

Smith, et al., "Characterization of a Murine Lymphokine Distinct from Interleukin 2 and Interleukin 3 (IL–3) Possessing a T–cell Growth Factor Activity and a Mast–cell Growth Factor Activity That Synergizes with IL–3," *Proc. Natl. Acad. Sci. USA*, vol. 83, pp. 1857–1861, Mar. 1986.

Spits, et al., "IL–4 Inhibits IL–2–Mediated Induction of Human Lymphokine–Activated Killer Cells, but Not the Generation of Antigen–Specific Cytotoxic T Lymphocytes in Mixed Leukocyte Cultures," *J. Immunol.*, vol. 141, No. 1, pp. 29–36, Jul. 1988.

Spits, et al., "Recombinant Interleukin 4 Promotes the Growth of Human T Cells," *J. Immunol.*, vol. 139, No. 4, pp. 1142–1147, Aug. 1987.

Stanley, *Trends in Genetics*, vol. 3, pp. 77–81, 1987.

Swain, et al., "Evidence for Two Distinct Classes of Murine B Cell Growth Factors with Activities in Different Functional Assays," *J. Exp. Med.*, vol. 158, pp. 822–835, 1983.

Taniguchi, et al., *Nature*, vol. 302, pp. 305–310, 1983.

Thompson, et al., "T Cell–Derived B Cell Growth Factor(s) Can Induce Stimulation of Both Resting and Acivated B Cells," *The Journal of Immunology*, vol. 134, pp. 369–374, 1985.

Ullrich, et al., *Nature*, vol. 303, pp. 821–825, 1983.

Vitetta, et al., *J. Exp. Med.*, vol. 162, pp. 1726–1731, 1985.

Vogel, et al., *Human Genetics*, pp. 373–378.

Walter, et al., *Genetic Engineering*, vol. 5, pp. 61–91, 1983.

Weatherall, et al., *Cell*, vol. 16, pp. 467–479, 1979.

Westhof, et al., *Nature*, vol. 371, pp. 123–125, 1984.

Wong, et al., *Science*, vol. 228, pp. 810–815, 1985.

Yodoi, et al., "T Cell Hybridomas Coexpressing Fc Receptors (FcR) for Different Isotypes," *J. Immunol.*, vol. 131, No. 1, pp. 303–310, Jul. 1983.

Yokota, et al., "Isolation and Characterization of a Human Interleukin cDNA Clone, Homologous to Mouse B–cell Stimulatory Factor 1, That expresses B–cell–and T–cell–stimulating Activities," *Proc. Natl. Acad. Sci. USA*, vol. 83, pp. 5894–5898, Aug. 1986.

Yoshizaki, et al., "Characterization of Human B Cell Growth Factor (BCGF) from Cloned T Cells of Mitogen–Stimulated T Cells," *The Journal of Immunology*, vol. 130, pp. 1241–1246, 1983.

Yoshizaki, et al., *J. Immunol.*, vol. 128, pp. 1296–1301, 1982.

Yung, et al., *Contemp. Top. Mol. Immunol.*, vol. 10, pp. 147–179, 1985.

Yung, et al., *J. Immunol.*, vol. 127, p. 794, 1981.

Zlotnik, et al., "Evidence for Effects of Interleukin 4 (B Cell Stimulatory Factor 1) on Macrophages: Ehancement of Antigen Presenting Ability of Bone Marrow–Derived Macrophages," *J. Immunol.*, vol. 138, No. 12, pp. 4275–4279, Jun. 1987.

Zlotnik, et al., "Interleukin 4 Is a Growth Factor for Activated Thymocytes: Possible Role in T–Cell Ontogeny," *Proc. Natl. Acad. Sci. USA*, vol. 84, pp. 3856–3860, Jun. 1987.

Zurawski, et al. *EMBO J.*, vol. 7, pp. 1061–1069, 1988.

Daniel et al. Virology 202:504–549, 1994.

```
               10         20         30         40         50
TTAGCATCTC TTGATAAACT TAATTGTCTC TCGTCACTGA CGCACAGAGC TATTG ATG GGT CTC
                                                             MET Gly Leu 70                 85                 100                115
AAC CCC CAG CTA GTT GTC ATC CTG CTC TTC TTT CTC GAA TGT ACC AGG AGC CAT
Asn Pro Gln Leu Val Val Ile Leu Leu Phe Phe Leu Glu Cys Thr Arg Ser His 130                 145                 160
ATC CAC GGA TGC GAC AAA AAT CAC TTG AGA GAG ATC ATC GGC ATT TTG AAC GAG
Ile His Gly Cys Asp Lys Asn His Leu Arg Glu Ile Ile Gly Ile Leu Asn Glu 175                 190                 205                 220
GTC ACA GGA GAA GGG ACG CCA TGC ACG GAG ATG GAT GTG CCA AAC GTC CTC ACA
Val Thr Gly Glu Gly Thr Pro Cys Thr Glu MET Asp Val Pro Asn Val Leu Thr 235                 250                 265                 280
GCA ACG AAG AAC ACC ACA GAG AGT GAG CTC GTC TGT AGG GCT TCC AAG GTG CTT
Ala Thr Lys Asn Thr Thr Glu Ser Glu Leu Val Cys Arg Ala Ser Lys Val Leu 295                 310                 325
CGT ATA TTT TAT TTA AAA CAT GGG AAA ACT CCA TGC TTG AAG AAG AAC TCT AGT
Arg Ile Phe Phe Leu Lys His Gly Lys Thr Pro Cys Leu Lys Lys Asn Ser Ser 340                 355                 370                 385
GTT CTC ATG GAG CTG CAG AGA CTC TTT CGG GCT TTT CGA TGC CTG GAT TCA TCG
Val Leu MET Glu Leu Gln Arg Leu Phe Arg Ala Phe Arg Cys Leu Asp Ser Ser 400                 415                 430
ATA AGC TGC ACC ATG AAT GAG TCC AAG TCC ACA TCA CTG AAA GAC TTC CTG GAA
Ile Ser Cys Thr MET Asn Glu Ser Lys Ser Thr Ser Leu Lys Asp Phe Leu Glu 445                 460                 475              488          498
AGC CTA AAG AGC ATC ATG CAA ATG GAT TAC TCG TAG  TACTGAGCCA CCATGCTTTA
Ser Leu Lys Ser Ile MET Gln MET Asp Tyr Ser 508        518        528        538        548        558
ACTTATGAAT TTTTAATGGT TTTATTTTTA ATATTTATAT ATTTATAATT CATAAAATAA 568        578
AATATTTGTA TAATGTAACA GAAAAAA
```

FIG. 1A

```
                10              20              30              40              50              60
GATCGTTAGC TTCTCCTGAT AAACTAATTG CCTCACATTG TCACTGCAAA TCGACACCTA TTA
                          78                              93                        108
ATG GGT CTC ACC TCC CAA CTG CTT CCC CCT CTG TTC TTC CTG CTA GCA TGT GCC
MET Gly Leu Thr Ser Gln Leu Leu Pro Pro Leu Phe Phe Leu Leu Ala Cys Ala
              123                        138                       153                       168
GGC AAC TTT GTC CAC GGA CAC AAG TGC GAT ATC ACC TTA CAG GAG ATC ATC AAA
Gly Asn Phe Val His Gly His Lys Cys Asp Ile Thr Leu Gln Glu Ile Ile Lys
                    183                             198                       213
ACT TTG AAC AGC CTC ACA GAG CAG AAG ACT CTG TGC ACC GAG TTG ACC GTA ACA
Thr Leu Asn Ser Leu Thr Glu Gln Lys Thr Leu Cys Thr Glu Leu Thr Val Thr
228                              243                       258                       273
GAC ATC TTT GCT GCC TCC AAG AAC ACA ACT GAG AAG GAA ACC TTC TGC AGG GCT
Asp Ile Phe Ala Ala Ser Lys Asn Thr Thr Glu Lys Glu Thr Phe Cys Arg Ala
              288                       303                       318                       333
GCG ACT GTG CTC CGG CAG TTC TAC AGC CAC CAT GAG AAG GAC ACT CGC TGC CTG
Ala Thr Val Leu Arg Gln Phe Tyr Ser His His Glu Lys Asp Thr Arg Cys Leu
                    348                       363                       378
GGT GCG ACT GCA CAG CAG TTC CAC AGG CAC AAG CAG CTG ATC CGA TTC CTG AAA
Gly Ala Thr Ala Gln Gln Phe His Arg His Lys Gln Leu Ile Arg Phe Leu Lys
393                              408                       423                       438
CGG CTC GAC AGG AAC CTC TGG GGC CTG GCG GGC TTG AAT TCC TGT CCT GTG AAG
Arg Leu Asp Arg Asn Leu Trp Gly Leu Ala Gly Leu Asn Ser Cys Pro Val Lys
              453                       468                       483
GAA GCC AAC CAG AGT ACG TTG GAA AAC TTC TTG GAA AGG CTA AAG ACG ATC ATG
Glu Ala Asn Gln Ser Thr Leu Glu Asn Phe Leu Glu Arg Leu Lys Thr Ile MET
498                       513                                535                 545              555
AGA GAG AAA TAT TCA AAG TGT TCG AGC TGA ATATTTAAT TTATGAGTTT TTGATAGCTT
Arg Glu Lys Tyr Ser Lys Cys Ser Ser
              565                 575              585              595              605              615
TATTTTTTAA GTATTTATAT ATTTATAACT CATCATAAAA TAAAGTATAT ATAGAATCTA AAA
```

FIG. 1B

His –Lys –Cys –Asp –Ile –Thr –Leu –Gln –Glu –Ile –
Ile –Lys –Thr –Leu –Asn –Ser –Leu –Thr –Glu –Gln –
Lys –Thr –Leu –Cys –Thr –Glu –Leu –Thr –Val –Thr –
Asp –Ile –Phe –Ala –Ala –Ser –Lys –Asn –Thr –Thr –
Glu –Lys –Glu –Thr –Phe –Cys –Arg –Ala –Ala –Thr –
Val –Leu –Arg –Gln –Phe –Tyr –Ser –His –His –Glu –
Lys –Asp –Thr –Arg –Cys –Leu –Gly –Ala –Thr –Ala –
Gln –Gln –Phe –His –Arg –His –Lys –Gln –Leu –Ile –
Arg –Phe –Leu –Lys –Arg –Leu –Asp –Arg –Asn –Leu –
Trp –Gly –Leu –Ala –Gly –Leu –Asn –Ser –Cys –Pro –
Val –Lys –Glu –Ala –Asn –Gln –Ser –Thr –Leu –Glu –
Asn –Phe –Leu –Glu –Arg –Leu –Lys –Thr –Ile –Met –
Arg –Glu –Lys –Tyr –Ser –Lys –Cys –Ser –Ser

FIG. 1C

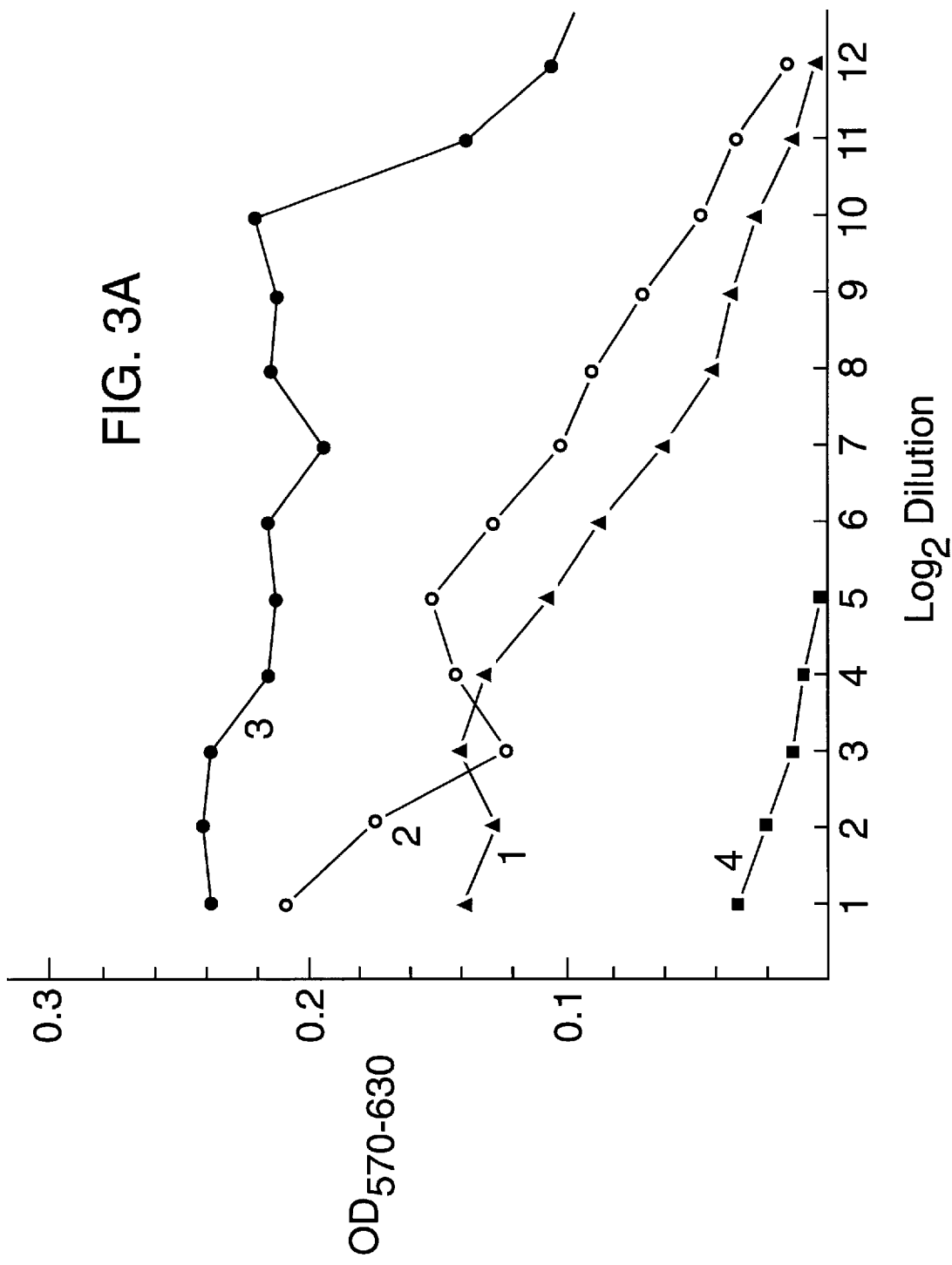

SYNTHETIC HUMAN IL-4 GENE

CAC AAA TGT GAC ATC ACT CTG CAA GAA ATC ATC AAA ACT CTG AAC

TCG TTA ACC GAA CAG AAA ACC CTG TGC ACC GAG CTC ACT GTT ACT

GAT ATC TTC GCT GCT TCC AAA AAC ACT ACT GAA AAA GAA ACT TTC

TGC AGA GCT GCT ACC GTT CTG CGT CAG TTC TAC TCT CAC CAC GAA

AAA GAC ACG CGT TGT CTC GGC GCC ACT GCG CAG CAG TTC CAC CGT

CAC AAA CAG CTG ATC AGA TTC CTG AAA CGT CTA GAC CGT AAC CTG

TGG GGC CTG GCC GGC CTG AAC TCT TGT CCG GTT AAA GAA GCT AAC

CAG TCG ACT CTG GAA AAC TTC CTC GAG CGT CTG AAA ACC ATC ATG

CGT GAA AAG TAC TCT AAA TGC TCT TCT

FIG. 6A

FRAGMENT 1A/B:

CAC AAA TGT GAC ATC ATC CTG CAA GAA ATC ATC AAA ACT CTG
GTG TTT ACA CTG TAG TGA GAC GTT CTT TAG TTT TGA GAC

AAC TCG TTA ACC GAA CAG AAA ACC CTG TGC ACC GAG CT
TTG AGC AAT TGG CTT GTC TTT TGG GAC ACG TGG C

FIG. 7A

FRAGMENT 2A/B:

C ACT GTT ACT GAT ATC TTC GCT GCT TCC AAA AAC ACT
TC GAG TGA CAA CTA TAG AAG CGA CGA AGG TTT TTG TGA

ACT GAA AAA GAA ACT TTC
TGA CTT TTT

FIG. 7B

FRAGMENT 3A/B:

TGC AGA GCT GCT ACC GTT GCT CGT CAG TTC TAG
CTT TGA AAG TCT CGA CGA TGG CAA GAC GCA GTC AAG ATG

TCT CAC CAC GAA GAC ACG CGT G
AGA GTG GTG CTT CTC TCC GCA GCA CCT AGG

FIG. 7C

FRAGMENT 4A/B:

```
CG CGT TGT CTC GGC GCC ACT GCG CAG CAG TTC CAC CGT CAC
   A   ACA GAG CCG CGG TGA CGC GTC GTC AAG GTG GCA GTG

AAA CAG CTG ATC AGA TTC CTG AAA CGT
TTT GTC GAC TAG TCT AAG GAC TTT GCA GAT C
```

FIG. 7D

FRAGMENT 5A/B:

```
CTA GAC AAC CGT AAC CTG TGG GGC CTG GCC GGC CTG AAC TCT TGT
        TG  GCA TTG GAC ACC CCG GAC CGG CCG GAC TTG AGA ACA

CCG GTT AAA GAA GCT CAG AAC
GGC CAA TTT CTT CGA GTC TTG AGC T
```

FIG. 7E

FRAGMENT 6A/B:

```
TCG ACT CTG GAA AAC TTC CTC GAG CGT CTG AAA ACC ATC ATG
 GA GAC CTT TTG AAG GAG CTC GCA GAC TTT TGG TAG TAC

CGT GAA AAG TAC TCT AAA TGC TCT TAA A
GCA CTT TTC ATG AGA TTT ACG AGA ATT TTC GAA
```

FIG. 7F

GAATTCTCATGTTTACAGCTTATCTCGGAGCTGCATGTGTCAGAGTTTCACCGTCATCACCGAA
|
Eco RI

ACGCGCAGGCAAGCTGTTGACAATTAATCATCGGCTCGTATAATGTGTGGAATTGTGAGCGGAT

```
                                          [RBS]                          Kpn I
                                                                          |
AACAATTTCACACAGGAAACAGGATCGTAAGGAGGTTTAAC ATG  AGC  TCG  GTA  CCC  GGG
                                                                                 |
Bam HI           Sal I              Sph I                          Sma I
  |                |                  |
 GAT  CCT  CTA  GAG  TCG  ACC  TGC  AGG  CAT  GCA  AGC  TTG  GCA
                 |                 |                         |
                Xba I             Pst I                   Hind III
```

FIG. 8

FUSED POLYPEPTIDES COMPRISING INTERLEUKIN-4 POLYPEPTIDE FRAGMENTS

This is a divisional of U.S. patent application Ser. No. 08/221,551 filed Apr. 1, 1994, now abandoned which is a continuation of Ser. No. 08/027,601, filed Mar. 5, 1993, now abandoned, which is a continuation of Ser. No. 07/854,771, filed Mar. 20, 1992, now abandoned, which is a continuation of Ser. No. 07/615,902, filed Nov. 20, 1990, now abandoned, which is a divisional of Ser. No. 06/908,215, filed Sep. 17, 1986, now U.S. Pat. No. 5,071,691, which is a continuation-in-part of Ser. No. 06/881,553, now abandoned, which is a continuation-in-part of Ser. No. 06/843,958 filed Mar. 25, 1986, now U.S. Pat. No. 5,552,304, which is a continuation-in-part of application Ser. No. 06/799,668, filed Nov. 19, 1985, now abandoned; all of said applications being incorporated herein by reference.

BACKGROUND OF THE INVENTION

The present invention relates generally to protein and mutein factors of the mammalian immune system and to nucleic acids coding therefor. More particularly, the invention relates to protein and mutein factors (along with their encoding nucleic acids) which exhibit both T cell growth factor activity and B cell growth factor activity.

Recombinant DNA technology refers generally to the technique of integrating genetic information from a donor source into vectors for subsequent processing, such as through introduction into a host, whereby the transferred genetic information is copied and/or expressed in the new environment. Commonly, the genetic information exists in the form of complementary DNA (cDNA) derived from messenger RNA (mRNA) coding for a desired protein product. The carrier is frequently a plasmid having the capacity to incorporate cDNA for later replication in a host and, in some cases, actually to control expression of the cDNA and thereby direct synthesis of the encoded product in the host.

For some time, it has been known that the mammalian immune response is based on a series of complex cellular interactions, called the "immune network." Recent research has provided new insights into the inner workings of this network. While it remains clear that much of the response does, in fact, revolve around the network-like interactions of lymphocytes, macrophages, granulocytes and other cells, immunologists now generally hold the opinion that soluble proteins (e.g., the so-called "lymphokines" or "monokines") play a critical role in controlling these cellular interactions. Thus, there is considerable interest in the isolation, characterization, and mechanisms of action of cell modulatory factors, an understanding of which should yield significant breakthroughs in the diagnosis and therapy of numerous disease states.

Lymphokines apparently mediate cellular activities in a variety of ways. They have been shown to support the proliferation, growth and differentiation of the pluripotential hematopoietic stem cells into the vast number of progenitors composing the diverse cellular lineages responsible for the immune response. These lineages often respond in a different manner when lymphokines are used in conjunction with other agents.

Cell lineages that are especially important to the immune response include two classes of lymphocytes: B-cells, which can produce and secrete immunoglobulins (proteins with the capability of recognizing and binding to foreign matter to effect its removal), and T-cells of various subsets that secrete lymphokines and induce or suppress the B-cells and some of the other cells (including other T-cells) making up the immune network.

Another important cell lineage is the mast cell (which has not been positively identified in all mammalian species)—a granule-containing connective tissue cell located proximal to capillaries throughout the body, with especially high concentrations in the lungs, skin, and gastrointestinal and genitourinary tracts. Mast cells play a central role in allergy-related disorders, particularly anaphylaxis as follows: when-selected antigens crosslink one class of immunoglobulins bound to receptors on the mast cell surface, the mast cell degranulates and releases the mediators (e.g., histamine, serotonin, heparin, prostaglandins, etc.) which cause allergic reactions, e.g., anaphylaxis.

Research to better understand (and thus potentially treat therapeutically) various immune disorders has been hampered by the general inability to maintain cells of the immune system in vitro. Immunologists have discovered that culturing these cells can be accomplished through the use of T-cell and other cell supernatants, which contain various growth factors, such as some of the lymphokines.

The detection, isolation and purification of these factors is extremely difficult, being frequently complicated by the complexity of the supernatants they are typically located in, the divergencies and cross-overs of activities of the various components in the mixtures, the sensitivity (or lack thereof) of the assays utilized to ascertain the factors' properties, the frequent similarity in the range of molecular weights and other characteristics of the factors, and the very low concentration of the factors in their natural setting.

As more lymphokines become available, primarily through molecular cloning, interest has heightened in finding clinical applications for them. Because of physiological similarities to hormones (e.g., soluble factors, growth mediators, action via cell receptors), potential uses of lymphokines have been analogized to the current uses of hormones, e.g. Dexter, Nature, Vol. 321, pg. 198 (1986). One hope is that the levels of lymphokines in a patient can be manipulated directly or indirectly to bring about a beneficial immune response, e.g. suppression in the case of inflammation, allergy, or tissue rejection, or stimulation or potentiation in the case of infection or malignant growth. Other potential clinical uses of lymphokines include maintaining and expanding in vitro populations of certain immune system cells of one person for eventual reintroduction into the same or another person for a beneficial effect. For example, investigations are currently underway to determine whether populations of lymphokine-activated killer T cells of a patient can be expanded outside his or her body then reinjected to bring about an enhanced antitumor response. Another potential clinical use of lymphokines, particularly colony stimulating factors, such as granulocyte-macrophage colony stimulating factor (GM-CSF), and factors which enhance their activities, is stimulating blood cell generation, for example, in pre- or post-chemotherapy or radiation therapy against tumors, in treatment of myeloid hypoplasias, or in treatment of neutrophil deficiency syndromes, Dexter, Nature, Vol. 321, pg. 198 (1986). Another area where such factors would be useful is in bone marrow transplant therapy, which is being used increasingly to treat a plastic anemia and certain leukemias.

There are two properties of lymphokines that have important consequences for such clinical applications: Individual lymphokines are frequently pleiotropic. And the biological effects of one lymphokine can usually be modulated by at least one other lymphokine, either by inhibition or by potentiation. For example, tumor necrosis factor, which synergizes with gamma-interferon, stimulates interleukin-1 (IL-1) production and can activate the phagocytic activity of neutrophils. IL-1, a protein produced by activated macrophages, mediates a wide range of biological activities, including stimulation of thymocyte proliferation via induction of interleukin-2 (IL-2) release, stimulation of B-lymphocyte maturation and proliferation, fibroblast growth factor activity and induction of acute-phase protein synthesis by hepatocytes. IL-1 has also been reported to stimulate prostaglandin and collagenase release from synovial cells, and to be identical to endogenous pyrogen, Krampschmidt, *J. Leuk. Biol.*, Vol. 36, pgs. 341–355 (1984).

Interleukin-2, formerly referred to as T-cell growth factor is a lymphokine which is produced by lectin- or antigen-activated T cells. The reported biological activities of IL-2 include stimulation of the long-term in vitro growth of activated T-cell clones, enhancement of thymocyte mitogenesis, and induction of cytotoxic T-cell reactivity and plaque-forming cell responses in cultures of nude mouse spleen cells. In addition, like interferons (IFNs), IL-2 has been shown to augment natural killer cell activity, suggesting a potential use in the treatment of neoplastic diseases, Henney et al., *Nature*, Vol, 291, pgs. 335–338 (1981). Some success has been reported in such therapy, e.g. Lotze and Rosenberg, "Treatment of Tumor Patients with Purified Human Interleukin-2," pgs. 711–719, in Sorg et al., Eds. *Cellular and Molecular Biology of Lymphokines* (Academic Press, Inc., New York, 1985); and Rosenberg and Lotze, "Cancer Immunotherapy Using Interleukin-2 and Interleukin-2 Activated Lymphocytes," *Ann. Rev. Immunol.*, Vol. 4, pgs. 681–709 (1986). However, IL-2 toxicity has limited the dosages which can be delivered to cancer patients for taking advantage of these properties, Lotze and Rosenberg, pgs. 711–719; and Welte et al., pgs. 755–759, in Sorg et al. Eds. (cited above).

Metcalf, D., *The Hematopoietic Colony Stimulating Factors*, (Elsevier, Amsterdam, 1984), provides an overview of research concerning lymphokines and various growth factors involved in the mammalian immune response. Yung, Y.-P., et al., *J. Immunol*. Vol. 127 pg. 794 (1981), describe the partial purification of the protein of approximately 35 kd exhibiting mast cell growth factor (MCGF) activity and its separation from interleukin-2 (IL-2), also known as T-cell growth factor (TCGF). Nabel, G., et al., *Nature*, Vol. 291, pg. 332 (1981) report an MCGF exhibiting a molecular weight of about 45 kd and a pI of about 6.0. Clark-Lewis, I. and Schrader, J., *J. Immunol.*, Vol. 127, pg. 1941 (1981), describe a protein having mast cell like growth factor activity that exhibits a molecular weight of about 29 kd in phosphate-buffered saline and about 23 kd in 6M guanadine hydrochloride, with a pI of between about 4–8 but of about 6–8 after neuraminidase treatment. Murine IL-2 and interleukin-3 (IL-3) have been partially characterized biochemically by Gillis, S., et al., *J. Immunol.*, Vol. 124, pgs. 1954–1962 (1980), and Ihle, J., et al., *J. Immunol.*, Vol. 129, pgs. 2431–2436 (1982), respectively, with IL-2 having an apparent molecular weight (probably as a dimer) of about 30–35 kd and IL-3 having a molecular weight of about 28 kd. Human IL-2 apparently has a molecular weight of about 15 kd and is described by Gillis, S., et al., *Immu. Rev.*, Vol. 63, pgs. 167–209 (1982). Comparison between IL-3 and MCGF activities of T-cell supernatants have been reported by Yung Y. and Moore, M., *Contemp. Top. Mol. Immunol.*, Vol. 10, pgs. 147–179 (1985), and Rennick, D., et al., *J. Immunol.*, Vol. 134, pgs. 910–919 (1985).

An extensive literature exists concerning the regulation of B-cell growth and differentiation by soluble factors, e.g. for reviews see Howard and Paul, *Ann. Rev. Immunol.*, Vol. 1, pgs. 307–333 (1983); Howard et al., *Immunol. Rev.*, 1984, No. 78, pgs. 185–210; Kishimoto et al., *Immunol. Rev.*, 1984, No. 78 pgs. 97–118; and Kishimoto, *Ann. Rev. Immunol.*, Vol. 3, pgs. 133–157 (1985). Some confusion has existed over the nomenclature used for labeling the various factors because of differences in source materials, difficulties in purification, and differences in the assays used to define their biological activities. Consensus in regard to nomenclature apparently has been reached in some cases, Paul, *Immunology Today*, Vol. 4, pg. 322 (1983); and Paul, *Molecular Immunol.*, Vol. 21, pg. 343 (1984). B-cell growth factor (BCGF) activity is characterized by a capacity to cause DNA synthesis in B cells co-stimulated by exposure to anti-IgM, or like antigens. It is believed that interleukin-1 (IL-1) is also required for BCGF activity to be manifested, at least when the assay is conducted with low densities of B cells. Alternative assays for human BCGF have been described, e.g. Maizel et al, *Proc. Natl. Acad. Sci.*, Vol. 80, pgs. 5047–5051 (1983) (support of long-term growth of human B cells in culture). The activity associated with the former assay has also been labelled B cell stimulatory factor-1 (BSF-1) activity and BCGF I, to distinguish it from similar and/or related activities. In particular, an activity designated BCGF II has been described. It is characterized by a capacity to cause DNA synthesis in mitogen stimulated B cells or in transformed B cell lines. Mitogens associated with BCGF II activity include dextran sulfate, lipopolysaccharide, and Staphylococcus extracts. BCGF I registers no response in these assays. In humans it is believed that BCGF II is a molecule having a molecular weight of about 50 kilodaltons (kD), and that it acts synergistically with BCGF I (i.e. BSF-1) in promoting B cell proliferation in an immune response, Yoshizaka et al., *J. Immunol.*, Vol. 130, pgs. 1241–1246 (1983). Howard et al., *J. Exp. Med.*, Vol. 155, pgs. 914–923 (1982) were the first to show the existence of a murine BCGF (later to be called variously BCGF I, BSF-1, or IgG$_1$ induction factor) distinct from interleukin-2. Similar observations were reported almost simultaneously for a human system by Yoshizaki et al., *J. Immunol.*, Vol. 128, pgs. 1296–1301 (1982); and later by Okada et al., *J. Exp. Med.*, Vol. 157, pgs. 583–590 (1983).

Biochemical and biological characterization of molecules exhibiting BCGF, or BSF-1, activity has progressed steadily since these initial discoveries. Maizel et al., *Proc. Natl. Acad. Sci.*, Vol. 79, pgs. 5998–6002 (1982), have reported a trypsin-sensitive human BCGF having a molecular weight of 12–13 kD and an isoelectric point (pI) of about 6.3–6.6. Farrar et al., *J. Immunol.*, vol. 131, pgs. 1838–1842 (1983) reported partial purification of a heterogeneous murine BCGF having molecular weights of 11 and 15 kD by SDS-PAGE and pIs of 6.4–8.7. Ohara and Paul, in *Nature*, Vol. 315, pgs. 333–336 (1985) describe a monoclonal antibody specific for murine BSF-1, and molecular weights for BSF-1 of 14 kD and 19–20 kD with pI of 6.7 Butler et al., *J. Immunol.*, Vol. 133, pgs. 251–255 (1984), report a human BCGF having a molecular weight of 18–20 kD and a pI of 6.3–6.6. Rubin et al., *Proc. Natl. Acad. Sci.*, vol. 82, pgs. 2935–2939 (1985) report that pre-incubation of resting B cells with BSF-1 prior to exposure to anti-IgM antibodies increases cell volume, and later speeds entry to S phase upon exposure to anti-IgM antibodies. Vitetta et al, *J. Exp. Med.*, Vol. 162, pgs. 1726–1731 (1985), describe partial purification of murine BSF-1 by reverse phase HPLC of serum free supernatants of EL-4 cells. SDS-PAGE indicated a protein of about 20–22 kD. Ohara et al., *J. Immunol.*, Vol. 135, pgs. 2518–2523 (1985) also report partial purification of murine BSF-1 by a similar procedure, and report the factor to be a protein of about 18–21.7 kD. Sideras et al., in *Eur. J. Immunol.*, Vol. 15, pgs. 586–593, and 593–598 (1985), report partial purification of a murine $IgG_1$-inducing factor, that is a BSF-1, and report the factor to be a protein of about 20 kD having pIs of 7.2–7.4 and 6.2–6.4, and Smith and Rennick, In *Proc. Natl. Acad. Sci.*, Vol. 83, pgs. 1857–1861 (1986), report the separation of a factor from IL-2 and IL-3 which exhibits T cell growth factor activity and mast cell growth factor activity. Later, Noma et al., *Nature*, Vol. 319, pgs. 640–646 (1986), cloned and sequenced a nucleic acid coding for the Sideras et al. factor, and Lee et al., *Proc. Natl. Acad. Sci.*, Vol. 83, pgs. 2061–2065 (1986) cloned and sequenced a nucleic acid coding for the Smith and Rennick factor. More recently, Grabstein et al., *J. Exp. Med.*, vol. 163, pgs. 1405–1414 (1986), report purifying and sequencing murine BSF-1.

Milanese, et al, in *Science*, Vol. 231, pgs. 1118–1122 (1986), report a lymphokine unrelated to BSF-1 which they provisionally designate IL-4A. Their IL-4A is a 10–12 kD protein secreted from helper T cells after cross linking of T3-Ti receptors. It stimulates resting lymphocytes via interaction with T11 receptors and subsequent induction of interleukin-2 (IL-2) receptors.

Sanderson et al., in *Proc. Natl. Acad. Sci.*, Vol. 83, pgs. 437–440 (1986), proposed that the name interleukin 4 be given to eosinophil differentiation factor based on evidence that it is apparently the same as B cell growth factor II.

From the foregoing it is evident that the discovery and development of new lymphokines could contribute to the development of therapies for a wide range of degenerative conditions which directly or indirectly involve the immune system and/or hematopoietic cells. In particular, the discovery and development of lymphokines which enhance or potentiate the beneficial activities of known lymphokines would be highly advantageous. For example, the dose-limiting toxicity of IL-2 in tumor therapy could be reduced by the availability of a lymphokine or cofactor with potentiating effects; or, the efficacy of bone marrow transplants could be increased by the availability of factors which potentiate the activities of the colony stimulating factors.

SUMMARY OF THE INVENTION

The present invention is directed to mammalian interleukin-4 (IL-4). It includes nucleic acids coding for polypeptides exhibiting IL-4 activity, as well as the polypeptides themselves and methods for their production. The nucleic acids of the invention are defined (1) by their homology to cloned complementary DNA (cDNA) sequences disclosed herein, and (2) by functional assays for IL-4 activity applied to the polypeptides encoded by the nucleic acids. As used herein, the term "IL-4 activity" in reference to a protein or a polypeptide means that the protein or polypeptide exhibits both B-cell growth factor (BCGF) activity and T cell growth factor (TCGF) activity. For a given mammal, IL-4 activity is determined by species specific TCGF and BCGF assays. As explained more fully below, specific embodiments of IL-4 can be further characterized by additional assays. For example, some forms of murine IL-4 exhibit mast cell growth factor (MCGF) activity; some forms of both human and murine IL-4 potentiate the TCGF activity of IL-2; some forms of both murine and human IL-4 potentiate GM-CSF stimulated proliferation in certain cell types; some forms of both human and murine IL-4 can induce Fc-epsilon receptor expression on B cells; and some forms of both human and murine IL-4 can induce the expression of major histocompatibility complex (MHC) antigens on B cells: The class II DR antigen on human B cells, and the Ia antigen on mouse B cells.

The invention is based in part on the discovery and cloning of cDNAs which are capable of expressing proteins having IL-4 activity. cDNA clones of the invention include human cDNA inserts of plasmid vectors "clone 46" (also referred to herein as pcD-2F1-13 or pcD-46) and "clone 125" (also referred to herein as pcD-125); and mouse cDNA insert of plasmid vector pcD-2A-E3. The three vectors are deposited with the American Type Culture Collection (ATCC), Rockville, Md., under ATCC accession numbers 53337, 67029, and 53330, respectively.

The invention includes nucleic acids having nucleotide sequences which are effectively homologous to the cDNA clones of the invention and which express IL-4 activity. Nucleic acids and proteins of the invention can be derived from the above mentioned cDNAs by standard techniques for mutating nucleic acid sequences. They can be prepared de novo from immune system-derived cell lines, such as T cell hybridomas, which contain or can be induced to contain messenger RNA (MRNA) sequences coding for IL-4. And they can be obtained by probing DNA or RNA extracts or libraries with probes derived from the cDNA clones of the invention.

The term "effectively homologous" as used herein means that the nucleotide sequence is capable of being detected by a hybridization probe derived from a cDNA clone of the invention. The exact numerical measure of homology necessary to detect nucleic acids coding for IL-4 activity depends on several factors including (1) the homology of the probe to non-IL-4 coding sequences associated with the target nucleic acids, (2) the stringency of the hybridization conditions, (3) whether single stranded or double stranded probes are employed, (4) whether RNA or DNA probes are employed, (5) the measures taken to reduce nonspecific binding of the probe, (6) the nature of the label used to detect the probe, (7) the fraction of guanidine and cytosine bases in the probe, (8) the distribution of mismatches between probe and target, (9) the size of the probe, and the like.

Preferably, an effectively homologous probe derived from the cDNA of the invention is at least fifty percent (50%) homologous to the sequence to be isolated. More preferably, the effectively homologous probe is at least seventy-five to eighty percent (75–80%) homologous to the sequence to be isolated. And most preferably, the effectively homologous probe is at least ninety percent (90%) homologous to the sequence to be isolated.

Homology as the term is used herein is a measure of similarity between two nucleotide (or amino acid) sequences. Homology is expressed as the fraction or percentage of matching bases (or amino acids) after two sequences (possibly of unequal length) have been aligned. The term alignment is used in the sense defined by Sankoff and Kruskal in chapter one of *Time Warps, String Edits, and Macromolecules: The Theory and Practice of Sequence Comparison* (Addison-Wesley, Reading, Mass., 1983). Roughly, two sequences are aligned by maximizing the number of matching bases (or amino acids) between the two sequences with the insertion of a minimal number of "blank" or "null" bases into either sequence to bring about the maximum overlap. Given two sequences, algorithms are available for computing their homology, e.g. Needleham and Wunsch, *J. Mol. Biol.*, Vol. 48, pgs. 443–453 (1970); and Sankoff and Kruskal (cited above) pgs. 23–29. Also, commercial services are available for performing such comparisons, e.g. Intelligenetics, Inc. (Palo Alto, Calif.).

A preferred embodiment of the invention is the set of glycosylated or unglycosylated human IL-4 proteins and muteins defined by the following formula:

Formula I

X(His)—X(Lys)—X(Cys)—X(Asp)—X(Ile)—X(Thr)—
X(Leu)—X(Gln)—X(Glu)—X(Ile)—X(Ile)—X(Lys)—
X(Thr)—X(Leu)—X(Asn)—X(Ser)—X(Leu)—X(Thr)—
X(Glu)—X(Gln)—X(Lys)—X(Thr)—X(Leu)—X(Cys)—
X(Thr)—X(Glu)—X(Leu)—X(Thr)—X(Val)—X(Thr)—
X(Asp)—X(Ile)—X(Phe)—X(Ala)—X(Ala)—X(Ser)—
X(Lys)—X(Asn)—X(Thr)—X(Thr)—X(Glu)—X(Lys)—
X(Glu)—X(Thr)—X(Phe)—X(Cys)—X(Arg)—X(Ala)—
X(Ala)—X(Thr)—X(Val)—X(Leu)—X(Arg)—X(Gln)—
X(Phe)—X(Tyr)—X(Ser)—X(His)—X(His)—X(Glu)—
X(Lys)—X(Asp)—X(Thr)—X(Arg)—X(Cys)—X(Leu)—
X(Gly)—X(Ala)—X(Thr)—X(Ala)—X(Gln)—X(Gln)—
X(Phe)—X(His)—X(Arg)—X(His)—X(Lys)—X(Gln)—
X(Leu)—X(Ile)—X(Arg)—X(Phe)—X(Leu)—X(Lys)—
X(Arg)—X(Leu)—X(Asp)—X(Arg)—X(Asn)—X(Leu)—
X(Trp)—X(Gly)—X(Leu)—X(Ala)—X(Gly)—X(Leu)—
X(Asn)—X(Ser)—X(Cys)—X(Pro)—X(Val)—X(Lys)—
X(Glu)—X(Ala)—X(Asn)—X(Gln)—X(Ser)—X(Thr)—
X(Leu)—X(Glu)—X(Asn)—X(Phe)—X(Leu)—X(Glu)—
X(Arg)—X(Leu)—X(Lys)—X(Thr)—X(Ile)—X(Met)—
X(Arg)—X(Glu)—X(Lys)—X(Tyr)—X(Ser)—X(Lys)—
X(Cys)—X(Ser)—X(Ser)

wherein the term X(Xaa) represents the group of synonymous amino acids to the amino acid Xaa. Synonymous amino acids within a group have sufficiently similar physicochemical properties that substitution between members of the group will preserve the biological function of the molecule, Grantham, *Science*, vol. 185, pgs. 862–864 (1974). It is clear that insertions and deletions of amino acids may also be made in the above-defined sequence without altering biological function, particularly if the insertions or deletions only involve a few amino acids, e.g. under ten, and do not remove or displace amino acids which are critical to a functional conformation, e.g. cysteine residues, Anfinsen, "Principles That Govern The Folding of Protein Chains", *Science*, Vol. 181, pgs. 223–230 (1973). Proteins and muteins produced by such deletions and/or insertions come within the purview of the present invention. Whenever amino acid residues of the protein of Formula I are referred to herein by number, such number or numbers are in reference to the N-terminus of the protein.

Preferably the synonymous amino acid groups are those defined in Table I. More preferably, the synonymous amino acid groups are those defined in Table II; and most preferably the synonymous amino acid groups are those defined in Table III.

TABLE I

Preferred Groups of Synonymous Amino Acids

| Amino Acid | Synonymous Group |
| --- | --- |
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Gly, Ala, Thr, Pro, Ser |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |

TABLE I-continued

Preferred Groups of Synonymous Amino Acids

| Amino Acid | Synonymous Group |
| --- | --- |
| Cys | Cys, Ser, Thr |
| His | His, Glu, Lys, Gln, Thr, Arg |
| Gln | Gln, Glu, Lys, Asn, His, Thr, Arg |
| Asn | Asn, Gln, Asp, Ser |
| Lys | Lys, Glu, Gln, His, Arg |
| Asp | Asp, Glu, Asn |
| Glu | Glu, Asp, Lys, Asn, Gln, His, Arg |
| Met | Met, Phe, Ile, Val, Leu |
| Trp | Trp |

TABLE II

More Preferred Groups of Synonymous Amino Acids

| Amino Acid | Synonymous Group |
| --- | --- |
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Lys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE III

Most Preferred Groups of Synonymous Amino Acids

| Amino Acid | Synonymous Group |
| --- | --- |
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Trp |

The invention includes the polypeptides of Formula I with amino acid substitutions (between an amino acid of the native human IL-4 and a synonymous amino acid) at a single position or at multiple positions. The term "N-fold substituted" is used to describe a subset of polypeptides defined by Formula I wherein the native amino acids have been substituted by synonymous amino acids at no more than N positions. Thus, for example, the group of 1-fold substituted polypeptides of Formula I consists of 559 polypeptides for the preferred groups of synonymous amino acids, 189 for the more preferred groups of synonymous amino acids, and 56 for the most preferred groups of synonymous amino acids. These numbers were arrived at by summing the number of amino acids of each kind in the native chain times one less than the size of the synonymous amino acid group for that amino acid. Preferably the group of human IL-4 polypeptides consists of the 10-fold substituted polypeptides of Formula I; more preferably they consist of 3-fold substituted polypeptides of Formula I; and most preferably they consist of 1-fold substituted polypeptides of Formula I, which in particular includes the native human IL-4 polypeptide whose sequence is illustrated in FIG. 1C.

Likewise, the term "N-fold inserted" in reference to the polypeptides of Formula I is used to describe a set of polypeptides wherein from 1 to N amino acids have been inserted into the sequence defined by Formula I. Preferably, the inserted amino acids are selected from the preferred groups of synonymous amino acids (Table I) of the amino acids flanking the insertion; more preferably they are selected from the more preferred groups of synonymous amino acids (Table II) of the amino acids flanking the insertion, and most preferably they are selected from the most preferred groups of synonymous amino acids (Table III) of the amino acids flanking the insertion. Thus, for example, one subgroup of the group of 1-fold inserted peptides comprises an amino acid inserted between the N-terminal X(His) and the adjacent X(Gly). The insertions defining the members of this subgroup are preferably selected from the group consisting of Pro, Ala, Gly, Thr, Ser, Gln, Glu, Arg, His, and Lys; more preferably they are selected from the group consisting of Gly, His, Gln and Arg, and most preferably they are selected from the group consisting of His and Gly. Insertions can be made between any adjacent amino acids of Formula I. Since there are 128 possible insertion locations, and since multiple insertions can be made at the same location, a 2-fold inserte peptide of Formula I gives rise to 16,384 subgroups of peptides, and the size of each subgroup depends on the sizes of the synonymous amino acid groups of the amino acids flanking the insertions.

The term "N-fold deleted" in reference to the polypeptides of Formula I is used to describe a set of peptides having from 1 to N amino acids deleted from the sequence defined by Formula I. Thus, the set of 1-fold deleted polypeptides of Formula I consists of 129 subgroups of polypeptides each 128 amino acids in length (128-mers). Each of the subgroups in turn consists of all the 128-mers defined by the preferred, more preferred, and most preferred synonymous amino acid groups.

The above preferred embodiment of the invention further includes nucleotide sequences effectively homologous to or capable of encoding the polypeptides of Formula I for the preferred, more preferred, and most preferred groups of synonymous amino acids. More preferably said nucleotide sequences are capable of encoding the polypeptides of Formula I for the preferred, more preferred, and most preferred groups of synonymous amino acids.

In particular, the invention includes native human IL-4, the amino acid sequence of which is illustrated in FIG. 1C and all nucleotide sequences capable of encoding it.

Throughout, standard abbreviations are used to designate amino acids, nucleotides, restriction endonucleases, and the like, e.g. Cohn, "Nomenclature and Symbolism of α-Amino Acids, "*Methods in Enzymology*, Vol. 106, pgs. 3–17 (1984); Wood et al. *Biochemistry: A Problems Approach,* 2nd ed. (Benjamin, Menlo Park, 1981); and Roberts, "Directory of Restriction Endonucleases", *Methods in Enzymology*, Vol. 68, pgs. 27–40 (1979).

The present invention is addressed to problems associated with the application of immunoregulatory agents to treat medical and/or veterinary disorders. In particular, it provides compounds which alone have beneficial effects, or which can act in concert with other lymphokines and immune system mediators to produce beneficial effects.

BRIEF DESCRIPTION OF THE DRAWINGS

FIG. 1A illustrates the nucleotide sequence and deduced amino acid sequence of the insert of vector pcD-2A-E3, which expresses murine IL-4.

FIG. 1B illustrates the nucleotide sequence and deduced amino acid sequence of the insert of vector pcD-125, which expresses human IL-4.

FIG. 1C illustrates the amino acid sequence of purified native human IL-4 expressed and secreted by COS 7 monkey cells transfected with pcD-125.

FIG. 3A illustrates relative TCGF activities (over a range of dilutions) of various culture supernatants including one (curve 1) from pcD-2A-E3 transfected COS 7 cells.

FIG. 6A illustrates the nucleotide sequence of a synthetic human IL-4 gene useful for expressing native or mutant IL-4s in *E. coli.*

FIGS. 7A–7F illustrate the double stranded DNA fragments 1A/B through 6A/B used to construct a synthetic human IL-4 gene.

FIG. 8 illustrates nucleotide sequences adjacent to the initiator ATG codon in the *E. coli* expression vector TAC-RBS. The sequences commence at an EcoRI restriction site and end with a HindIII site. The ribosome binding sequence (RBS) showing complementarity to the 3' end of 16S ribosomal RNA is underlined, and the ATG initiator codon is underlined.

DETAILED DESCRIPTION OF THE INVENTION

Figure 2A:
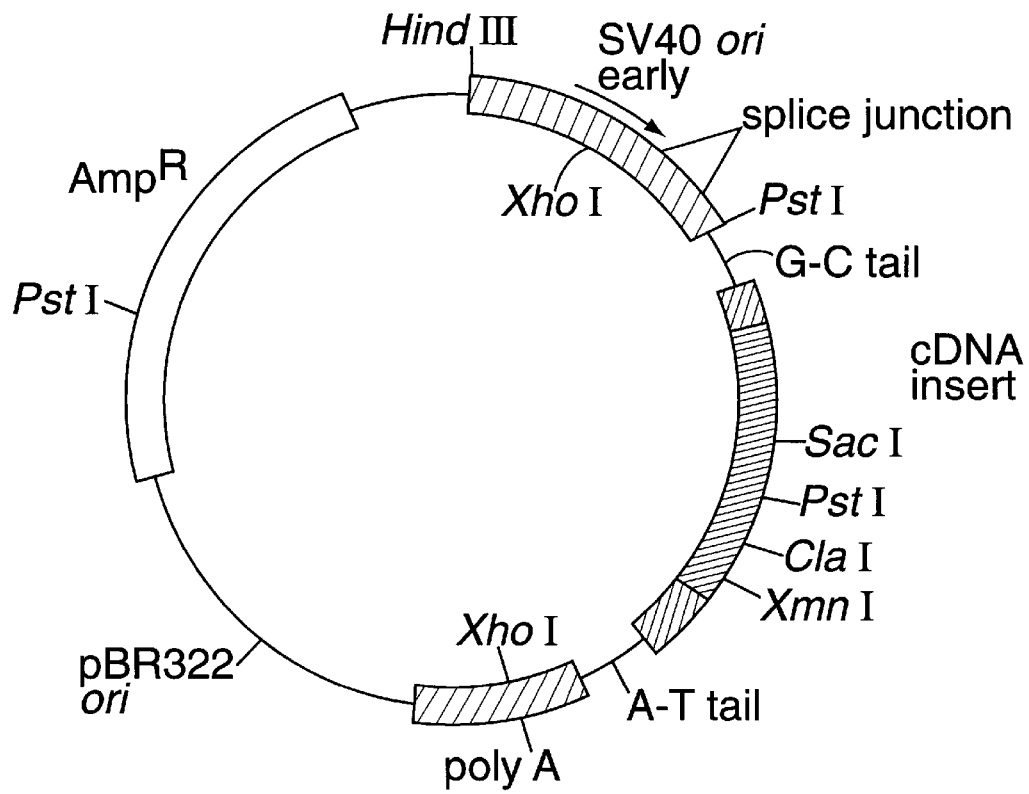
FIG. 2A is a map of vector pcD-2A-E3, the insert of which codes murine IL-4.

The present invention includes glycosylated or unglycosylated mammalian polypeptides which exhibit IL-4 activity, and which are derivable from the IL-4 polypeptides disclosed herein using standard protein engineering techniques. The invention also includes nucleic acids having sequences capable of coding for the polypeptides of the invention, and nucleic acids whose sequences are effectively homologous to the cDNA clones of the invention. Finally, the invention includes methods of making the glycosylated or unglycosylated polypeptides of the invention which utilize the nucleotides sequences disclosed herein, and methods of using the polypeptides of the invention.

Below techniques for making, using, and identifying the polypeptides and nucleic acids of the invention are discussed in general terms. Afterwards several specific examples are provided wherein the general techniques are applied using specific cell types, vectors, reagents, and the like.

I. De Novo Preparation of IL-4 cDNA

A variety of methods are now available for de novo preparation and cloning of cDNAs, and for the construction of cDNA libraries, e.g. recent reviews are given by Doherty, "Cloning and Expression of cDNA", Chapter 10 in Gottesman, Ed. *Molecular Cell Genetics* (John Wiley & Sons, New York, 1985); and Brandis et al., "Preparation of cDNA Libraries and the Detection of Specific Gene Sequences", in Setlow et al., Eds. *Genetic Engineering*, Vol. 8, pgs. 299–316 (Plenum Press, New York, 1986).

By way of example, total MRNA is extracted (e.g., as reported by Berger, S. et al., Biochemistry 18 5143–5149 [1979]) from cells (e.g., a nontransformed human T-cell source) producing polypeptides exhibiting the desired activity. The double-stranded cDNAs from this total mRNA can be constructed by using primer-initiated reverse transcription (Verme, I., Biochem. Biophys. Acta, Vol. 473, pgs. 1–38 [1977]) to make first the complement of each MRNA sequence, and then by priming for second strand synthesis (Land, H. et al., Nucleic Acids Res., 9: 2251–2266 [1981]). Subsequently, the cDNAs can be cloned by joining them to suitable plasmid or bacteriophage vectors (Rougeon, F. et al., Nucleic Acids Res., 2, 2365–2378 [1975]) or Scherer, G. et al., Dev. Biol. 86, 438–447 [1981]) through complementary homopolymeric tails (Efstratiadis, A. et al., Cell, 10, 571–585 [1977]) or cohesive ends created with linker segments containing appropriate restriction sites (Maniatis et al., *Molecular Cloning: A Laboratory Manual*, Cold Spring Harbor Laboratory, New York 1982), and then transforming a suitable host. (See generally, Efstratiadis, A., and Villa-Kormaroff, L., "Cloning of double stranded cDNA" in Setlow, J. and Hollaender, A. (eds.) Genetic Engineering, Vol, 1, Plenum Publishing Corp., New York, U.S.A. [1982].)

A preferred source of mRNA encoding the desired polypeptides are cells whose supernatants contain the B-cell, T-cell and/or mast cell stimulating activities, or other activities associated with the polypeptides of the present invention. One such line is the mouse T-cell line Cl.Ly1$^+$2$^-$/9 (A.T.C.C. Accession No. CRL8179) (Nabel, G. et al., Nature 291:332–334 (1981)). In general, suitable T-cells can be obtained from a variety of sources, such as mammalian (e.g. human) spleen, tonsils and peripheral blood. T-cell clones, such as those isolated from peripheral blood T-lymphocytes, may also be used (see, *Research Monographs in Immunology*, eds. von Doehmer, H. and Haaf, V.; Section D: "Human T-Cell Clones", vol.8, pgs. 243–333; Elsevier Science Publishers, New York [1985]).

Production of mRNAs capable of coding for IL-4 by such cells can be confirmed by microinjection of the extracted mRNA into oocytes of *Xenopus laevis*. This microinjection technique is described more fully below, and is disclosed generally in Colman et al., "Export of Proteins from Oocytes of *Xenopus Laevis*", Cell, Vol. 17, pgs. 517–526 (1979); and Maniatis et al. *Molecular Cloning: A Laboratory Manual*, pgs. 350–352 (Cold Spring Harbor Laboratory, New York, 1982).

If the mRNAs coding for a desired IL-4 make up a very small fraction of the total MRNA steps may be necessary to enrich the fractional concentration in order to make the screening procedure for detecting cDNA clones of interest practical. Such procedures are standard in the art and are disclosed in the examples below and in several papers and references, such as Maniatis et al., pgs. 225–228, cited above; Suggs et al., *Proc Natl. Acad. Sci.*, Vol. 78, pgs. 6613–6617 (1981); Parnes et al., *Proc. Natl. Acad. Sci.,* Vol. 78, pgs. 2253–2257 (1981), Davis et al., *Proc. Natl. Acad. Sci.*, Vol. 81, pgs. 2194–2198 (1984) or the like.

A preferred method of de novo preparation of IL-4 cDNAs relies on functional expression of the cDNAs in pcD expression system developed by Okayama and Berg, disclosed in *Mol. Cell. Biol.*, Vol. 2, pgs. 161–170 (1982); and Vol. 3. pgs. 280–289 (1983), and available from Pharmacia (Piscataway, N.J.). Accordingly, these references are incorporated by reference. The pcD expression vector contains the SV40 early promoter, late splicing junction, and the replication origin. This vector permits expression of cDNA inserts in COS 7 monkey cells which provide T antigen for replication of the pcD plasmid. Screening of cDNA libraries includes transfection of pools of plasmid DNA into COS 7 cells using DEAE-Dextran. Since lymphokines, and in particular IL-4s, are secreted proteins, the supernatants from the transfected cells can be assayed for biological activity after incubation for several days. Positive pools are further divided to identify single cDNA clones which give biological activity after transfection.

Briefly, the Okayama and Berg expression vector is constructed as follows. Polyadenylated mRNA is annealed to a polydeoxythymidylic acid (oligo dT) tail attached to the protruding strand of a KpnI digested pBR322 plasmid containing the SV40 early promoter region. That is, the entire vector serves as a primer for cDNA synthesis. After cDNA synthesis, 3' polydeoxycytidylate (oligo dC) tails are attached, follow by Hind III digestion, which lops off (at a unique Hind III site) a fragment of the SV40 DNA to which one of the oligo dC tails is attached. The SV40 early promoter remains intact, and fortuitously occurring Hind III sites of the insert are affected minimally because the hybrid cDNA/RNA is resistant to Hind III digestion. A separately constructed Hind III fragment having a 3' polyguanidylated (oligo dG) tail is annealed to the sticky end left by the Hind III digestion. The vector is circularized and treated with $E.$ $coli$ RNase H, DNA polymerase I, and DNA ligase to replace the RNA strand with DNA. The vectors are cloned in $E. coli$ to form the cDNA library. The SV40 elements permit the vectors to be expressed in eucaryotic cells as well as procaryotic cells, and particularly in mammalian cells, such as COS7 monkey cells or Chinese hamster ovary (CHO) cells.

Once the cDNA library in the Okayama/Berg plasmid vector has been completed, the cDNA clones are collected, and random pools checked for the presence of the desired cDNAs by standard procedures, e.g. hybrid selection, detection of antigenic determinants on expressed products, and/or functional assays. Positive pools can then be probed with a cDNA from an induced T cell line. Thereafter, the positive, probed pools are divided into individual clones which are further tested by transfection into a suitable host (such as a mammalian cell culture), and the host supernatant assayed for activity.

II. Preparation of IL-4 cDNAs Via Hybridization Probes Derived from Disclosed cDNAs The cDNAs disclosed herein can be used as probes to identify homologous sequences in different cell types, as an alternative to de novo isolation and cloning of the IL-4 coding nucleotides. Standard techniques are employed, e.g. Beltz et al., "Isolation of Multigene Families and Determination of Homologies by Filter Hybridization Methods," *Methods in Enzymology*, Vol. 100, pgs. 266–285. (1983); and Callahan et al., "Detection and Cloning of Human DNA Sequences Related to the Mouse Mammary Tumor Virus Genome," *Proc. Natl. Acad. Sci.*, Vol. 79, pgs. 5503–5507 (1982), the former reference being incorporated by reference. Basically, the cDNAs of the invention are used to construct probes (using standard techniques, e.g. see Maniatis et al., cited above) for screening at low hybridization stringencies genomic or cDNA libraries (again, constructed by standard techniques) of a cell type suspected of producing IL-4. Standard screening procedures are employed, e.g. Grunstein et al., *Proc. Natl. Acad. Sci.*, Vol. 72, pgs. 3961–3965 (1975); or Benton et al., *Science*, Vol. 196, pgs. 180–183 (1977).

As described more fully below, human IL-4 was isolated by a murine IL-4 probe. Subsequent analysis indicated about 70% homology between selected regions of the human and mouse cDNAs. Given the evolutionary distance between mice and humans it is believed that most, if not all, mammalian IL-4 genes are detectable by probes constructed from one or more cDNAs of the invention, Wilson et. al. "Biochemical Evolution", *Ann. Rev. Biochem.*, Vol. 46, pgs. 573–639 (1977); Kimura, "The Neutral Theory of Molecular Evolution," Chapter 11 in Nei and Koehn, Eds. *Evolution of Genes and Proteins* (Sinauer Associates, Sunderland, Mass., 1983).

III. Preparation of Mutant IL-4s by Protein Engineering

Once nucleic acid sequence and/or amino acid sequence information is available for a native protein a variety of techniques become available for producing virtually any mutation in the native sequence. Shortle, in *Science*, Vol. 229, pgs. 1193–1201 (1985), reviews techniques for mutating nucleic acids which are applicable to the present invention. Preferably, mutants of the native IL-4s, i.e. IL-4 muteins, are produced by site-specific oligonucleotide-directed mutagenesis, e.g. Zoller and Smith, *Methods in Enzymology*, Vol. 100, pgs. 468–500 (1983); Mark et al., U.S. Pat. No. 4,518,584 entitled "Human Recombinant Interleukin-2 Muteins, " which are incorporated by reference; or by so-called "cassette" mutagenesis described by Wells et al., in *Gene*, Vol. 34, pgs. 315–323 (1985); and Estell et al., *Science*, Vol. 233, pgs. 659–663 (1986); and also described essentially by Mullenbach et al., *J. Biol. Chem.*, Vol. 261, pgs. 719–722 (1986), and Feretti et al., *Proc. Natl. Acad. Sci.*, Vol. 83, pgs. 597–603 (1986). In sections below the notation used by Estell et al. (cited above) to identify muteins is followed and generalized. For example, "human IL-4 mutein Leu$^{82}$" (or simply "Leu$^{82}$" if the native protein is understood from the context) indicates a polypeptide whose amino acid sequence is identical to that of the native protein except for position 82 with respect to the N-terminus. At that position Leu has been substituted for Phe. Where the mutein contains more than one substitution, e.g. Leu for Phe at position 82, and Asp for Asn at position 111, the mutein is referred to as human IL-4 mutein (Leu$^{82}$, Asp$^{111}$). Deletions are indicated by "$\Delta$'s". For example, a mutein lacking Gln at position 71 is referred to as human IL-4 mutein $\Delta^{71}$. Insertions are indicated by "IS(Xaa)'s". For example, a mutein with a Leu inserted after Gln at position 71 is referred to as human IL-4 mutein IS$^{71}$(Leu). Thus, human IL-4 mutein (Ser$^{13}$, $\Delta^{71}$, IS$^{94}$(Gly)) represents the native human IL-4 sequence which has been modified by replacing Thr by Ser at position 13, deleting Gln at position 71, and inserting Gly immediately after Ala at position 94. Insertion of multiple amino acids at the same site is indicated by IS$^{i}$(Xaa$_1$-Xaa$_2$-Xaa$_3$- . . . ), where Xaa$_1$-Xaa$_2$-Xaa$_3$. . . is the sequence inserted after position i. N-terminal additions are indicated by superscript "0", e.g. IS$^{0}$(Xaa), and a sequence of deletions, for example of amino acids 6–10, is designated either as $\Delta^{6-10}$ or as ($\Delta^6$, $\Delta^7$, $\Delta^8$, $\Delta^9$, $\Delta^{10}$).

Most preferably cassette mutagenesis is employed to generate human IL-4 muteins. As described more fully below, a synthetic human IL-4 gene has been constructed with a sequence of unique (when inserted in a appropriate vector) restriction endonuclease sites spaced approximately uniformly along the gene. The unique restriction sites allow segments of the gene to be conveniently excised and replaced with synthetic oligonucleotides (i.e. "cassettes") which code for desired muteins.

Determination of the number and distribution of unique restriction sites entails the consideration of several factors including (1) preexisting restriction sites in the vector to be employed in expression, (2) whether species or genera-specific codon usage is desired, and (3) the convenience and reliability of synthesizing and/or sequencing the segments between the unique restriction sites.

IV. Biological Properties and Assays for IL-4 Activity

Mammalian IL-4 of the invention is defined in terms of biological activities and/or homology with the disclosed embodiments. Mammalian IL-4s of the invention include proteins and muteins (of the disclosed native polypeptides) which are homologous to the disclosed native polypeptides and which exhibit both BCGF activity and TCGF activity. Mammalian IL-4s of the invention are alternatively defined by their biological activities (defined more fully below) which include BCGF activity and TCGF activity (which is collectively referred to herein as IL-4 activity) as well as at least one or more activities selected from the group of activities consisting of MHC antigen induction activity, Fc-epsilon receptor induction activity, GM-CSF stimulated granulocyte colony growth potentiating activity, interleukin-2 TCGF potentiating activity, and $IgG_1$ and IgE induction activity.

It is believed that IL-4s are species specific in their activities. That is, for example, human IL-4 exhibits TCGF activity as assayed by human T cell lines, but not as assayed by murine T cell lines. And conversely, murine IL-4 exhibits TCGF activity as assayed by murine T cell lines, but not as assayed by human T cell lines, Mosmann et al., "Species-Specificity of T Cell Stimulating Activities of IL-2 and BSF-1 (IL-4): Comparison of Normal and Recombinant, Mouse and Human IL-2 and BSF-1 (IL-4)," *J. Immunol*, Vol. 138, pgs. 1813–1816 (1986) (in press).

A. TCGF Activity

Several standard assays have been described for TCGF activity, e.g. Devos et al., *Nucleic Acids Research*, Vol. 11, pgs. 4307–4323 (1983); Thurman et al., *J. Biol. Response Modifiers*, Vol. 5, pgs 85–107 (1986); and Robert-Guroff et al., Chapter 9 in Guroff, Ed. *Growth and Maturation Factors* (John Wiley, New York, 1984). Accordingly these references are incorporated by reference for their descriptions of TCGF activity assays. Generally, the TCGF assays are based on the ability of a factor to promote the proliferation of peripheral T lymphocytes or IL-2 dependent T cell lines, e.g. Gillis et al. *J. Immunol.*, Vol. 120, pg. 2027 (1978). Proliferation can be determined by standard techniques, e.g. tritiated thymidine incorporation, or by calorimetric methods, Mosmann, *J. Immunol. Meth.*, Vol. 65, pgs. 55–63 (1983).

By way of example, human TCGF activity can be assayed by the following steps: (1) washed human peripheral blood lymphocytes (about $2 \times 10^5$ in 50 microliters) previously stimulated with phytohemagglutinin (PHA) for 7 days and subsequently cultured for 7 days with IL-2 are added to a microtiter well; (2) dilutions (50 microliter) of the TCGF-containing material are added to each well; (3) the lymphocytes are incubated 72 hours at 37° C.; (4) tritiated thymidine (about 20 microliters, 20 microcuries/ml) is added to each well; and (5) cells are harvested onto filter paper strips, washed, and counted in a scintillation counter.

As described more fully in the examples, some forms of IL-4 have the capability of potentiating the TCGF activity of IL-2. "Potentiation" as used herein in reference to such activity means that the maximal level of proliferation in a TCGF assay system caused by IL-2 is increased by the addition of IL-4.

B. BCGF Activity

BCGF activity is defined by an assay disclosed by Howard et al., *J. Exp. Med*, Vol. 155, pgs. 914–923 (1982), which is incorporated herein by reference. Assays for BCGF are reviewed generally by Howard and Paul, in *Ann. Rev. Immunol.*, Vol. 1, pgs. 307–333 (1983). Briefly, BCGF activity is measured by the degree to which purified resting B cells are stimulated to proliferate in the presence of a submitogenic concentration anti-IgM, or like antigen. By way of example, assay of human BCGF activity can be carried out by the following steps:

Enriched B cell populations are obtained from peripheral blood, spleen, tonsils, or other standard sources by Ficoll/Hypaque density gradient centrifugation (e.g. Pharmacia) and two cycles of resetting with 2-aminoethylisothiouronium bromide-treated sheep erythrocytes to eliminate T cells. Such B cell preparations should contain greater than 95% surface $Ig^+$ cells and greater than 95% cells positive for human B-cell specific antigen, as determined by the anti-human B-cell specific monoclonal antibody B1 available from Coulter (Hialeah, Fla.). T cell contamination should be less than 1% as determined by staining with anti-Leu-1 monoclonal antibodies (Becton-Dickinson, Mountain View, Calif.) or OKT 11 antibodies (Ortho Diagnostics, Westwood, Mass.). 3 milliliter cultures of such B lymphocytes (about $5 \times 10^5$ per ml in Yssel's medium, Yssel et al., *J. Immunol. Meth.*, Vol. 65, pgs. 55–63 (1984), which is incorporated by reference) are activated by either Staphylococcus aureus Cowan I strain (SAC) (e.g. 0.01% solution of SAC, which is available from Calbiochem under the tradename Pansorbin, or which can be prepared as described by Falkoff et al., *J. Immunol.*, Vol. 129, pg. 97–102 (1982)) or anti-IgM antibodies (e.g. BRL, Gaithersburg, MD) coupled to beads, e.g. 5 microgram/ml of Immunobeads available from Bio-Rad (Richmond, Calif.). The B cells are cultured either for 24 hours (in the case of SAC) or 72 hours (for anti-IgM beads) and then repurified by Ficoll/Hypaque density centrifugation to remove SAC particles, beads, nonviable cells, and the like. B cell proliferation is measured by plating about $5 \times 10^4$ B lymphocytes in 50 microliters of medium in 0.2 ml flat-bottomed microtiter wells. Various dilutions of the materials suspected of having BCGF activity are added in a final volume of 50 microliters. Tritiated thymidine incorporation is determined after 48 hours (anti-IgM cultures) or 72 hours (SAC cultures). Similar assays are also disclosed by Muraguchi et al., *J. Immunol.*, Vol. 129, pgs. 1104–1108 (1982); and Yoshizaki et al., *J. Immunol.*, Vol. 128, pgs. 1296–1301 (1981).

C. MHC Antigen Induction

It has been demonstrated that IL-4 can induce the expression of MHC antigens (e.g., Ia in mice) in various cell types of the immune system, particularly B cells, e.g. Zlotnik et al., *J. Immunol.*, Vol. 138, pgs. 4275–4279 (1986) (in press). Roehm et al., in *J. Exp. Med.*, Vol. 160, pgs. 679–694, presented evidence that a factor exhibiting BCGF activity was also capable of inducing the expression of MHC antigens on normal resting B cells. Assays for MHC antigen induction are generalizations of the assays for murine B cells presented in that reference (accordingly it is incorporated by reference). Briefly, immune system cells are exposed to IL-4, and then expression of particular MHC antigens on the cells' surfaces are determined by labeled antibodies specific for that antigen. The degree of induction is determined by comparison of the induced cells with controls. Several different antibodies can be employed for any given species. Several hybridomas are available from the ATCC which produce monoclonal anti-MHC antigen antibodies, and several are available commercially (for example, anti-HLA-DR produced by hybridomas under ATCC accession numbers HB103, HB109, HB110, or HB151; anti-I-A$^{b,d}$ produced by hybridoma under ATCC accession number HB35; anti-HLA-DR L243 available from Becton Dickinson (Mountain View, Calif.); or the like). Some routine experimentation may be required to adapt the assay to a particular species, and to optimize conditions to give the most sensitive read out of MHC antigen levels. For the human MHC antigen induction assay, purified B cells can be prepared as described above, or by similar techniques. Alternatively, MHC induction can be assayed on unpurified preparations of spleen cells. Antibody-labeled cells are preferably detected flow cytometrically, e.g. on a Becton Dickinson FACS-type instrument, or the equivalent.

D. MCGF Activity

It is believed that IL-4s generally exhibit MCGF activity. However, because of the lack of adequate assay techniques MCGF activity has only been demonstrated for rodent IL-4. Murine IL-4 MCGF assays are based on the proliferation of factor dependent murine mast or basophil cell lines. In particular, MCGF activity can be assayed with the murine mast cell line MC/9, which is deposited with the ATCC under accession number CRL 8306, and is described in U.S. Pat. No. 4,559,310 (which is incorporated by reference) and in Nabel et al., *Cell*, Vol. 23, pg. 19 (1981). Murine MCGF assays are also described by Ihle et al., in *J. Immunol.*, Vol. 127, pg. 794 (1981).

Preferably MCGF activity is determined by the calorimetric assay of Mosmann (cited above) with the use of MC/9 cells. Briefly, MC/9 cells are cultured in flat-bottom Falcon microtiter trays ($10^4$ cells/well) in Dulbecco's modified medium supplemented with 4% fetal calf serum 50 $\mu$M 2-mercaptoethanol, 2 mM glutamine, nonessential amino acids, essential vitamins, and varied concentrations of test supernatants in a final volume of 0.1 ml. Fifty micrograms of 3-(4.5-dimethylthiazol-2-yl)-2.5-diphenyl tetrazolium bromide (Sigma) in 10 $\mu$l of phosphate-buffered saline were added to each cell culture after a 20-hr incubation. Four hours later, 0.1 ml of 0.04M HCl in isopropanol was added to solubilize the colored formazan reaction product. The absorbance at 570 nm (reference 630 nm) is measured on a Dynatek Microelisa Autoreader (MR580), or similar instrument.

E. Fc-epsilon Receptor Induction

It has been discovered that IL-4 induces Fc-epsilon expression on B cells and on T cells, but particularly on human B cells stimulated by anti-IgM antibodies, or like antigen. It has also been discovered that gamma interferon specifically inhibits IL-4 induced Fc-epsilon expression on B cells.

Preferably, the assay for Fc-epsilon receptor induction proceeds initially as for the BCGF assay. That is, purified B cell are obtained which are then stimulated with anti-IgM antibody (or like antigen) and are exposed to IL-4. Finally the cells are assayed for Fc-epsilon receptors.

Several assays are available for quantifying Fc-epsilon receptors on cell surfaces, e.g. Yodoi and Ishizaka, *J. Immunol.*, Vol. 122, pgs. 2577–2583 (1979); Hudak et al.,*J. Immunol Meth.*, Vol. 84, pgs. 11–24 (1985); and Bonnefoy et al., *J. Immunol. Meth.*, Vol. 88, pgs. 25–32 (1986). In particular, Fc-epsilon receptors can be measured flowcyctometrically with labeled monoclonal antibodies specific for the receptors, e.g. using a Becton Dickinson FACS-IV, or like instrument. Fc-epsilon receptor specific monoclonals can be constructed using conventional techniques.

F. IgG$_1$ and IgE Induction

IL-4 induces the secretion of IgE and IgG$_1$ isotypes in lipopolysaccharide (LPS)-activated B cells, e.g. Coffman et al., *J. Immunol.*, Vol. 136, pgs. 4538–4541 (1986); Sideras, et al., *Eur. J. Immunol.*, Vol. 15, pgs. 586–593 (1985). These activities can be measured by standard immunoassays for antibody isotype, such as described by Coffman et al., *J. Immunol.*, Vol. 136, pgs. 949–954 (1986). Briefly, B cells are LPS activated by culturing them with, for example, about 4 micrograms/ml of Salmonella typhimurium LPS (available from Sigma) or about 50 microgram/ml LPS extracted from *E. coli* 055 (as described by Sideras et al., cited above). After 4–8 days culture supernatants are harvested for assaying. Standard isotype-specific ELISA-type assays can be used to measure the various isotype concentrations. Anti-isotype antibodies for the assay are available commercially, or can be obtained from the ATCC.

G. Colony Stimulating Factor (CSF) Activity

To determine CSF activity, hemopoietic cells, e.g. bone marrow cells or fetal cord blood cells, are made into a single cell suspension. The individual cells are then "immobilized" in a semi-solid (agar) or viscous (methylcellulose) medium containing nutrients and usually fetal calf serum. In the presence of an appropriate stimulating factor, individual cells will proliferate and differentiate. Since the initial cells are immobilized, colonies develop as the cells proliferate and mature. These colonies can be scored after 7–14 days, Burgess, A., *Growth Factors and Stem Cells*, pgs. 52–55, Academic Press, New York [1984]. (For specific application to the growth of granulocytes and macrophages, see Bradely, T. and Metcalf, D., Aust. J. Exp. Biol. Med. Sci. Vol. 44, pgs. 287–300 [1966], and see generally Metcalf, D., *Hemopoietic Colonies*, Springer-Verlag, Berlin [1977]). If desired, individual colonies can be extracted, placed on microscope slides, fixed and stained with Wright/Geimsa (Todd-Sanford, *Clinical Diagnosis by Laboratory Methods*, 15th Edition, Eds. Davidson and Henry [1974]). Morphological analysis of cell types present per single colony can then be determined.

Bone marrow cells collected from patients with nonhematologic disease are layered over Ficoll (type 400, Sigma Chemical Co., St. Louis, Mo.), centrifuged (2,000 rpm's, 20 min), and the cells at the interface removed. These cells are washed twice in Iscove's Modified Dulbecco's Medium containing 10% fetal calf serum (FCS), resuspended in the same medium and the adherent cells removed by adherence to plastic Petri dishes. The nonadherent cells are added at $10^5$ cells/ml to Iscove's Medium containing 20% FCS, 50 $\mu$M 2-mercaptoethanol, 0.9% methylcellulose and varied concentrations of either supernatants known to contain colony stimulating activity or test supernatants. One ml aliquots are plated in 35 mm petri dishes and cultured at 37° C. in a fully humidified atmosphere of 6% $CO_2$ in air. Three days after the initiation of the culture, 1 unit of erythropoietin is added to each plate. Granulocyte-macrophage colonies and erythroid bursts are scored at 10–14 days using an inverted microscope.

Cord blood cells collected in heparin are spun at 2,000 rpm's for 6 min. The white blood cells at the interface between the plasma and red blood cell peak are transferred to a tube containing 0.17N ammonium chloride and 6% FCS. After 5 min on ice, the suspension is underlaid with 4 ml FCS and centrifuged for 6 mins at 2,000 rpm. The cell pellet is washed with Dulbecco's phosphate buffered saline and put through the Ficoll and plastic adherence steps as described above for bone marrow cells. The low density nonadherent cells are collected and placed at $10^5$ cells/ culture in the semi-solid culture medium as described above.

At the end of the assays, the cellular composition is determined after applying the individual colonies to glass slides and staining with Wright-Giemsa. Eosinophils are determined by staining with Luxol Fast Blue (Johnson, G. and Metcalf, D., Exp. Hematol. Vol. 8, pgs. 549–561 [1980]).

"Potentiation" as used herein in reference to GM-CSF stimulated granulocyte growth means that granulocyte colonies in the assays described above are larger when GM-CSF is used with IL-4 than when GM-CSF is used to stimulate colony growth alone.

V. Purification and Pharmaceutical Compositions

The polypeptides of the present invention expressed in *E. coli*, in yeast or in other cells can be purified according to standard procedures of the art, including ammonium sulfate precipitation, fractionation column chromatography (e.g., ion exchange, gel filtration, electrophoresis, affinity chromatography, etc.) and ultimately crystallization (see generally "Enzyme Purification and Related Techniques," Methods in Enzymology, 22:233–577 [1977] and Scopes, R., *Protein Purification: Principles and Practice*, Springer-Verlag, New York [1982]). Once purified, partially or to homogeneity, the polypeptides of the invention may be used for research purposes, e.g., as a supplement to cell growth media (e.g., minimum essential medium Eagle, Iscove's modified Dulbecco Medium or RPMI 1640; available from Sigma Chemical Company (St. Louis, Mo.) and GIBCO Division (Chagrin Falls, Ohio)) and as an antigenic substance for eliciting specific immunoglobulins useful in immunoassays, immunofluorescent stainings, etc. (See generally, *Immunological Methods*, Vols. I & II, Eds. Lefkovits, I. and Pernis, B., Academic Press, New York, N.Y. [1979 & 1981]; and *Handbook of Experimental Immunology*, ed. Weir, D., Blackwell Scientific Publications, St. Louis, Mo. [1978].)

The polypeptides of the present invention may also be used in pharmaceutical compositions, e.g., to enhance natural defense against various infections. Thus, patients with rheumatoid arthritis, in need of a transplant, or with immunodeficiency caused by cancer chemotherapy, advanced age, immunosuppressive agents, etc., may be treated with such polypeptides. The compositions can selectively stimulate various components of the immune system, either alone or with other agents well known to those skilled in the art. In particular, the compositions may include other immune-reactive agents, such as lymphokines (e.g. IL-1, IL-2, etc.), any of the colony stimulating factors, immunoglobulins, etc., in view of the potentiating activities of the polypeptides of the present invention. The polypeptides will also find use in situations (in vivo or in vitro) in which enhanced cellular proliferation or immunoglobulin production is desired.

For preparing pharmaceutical compositions containing the polypeptides described by this invention, these polypeptides are compounded by admixture with preferably inert, pharmaceutically acceptable carriers. Suitable carriers and processes for their preparation are well known in the art (see, e.g., Remington's Pharmaceutical Sciences and U.S. Pharmacopeia: National Formulary, Mack Publishing Company, Easton, Pa. [1984]). The preferred course of administration is parenteral and can include use of mechanical delivery systems.

Preferably, the pharmaceutical composition is in unit dosage form. In such form, the preparation is subdivided into unit doses containing appropriate quantities of the active component. The quantity of active compound in a unit dose of preparation may be varied or adjusted from 1 $\mu$g to 100 mg, according to the particular application and the potency of the active ingredient. The composition can, if desired, also contain other therapeutic agents.

The dosages may be varied depending upon the requirement of the patient, the severity of the condition being treated and the particular compound being employed. The term "effective amount" as used herein is meant to take these factors into account when dosages are considered. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day.

VI. Expression Systems

A wide range of expression systems (i.e. host-vector combinations) can be used to produce the proteins and muteins of present invention. Possible types of host cells include but are not limited to cells from bacteria, yeast, insects, mammals, and the like. Optimizing the expression of a particular protein or mutein depends on many factors, including (1) the nature of the protein or mutein to be expressed, e.g. the expressed product may be poisonous to some host systems, (2) whether, and what type of, post-translational modifications are desired, e.g. the extent and kind of glycosylation desired may affect the choice of host, (3) the nature of the 5' and 3' regions flanking the coding region of the protein or mutein of interest, e.g. selection of promoters and/or sequences involved in the control of translation is crucial for efficient expression, (4) whether transient or stable expression is sought, (5) the ease with which the expressed product can be separated from the proteins and other materials of the host cells and/or culture medium, (6) the ease and efficiency of transfecting hosts which transiently express the protein or mutein of interest, (7) the scale of cell culture employed to express the protein or mutein of interest, (8) whether the protein or mutein of interest is expressed fused to a fragment of protein endogenous to the host, and like factors.

In general prokaryotes are preferred for cloning the DNA sequences of the invention. General guides for implementing prokaryotic expression systems are provided by Maniatis et al., *Molecular Cloning: A Laboratory Manual* (Cold Spring Harbor Laboratory, New York, 1982); Perbal, *A Practical Guide to Molecular Cloning* (John Wiley & Sons, New York, 1984); Glover, *DNA Cloning: A Practical Approach*, Vol. I and II (IRL Press, Oxford, 1985); and de Boer et al., "Strategies for Optimizing Foreign Gene Expression in *Escherichia coli*," in *Genes: Structure and Expression*, Kroon, ed. (John Wiley & Sons, New York, 1983). For example, *E. coli* K12 strain 294 (ATCC No. 31446) is particularly useful. Other microbial strains which may be used include *E. coli* strains such as *E. coli* B, and *E. coli* X1776 (ATCC No. 31537). These examples are, of course, intended to be illustrative rather than limiting.

Prokaryotes may also be used for expression. The aforementioned strains, as well as *E. coli* W3110 (Fs$^-$, $\lambda^-$, prototrophic, ATCC No. 27325), bacilli such as *Bacillus subtilus*, and other enterobacteriaceae such as *Salmonella typhimurium* or *Serratia marcesans*, and various pseudomonas species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an E. coli species (Bolivar, et al., Gene Vol. 2, pg. 95 (1977)). pBR322 contains genes for ampicillin and tetracycline resistance and thus provides easy means for identifying transformed cells. The pBR322 plasmid, or other microbial plasmid must also contain, or be modified to contain, promoters which can be used by the microbial organism for expression of its own proteins. Those promoters most commonly used in recombinant DNA construction include the β-lactamase (penicillinase) and lactose promoter systems (Chang et al, Nature, Vol. 275, pg. 615 (1978); Itakura, et al, Science, Vol. 198, pg. 1056 (1977); (Goeddel, et al Nature Vol. 281, pg. 544 (1979)) and a tryptophan (trp) promoter system (Goeddel, et al, Nucleic Acids Res., Vol. 8, pg. 4057 (1980); EPO Appl Publ No. 0036776). While these are the most commonly used, other microbial promoters have been discovered and utilized, and details concerning their nucleotide sequences have been published, enabling a skilled worker to ligate them functionally with plasmid vectors (Siebenlist, et al, Cell Vol. 20, pg. 269 (1980)).

In addition to prokaryotes, eukaryotic microbes, such as yeast cultures may also be used. Saccharomyces cerevisiae, or common baker's yeast is the most commonly used among eukaryotic microorganisms, although a number of other strains are commonly available. For expression in Saccharomyces, the plasmid YRp7, for example, (Stinchcomb, et al, Nature, Vol. 282, pg 39 (1979); Kingsman et al, Gene, Vol. 7, pg. 141 (1979); Tschemper, et al, Gene, Vol. 10, pg. 157 (1980)) is commonly used. This plasmid already contains the trp1 gene which provides a selection marker for a mutant strain of yeast lacking the ability to grow in tryptophan, for example ATCC No. 44076 or PEP4-1 (Jones, Genetics, Vol. 85, pg. 12 (1977)). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman, et al., J. Biol. Chem., Vol. 255, pg. 2073 (1980)) or other glycolytic enzymes (Hess, et al, J. Adv. Enzyme Reg., Vol. 7, pg. 149 (1968); Holland, et al, Biochemistry, Vol. 17, pg. 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter regions for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization (Holland, ibid.). Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However interest has been greatest in vertebrate cells, and propagation of vertebrate cells in culture (tissue culture) has become a routine procedure in recent years [Tissue Culture, Academic Press, Kruse and Patterson, editors (1973)]. Examples of such useful host cell lines are VERO and HeLa cells, Chinese hamster ovary (CHO) cell lines, and W138, BHK, COS7, mouse myeloma (ATCC No. TIB 19 or TIB 20), and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers, et al, Nature, Vol. 273, pg 113 (1978) incorporated herein by reference. Smaller or larger SV40 fragments may also be used, provided there is included the approximately 250 bp sequence extending from the HindIII site toward the Bgl I site located in the viral origin of replication. Further, it is also possible, and often desirable, to utilize promoter or control sequences normally associated with the desired gene sequence, provide such control sequences are compatible with the host cell systems.

An origin of replication may be provided either by construction of the vector to include an exogenous origin, such as may be derived from SV40 or other viral (e.g. Polyoma, Adeno, VSV, BPV, etc.) source, or may be provided by the host cell chromosomal replication mechanism. If the vector is integrated into the host cell chromosome, the latter is often sufficient.

In selecting a preferred host cell for transfection by the vectors of the invention which comprise DNA sequences encoding both t-PA and DHFR protein, it is appropriate to select the host according to the type of DHFR protein employed. If wild type DHFR protein is employed, it is preferable to select a host cell which is deficient in DHFR, thus permitting the use of the DHFR coding sequence as a marker for successful transfection in selective medium which lacks hypoxanthine, glycine, and thymidine. An appropriate host cell in this case is the Chinese hamster ovary (CHO) cell line deficient in DHFR activity, prepared and propagated as described by Urlaub and Chasin, Proc. Natl. Acad. Sci. (U.S.A.) Vol. 77, pg. 4216 (1980), incorporated herein by reference.

On the other hand, if DHFR protein with low binding affinity for MTX is used as the controlling sequence, it is not necessary to use DHFR resistant cells. Because the mutant DHFR is resistant to methotrexate, MTX containing media can be used as a means of selection provided that the host cells are themselves methotrexate sensitive. Most eukaryotic cells which are capable of absorbing MTX appear to be methotreaxate sensitive. One such useful cell line is a CHO line, CHO-K1 ATCC No. CCL 61.

Invertebrate expression systems include the larvae of silk worm, Bombyx mori, infected by a baculovirus vector, BmNPV, described by Maeda et al., in Nature, Vol. 315, pgs. 892–894 (1985); and in Saibo Koguku, Vol. 4, pgs. 767–779 (1985).

EXAMPLES

The following examples serve to illustrate the present invention. Selection of vectors and hosts as well as the concentration of reagents, temperatures, and the values of other variable parameters are only to exemplify application of the present invention and are not to be considered as limitations thereof.

Example I

De Novo Preparation of Murine IL-4 cDNAs from Cl.Ly1+ 2−/9 Cells and Transient Expression in COS 7 Monkey Cells cDNA clones coding for IL-4 were isolated from the murine helper T cell line Cl.Ly1$^+$2$^-$/9, which is deposited with the ATCC under accession number CRL 8179 and described by Nabel et al., in *Cell*, Vol. 23, pgs. 19–28 (1981), and in *Proc. Natl. Acad. Sci.*, Vol. 78, pgs. 1157–1161 (1981). Other murine cells known to produce BCGF activity include the EL-4 line, available from the ATCC under accession number TIB 39. The procedures used in this example have been disclosed in Lee et al., *Proc. Natl. Acad. Sci.*, Vol. 83, pgs. 2061–2065 (1986), which is incorporated by reference. Briefly, a pcD cDNA library was constructed with messenger RNA (mRNA) from concanavalin A (conA) induced Cl.Ly1$^+$2$^-$/9 cells following the procedure of Okayama and Berg, described above. IL-3 and GM-CSF clones were eliminated from a large sublibrary of randomly selected clones by hybridization with $^{32}$P-labeled cDNA probes. Pools and/or individual clones from the remainder of the sublibrary were screened for IL-4 cDNA by transfecting COS 7 monkey cells and testing culture supernatants for MCGF and TCGF activity.

A. Induction of IL-4 Production

Cl.Ly1$^+$2$^-$/9 cells were induced to produce IL-4 mRNA by Con A as follows. The cells are cultured at 5×10$^5$/ml in Dulbecco's Modified Eagles medium (DME) with 4% heat-inactivated fetal calf serum, 5×10$^{-5}$M 2-mercaptoethanol (2-ME), 2 mM glutamine, non-essential amino acids, essential vitamins and 2 μg/ml Con A. After 12–14 hrs. incubation at 37° C. in 10% $CO_2$, the cell suspension is centrifuged at 1500 rpm for 10 minutes. The cell pellets are collected and frozen immediately at −70° C.

B. Isolation of mRNA

Total cellular DNA was isolated from cells using the guanidine isothiocyanate procedure of Chirgwin, J. et al., (Biochemistry, 18:5294–5299 [1979]). Frozen cell pellets from ConA-induced Cl.Ly1$^+$2$^-$/9 cells (12 hrs after stimulation) were suspended in guanidine isothiocyanate lysis solution. Twenty ml of lysis solution was used for 1.5×10$^8$ cells. Pellets were resuspended by pipetting, then DNA was sheared by 4 passes through a syringe using a 16 gauge needle. The lysate was layered on top of 20 ml of 5.7M CsCl, 10 mM EDTA in 40 ml polyallomer centrifuge tube. This solution was centrifuged at 25,000 rpm in Beckman SW28 rotor (Beckman Instruments, Inc., Palo Alto, Calif.) for 40 hrs at 15° C. The guanidine isothiocyanate phase containing DNA was pipetted off from the top, down to the interface. The walls of the tube and interface were washed with 2–3 ml of guanidine isothiocyanate lysis solution. The tube was cut below the interface with scissors, and the CsCl solution was decanted. RNA pellets were washed twice with cold 70% ethanol. Pellets were then resuspended in 500 μl of 10 mM Tris.HCl pH 7.4, 1 mM EDTA, 0.05% SDS. 50 μl of 3M sodium acetate was added and RNA was precipitated with 1 ml ethanol. About 0.3 mg total RNA was collected by centrifuging and the pellets washed once with cold ethanol.

Washed and dried total RNA pellet was resuspended in 900 μl of oligo (dT) elution buffer (10 mM Tris.HCl, pH 7.4, 1 mM EDTA, 0.5% SDS). RNA was heated for 3 min. at 68° C. and then chilled on ice. 100 μl of 5M NaCl was added. The RNA sample was loaded onto a 1.0 ml oligo (dT) cellulose column (Type 3, Collaborative Research, Waltham, Mass.) equilibrated with binding buffer (10 mM Tris.HCl pH 7.4, 1 mM EDTA, 0.5M NaCl, 0.5% SDS.) Flow-through from the column was passed over the column twice more. The column was then washed with 20 ml binding buffer. PolyA$^+$ mRNA was collected by washing with elution buffer. RNA usually eluted in the first 2 ml of elution buffer. RNA was precipitated with 0.1 volume 3M sodium acetate (pH 6) and two volumes of ethanol. The RNA pellet was collected by centrifugation, washed twice with cold ethanol, and dried. The pellet was then resuspended in water. Aliquots were diluted, and absorbance at 260 nm was determined.

C. Construction of pcD cDNA Library

1) Preparation of Vector Primer and Oligo(dG)-Tailed Linker DNAs

The procedure of Okayama & Berg (Mol. & Cell. Biol. Voil. 2, pgs. 161–170 [1982]) was used with only minor modifications. The pcDVl and pLl plasmids are described by Okayama & Berg (Mol. & Cell. Biol. 3:380–389 [1983]) and are available from Pharmacia (Piscataway, N.J.). Specifically, a modified pcDVl plasmid was used which contained an NsiI site at the previous location of the KpnI site.

An 80 μg sample of pcDVl DNA was digested at 30° C. with 20 U of KpnI endonuclease in a reaction mixture of 450 μl containing 6 mM Tris.HCl (pH 7.5), 6 mM $MgCl_2$, 6 mM NaCl, 6 mM 2-ME, and 0.1 mg of bovine serum albumin (BSA) per ml. After 16 hr the digestion was terminated with 40 μl of 0.25M EDTA (pH 8.0) and 20 μl of 10% sodium dodecyl sulfate (SDS); the DNA was recovered after extraction with water-saturated 1:1 phenol-CHCl$_3$ (hereafter referred to as phenol-CHCl$_3$) and ethanol precipitation. Homopolymer tails averaging 60, but not more than 80, deoxythymidylate (dT) residues per end were added to the NsiI endonuclease-generated termini with calf thymus terminal transferase as follows: The reaction mixture (38 μl) contained sodium cacodylate-30 mM Tris.HCl pH 6.8 as buffer, with 1 mM CoCl$_2$, 0.1 mM dithiothreitol, 0.25 mM dTTP, the NsiI endonuclease-digested DNA, and 68 U of the terminal deoxynucleotidyl transferase (P-L Biochemicals, Inc., Milwaukee, Wis.). After 30 min. at 37° C. the reaction was stopped with 20 μl of 0.25M EDTA (pH 8.0) and 10 μl of 10% SDS, and the DNA was recovered after several extractions with phenol-CHCl$_3$ by ethanol precipitation. The DNA was then digested with 15 U of EcoRI endonuclease in 50 μl containing 10 mM Tris.HCl pH 7.4, 10 mM MgCl$_2$, 1 mM dithiothreitol, and 0.1 mg of BSA per ml for 5 hr at 37° C. The large fragment, containing the SV40 polydenylation site and the pBR322 origin of replication and ampicillin-resistance gene, was purified by agarose (1%) gel electrophoresis and recovered from the gel by a modification of the glass powder method (Vogelstein, B. & Gillespie, D., Proc. Natl. Acad. Sci. 76: 615–619 [1979]). The dT-tailed DNA was further purified by absorption and elution from an oligo (dA)-cellulose column as follows: The DNA was dissolved in 1 ml of 10 mM Tris.HCl pH 7.3 buffer containing 1 mM EDTA and 1M NaCl, cooled at 0° C., and applied to an oligo (dA)-cellulose column (0.6 by 2.5 cm) equilibrated with the same buffer at 0° C. and eluted with water at room temperature. The eluted DNA was precipitated with ethanol and dissolved in 10 mM Tris.HCl pH 7.3 with 1 mM EDTA.

The oligo (dG) tailed linked DNA was prepared by digesting 75 μg of pLl DNA with 20 U of PstI endonuclease in 450 μl containing 6 mM Tris.HCl pH 7.4, 6 mM MgCl$_2$, 6 mM 2-ME, 50 mM NaCl, and 0.01 mg of BSA per ml. After 16 hr at 30° C. the reaction mixture was extracted with phenol-CHCl$_3$ and the DNA was precipitated with alcohol. Tails of 10 to 15 deoxyguanylate (dG) residues were then added per end with 46 U of terminal deoxynucleotidyl transferase in the same reaction mixture (38 µl) as described above, except that 0.1 mM dGTP replaced dTTP. After 20 min. at 37° C. the mixture was extracted with phenol-CHCl$_3$, and after the DNA was precipitated with ethanol it was digested with 35 U of HindIII endonuclease in 50 µl containing 20 mM Tris.HCl pH 7.4, 7 mM MgCl$_2$, 60 mM NaCl, and 0.1 mg of BSA at 37° C. for 4 hr. The small oligo (dG)-tailed linker DNA was purified by agarose gel (1.8%) electrophoresis and recovered as described above.

2) cDNA Library Preparation

Step 1: cDNA synthesis. The reaction mixture (10 µl) contained 50 mM Tris.HCl pH 8.3, 8 mM MgCl$_2$, 30 mM KCl, 0.3 mM dithiothreitol, 2 mM each dATP, dTTP, dGTP, and dCTP, 20 µCi $^{32}$P-dCTP (3000 Ci/mmole), 3 µg polyA$^+$ RNA from Con-A induced T-cells, 60 units RNasin (a tradenamed ribonuclease inhibitor from Promega Biotec, Inc., Madison, Wis.), and 2 µg of the vector-primer DNA (15 pmol of primer end), and 45 U of reverse transcriptase. The reaction was incubated 60 min at 42° C. and then stopped by the addition of 1 µl of 0.25M ETDA (pH 8.0) and 0.5 µl of 10% SDS; 40 µl of phenol-CHCl$_3$ was added, and the solution was blended vigorously in a Vortex mixer and then centrifuged. After adding 40 µl of 4M ammonium acetate and 160 µl of ethanol to the aqueous phase, the solution was chilled with dry ice for 15 min., warmed to room temperature with gentle shaking to dissolve unreacted deoxynucleoside triphosphates that had precipitated during chilling, and centrifuged for 10 min. in an Eppendorf microfuge. The pellet was dissolved in 10 µl of 10 mM Tris.HCl pH 7.3 and 1 mM EDTA, mixed with 10 µl of 4M ammonium acetate, and reprecipitated with 40 µl of ethanol, a procedure which removes more than 99% of unreacted deoxynucleotide triphosphates. The pellet was rinsed with ethanol.

Step 2: Oligodeoxycytidylate [oligo (dC)] addition. The pellet containing the plasmid-cDNA:mRNA was dissolved in 20 µl of 140 mM sodium cacodylate-30 mM Tris.HCl pH 6.8 buffer containing 1 mM CoCl$_2$, 0.1 mM dithiothreitol, 0.2 µg of poly (A), 70 µM dCTP, 5 µCi $^{32}$P-dCTP, 3000 Ci/mmole, and 60 U of terminal deoxynucleotidyl transferase. The reaction was carried out at 37° C. for 5 min. to permit the addition of 10 to 15 residues of dCMP per end and then terminated with 2 µl of 0.25M EDTA (pH 8.0) and 1 µl of 10% SDS. After extraction with 20 µl of phenol-CHCl$_3$, the aqueous phase was mixed with 20 µl of 4M ammonium acetate, the DNA was precipitated and reprecipitated with 80 µl of ethanol, and the final pellet was rinsed with ethanol.

Step 3: HindIII endonuclease digestion. The pellet was dissolved in 30 µl of buffer containing 20 mM Tris.HCl pH 7.4, 7 mM MgCl$_2$, 60 mM NaCl, and 0.1 mg of BSA per ml and then digested with 10 U of HindIII endonuclease for 2 hr at 37° C. The reaction was terminated with 3 µl of 0.25M EDTA (pH 8.0) and 1.5 µl of 10% SDS and, after extraction with phenol-CHCl$_3$ followed by the addition of 30 µl of 4M ammonium acetate, the DNA was precipitated with 120 µl of ethanol. The pellet was rinsed with ethanol and then dissolved in 10 µl of 10 mM Tris.HCl (pH 7.3) and 1 mM EDTA, and 3 µl of ethanol was added to prevent freezing during storage at −20° C.

Step 4: Cyclization mediated by the oligo (dG)-tailed linker DNA. A 9 µl sample of the HindIII endonuclease-digested oligo (dC)-tailed cDNA:mRNA plasmid (about 90% of the sample) was incubated in a mixture (90 µl) containing 10 mM Tris.HCl pH 7.5, 1 mM EDTA, 0.1M NaCl, and 1.8 pmol of the oligo (dG)-tailed linker DNA at 65° C. for 5 min., shifted to 42° C. for 60 min, and then cooled to 0° C. The mixture (90 µl) was adjusted to a volume of 900 µl containing 20 mM Tris.HCl pH 7.5, 4 mM MgCl$_2$, 10 mM (NH$_4$)$_2$SO$_4$, 0.1M KCl, 50 µg of BSA per ml, and 0.1 mM β-NAD; 6 µg of E. coli DNA ligase were added and the solution was then incubated overnight at 12° C.

Step 5: Replacement of RNA strand by DNA. To replace the RNA strand of the insert, the ligation mixture was adjusted to contain 40 µM of each of the four deoxynucleoside triphosphates, 0.15 mM beta-AND, 4 µg of additional E. coli DNA ligase, 16 U of E. coli DNA polymerase I (PolI,) and 9U of E. coli RNase H. This mixture (960 µl) was incubated successively at 12° C. and at room temperature for 1 hr each to promote optimal repair synthesis and nick translation by PolI.

Step 6: Transformation of E. coli. Transformation was carried out using minor modifications of the procedure described by Cohen et al. (Proc. Nat. Acad. Sci. U.S.A., 69:2110–2114 [1972]). E. coli K-12 strain MC1061 (Casadaban, M. and Cohen, S., J. Mol. Biol. 138:179–207 [1980]) was grown to 0.5 absorbancy unit at 600 nm at 37° C. in 300 ml of L-broth. The cells were collected by centrifugation, suspended in 30 ml of 10 mM Pipes. pH 7, 60 mM CaCl$_2$, 15% glycerol and centrifuged at 0° C. for 5 min. The cells were resuspended in 24 ml of the above buffer and incubated again at 0° C. for 5 min.; then, 1.0 ml aliquots of the cell suspensions were mixed with 0.1 ml of the DNA solution (step 5) and incubated at 0° C. for 20 min. Next the cells were kept at 42° C. for 2 min. and thereafter at room temperature for 10 min.; then 1 liter of L-broth was added, and the culture was incubated at 37° C. for 60 min. Ampicillin was added to a concentration of 50 µg/ml. The culture was shaken for an additional 10 hrs. at 37° C. Dilutions of this culture were spread on L-broth agar containing 50 µg/ml ampicillin. After incubation at 37° C. for 12 to 24 hr, individual colonies were picked with sterile tooth-picks. In all, approximately 1×10$^5$ independent cDNA clones were generated.

D. Screening the pcD Library

10$^4$ single clones were picked at random from the T-cell cDNA library and propagated individually in wells of microtiter dishes containing 200 µl L-broth with ampicillin at 50 µg/ml and dimethyl sulfoxide at 7%. To focus only on the novel MCGF activity, 53 IL-3 cDNA clones and one GM-CSF cDNA clone identified by hybridization with the appropriate $^{32}$P-labelled cDNA probes constructed from the clones disclosed by Lee et al., Proc. Natl. Acad. Sci., Vol. 82, pgs. 4360–4364 (1985); and Yokota et al., Proc. Natl. Acad. Sci., Vol. 81, pgs. 1070–1074 (1984). The procedure was carried out as follows: Each plate of 96 cultures was replicated onto nitrocellulose filters for hybridization screening. Hybridizations were performed in 6×SSPE (1×SSPE=180 mM NaCl; 10 mM sodium phosphate, pH 7.4; 1 mm EDTA), 0.1% SDS, 100 µg/ml E. coli tRNA, 50% formamide, for 16 hrs. at 42° C. Hybridizing clones were identified by autoradiography of the washed filter. These clones were removed by sterilizing the microtiter wells containing these clones with ethanol prior to the preparation of clone pools. Pools containing up to 48 cDNA clones were prepared from the microtiter cultures. Two hundred such pools were grown up in 1 liter cultures of L-broth containing 100 µg/ml ampicillin. Plasmid DNA was isolated from each culture and purified by twice banding through CsCl gradients. The DNA representing each pool was transfected into COS7 monkey cells as follows. (COS7 cells are described by Gluzman in Cell, Vol. 23, pgs. 175–180 (1981), and are available from the ATCC under accession number CRL 1651).

One day prior to transfection, approximately 10$^6$ COS 7 monkey cells were seeded onto individual 100 mm plates in DME containing 10% fetal calf serum and 2 mM glutamine. To perform the transfection, the medium was aspirated from each plate and replaced with 4 ml of DME containing 50 mM Tris.HCl pH 7.4, 400 µg/ml DEAE-Dextran and 50 µg of the plasmid DNAs to be tested. The plates were incubated for four hours at 37° C., then the DNA-containing medium was removed, and the plates were washed twice with 5 ml of serum-free DME. DME containing 150 µM Chloroquine was added back to the plates which were then incubated for an additional 3 hrs at 37° C. The plates were washed once with DME and then DME containing 4% fetal calf serum, 2 mM glutamine, penicillin and streptomycin was added. The cells were then incubated for 72 hrs at 37° C. The growth medium was collected and evaluated in the various bioassays.

An initial set of plasmid pools was screened primarily by using proliferation assays for TCGF and MCGF activities with the HT-2 (described more fully below) and MC/9 cell lines, respectively. Among the first 110 pools assayed on these two cell lines, eight produced significant activity in the HT-2 TCGF assay. Several of these pools had weak but significant MCGF activity, but because the MCGF activities were generally weaker and more variable, we did not rely on this assay for identifying positive pools.

Approximately half of the COS supernatants from the random pool transfections were also assayed for Ia inducing activity on mouse B cells. Among the pools tested, each pool shown to be active for TCGF activity was found also to have Ia inducing activity. Thus, there was a perfect correlation between the TCGF activity and the Ia inducing activity.

One pool, 2A, which was reproducibly the most active in all assays, was subdivided into 48 smaller sub-pools. Two subpools were positive for both MCGF and TCGF activities. The single clone, 2A-E3, common to both subpools was then grown individually and its plasmid DNA was transfected into COS 7 cells as described above. The resulting COS supernatant was then assayed for the presence of various activities, including MCGF, TCGF, Ia inducing, and IgE and IgG enhancing activities.

A 366 base-pair-long PstI fragment isolated from clone 2A-E3 (FIG. 1A) and labelled with $^{32}$P was used as a probe to screen pools which had been positive for biological activity as well as other untested pools. The screening was performed by hybridization to filters replicated with the microtiter cultures as described above. Nine hybridizing clones were isolated and their DNA analyzed by restriction mapping. All pools which exhibited biological activity contained at least one hybridizing clone which shared a common restriction cleavage map with clone 2A-E3. The frequency of hybridizing clones among the $10^4$ which were picked suggests a frequency of approximately 0.2% in the total library. Of the hybridizing clones which were tested, approximately 90% expressed a functional protein.

E. Biological Activities of Culture Supernatants of COS 7 Monkey Cells Transfected with pcD-2A-E3

Supernatant from COS 7 cells transfected with pcD-2A-E3 was tested for TCGF activity on the murine helper T cell line HT-2, described by Watson in *J. Exp. Med.*, Vol. 150, pg. 1510 (1979). Proliferation of the HT-2 cells, as determined by the calorimetric assay of Mosmann (cited above), was used as a measure of TCGF activity (degree of proliferation being correlated to optical density (OD) between 570–630 nm). FIG. 3A illustrates the relative TCGF activities at various dilutions of (i) supernatant from COS 7 cells transfected with pcD-2A-E3 (curve 1), (ii) supernatant from Cl.Ly1$^+$2$^-$/9 cultures (curve 2), (iii) supernatant from COS 7 cells transfected with a pcD plasmid carrying IL-2 cDNA (curve 3), and (iv) supernatant from COS 7 cells transfected with a pcD plasmid containing no cDNA insert (i.e. a "mock" transfection) (curve 4).

Figure 3B:
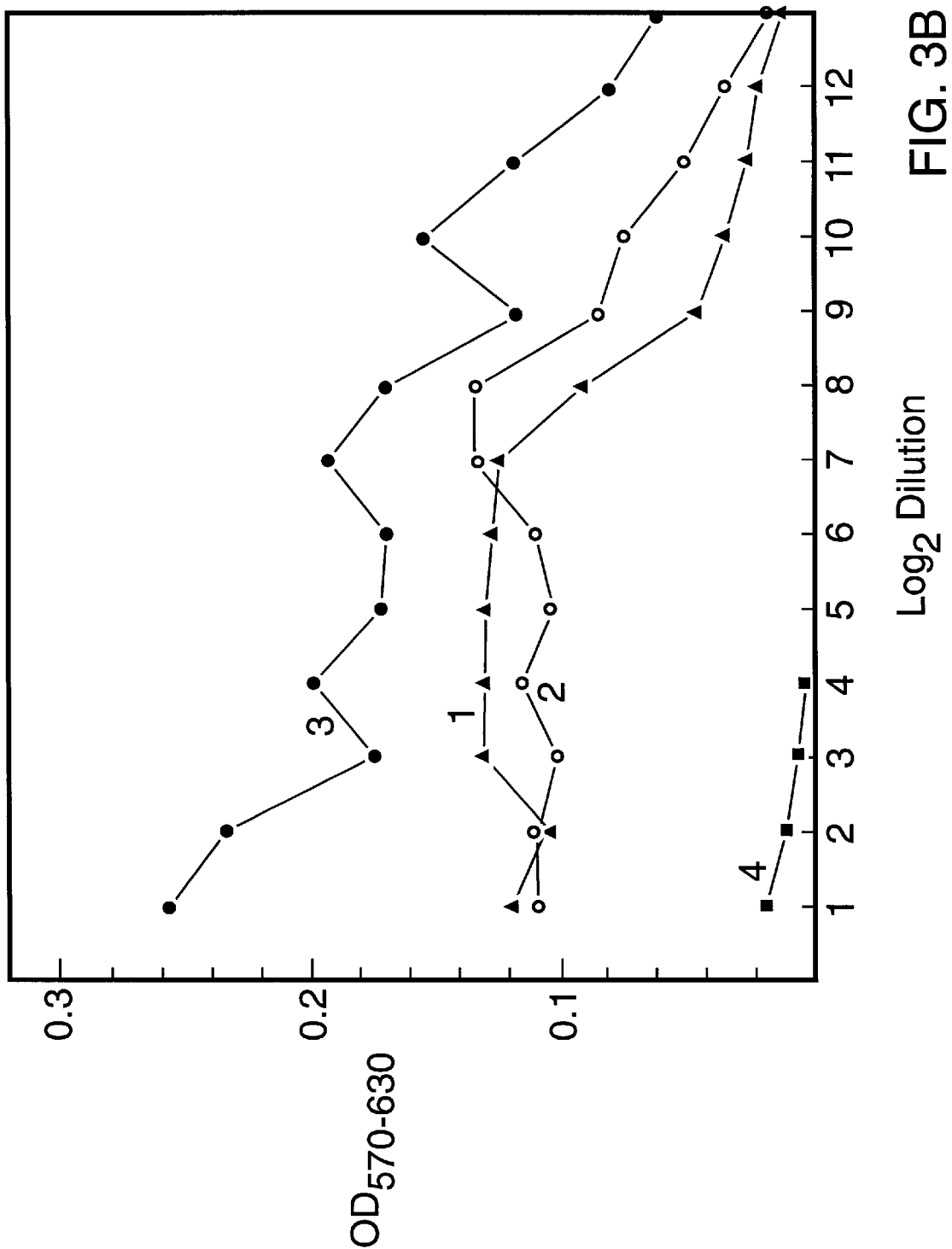
FIG. 3B illustrates relative MCGF activities (over a range of dilutions) of various culture supernatants including one (curve 1) from pcD-2A-E3 transfected COS 7 cells.

Similarly, supernatants from pcD-2A-E3 transfected COS 7 cells were tested for MCGF activity on MC/9 cells, again using the colorimetric assay of Mosmann to measure MC/9 proliferation. FIG. 3B illustrates relative MCGF activity of (i) supernatant from COS 7 cells transfected with pcD-2A-E3 (curve 1), (ii) supernatant from COS 7 cells transfected with a pcD plasmid carrying IL-3 cDNA (curve 2), (iii) supernatant from Cl.Ly1$^+$2$^-$/9 cells (curve 3), and (iv) supernatant from mock transfected COS 7 cells (curve 4).

Figure 3C:
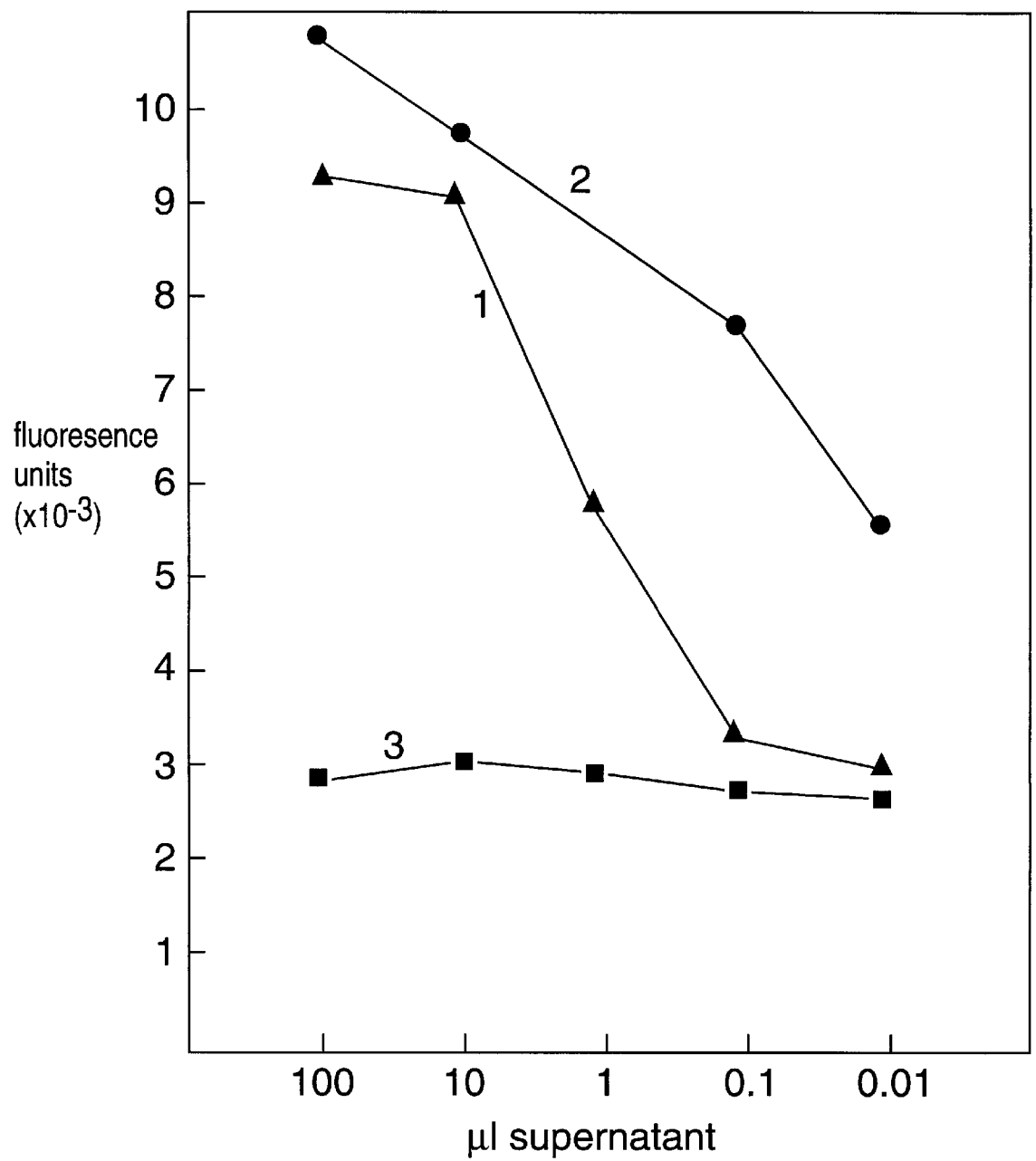
FIG. 3C illustrates the relative degrees of Ia induction produced by the indicated amounts of supernatant from pcD-2A-E3 transfected COS 7 cells (curve 1), Cl.Ly1$^{+}$2$^{-}$/9 cells (curve 2), and mock transfected COS 7 cells (curve 3).

FIG. 3C illustrates the results of an Ia induction assay conducted on (i) supernatant of COS 7 cells transfected with pcD-2-E3 (curve 1), (ii) supernatants of Cl.Ly1$^+$2$^-$/9 cells (curve 2), and (iii) supernatants of mock transfected COS 7 cells (curve 3). The Ia induction assay was carried out as described by Roehm et al. (cited above). Several DBA/2 mice (2–3 months old) were sacrificed and the spleens obtained surgically. The erythrocytes were lysed by hypotonic shock using 0.87% ammonium chloride. Then the T-cells were lysed by using cytotoxic monoclonal antibodies directed against T-cell-specific surface markers (Thy-1, Lyt-1 and Lyt-2) followed by incubation in rabbit complement. The dead cells were then removed using ficoll-hypaque density gradients. Adherent cells had been removed previously by adherence to plastic petri dishes at 37° C. At this time the cells were washed, counted and scored for viability. Approximately one million cells were incubated in 0.5 ml of tissue culture medium (RPMI 1640 or Minimal essential medium-MEM/Earle's salts) (Gibco) supplemented with 10% fetal calf serum, 2-mercaptoethanol and various antibiotics (penicillin, streptomycin and gentamicin). In experiments where the positive control consisted of supernatants from T-cells induced with the T-cell mitogen Concanavalin A, 10 mg/ml (final concentration) of alpha-methyl mannoside was added to neutralize the mitogen. After 24 hours incubation, the cells were harvested and prepared for staining with anti-I-A$^d$ or anti-I-A$^{bd}$ monoclonal antibodies. These antibodies were used as first stage antibodies conjugated to either the hapten N.I.P. or biotin. The staining was then completed by incubating the cells with fluoresceinated second-stage reagents (either anti-NIP antibodies or avidin). The intensity of fluorescence staining was then determined using either a fluorescence-activated cell sorter (Becton-Dickinson, Mountain View, Calif.) or a Cytofluorograph (Ortho Diagnostics, Cambridge, Mass.). Fluorescence units in FIG. 3C are calculated by multiplying the percentage of positive cells in each sample by the intensity of fluorescent staining.

Figure 3D:
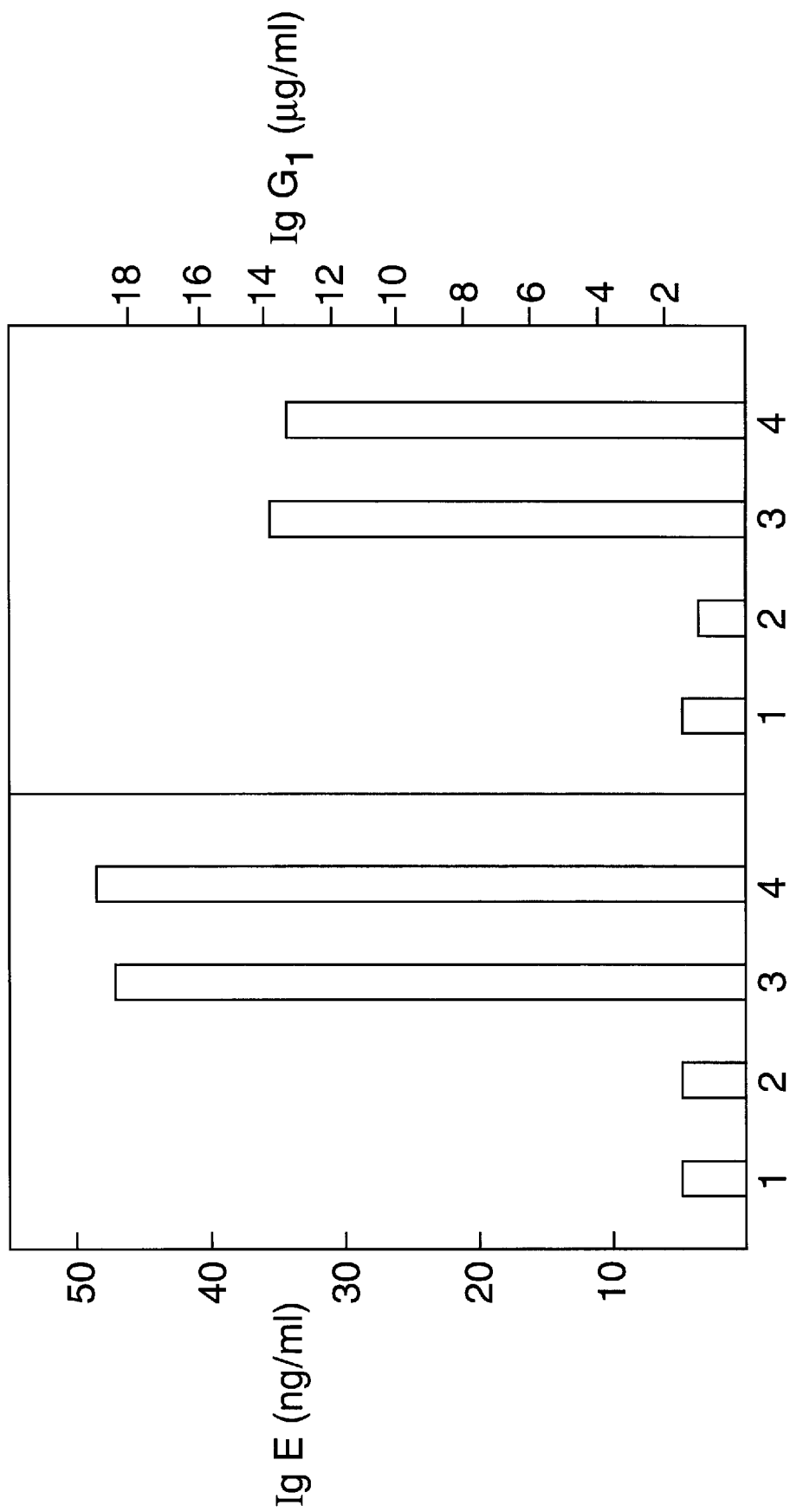
FIG. 3D graphically illustrates the extent of IgE and IgG$_1$ induction by supernatants from pcD-2A-E3 transfected COS 7 cells and various controls in T cell-depleted mouse spleen cells.

FIG. 3D graphically illustrates the degrees by which IgE and IgG$_1$ production are induced in T cell depleted mouse spleen cells by (i) COS 7 medium alone (bar 1), (ii) 20% supernatant from mock transfected COS 7 cells (bar 2), (iii) 10% supernatant from Cl.Ly1$^+$2$^-$/9 cells plus 20% supernatant from mock transfected COS 7 cells (bar 3), and (iv) 20% supernatant from pcD-2A-E3 transfected COS 7 cells (bar 4). Levels of IgE and IgG$_1$ were determined by the isotype-specific ELISA described above.

Murine IL-4 was found to enhance the MCGF activity of IL-3 in MC/9 cells, Smith and Rennick, *Proc. Natl. Acad. Sci.*, Vol. 83, pgs. 1857–1861 (1986). And Murine IL-4 was found to enhance GM-CSF stimulated proliferation of the IL-3 dependent cell line, NFS-60, described by Holmes et al., in *Proc. Natl. Acad. Sci.*, Vol. 82, pgs. 6687–6691 (1985).

F. Structure of pcD-2A-E3 and Nucleotide Sequence of Its cDNA Insert

Figure 2B:
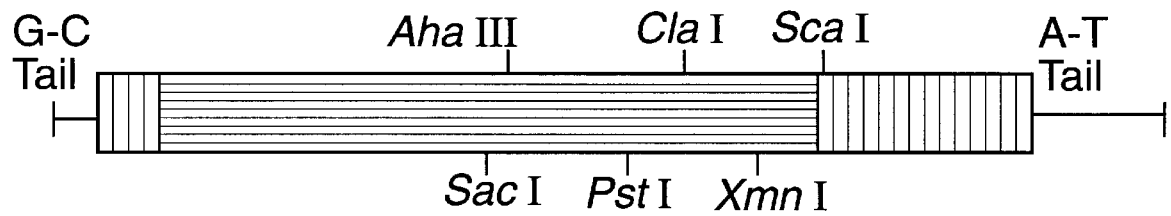
FIG. 2B is a restriction endonuclease cleavage map of the insert of vector pcD-2A-E3.
Figure 2C:
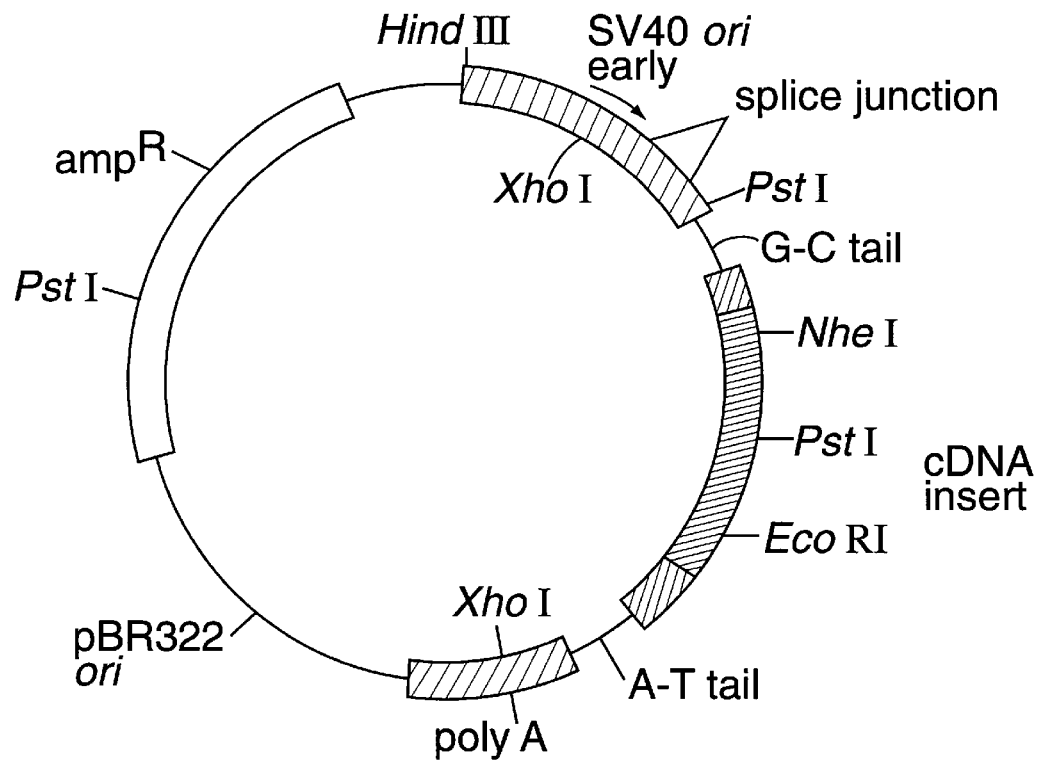
FIG. 2C is a map of vector pcD-46, the insert of which codes human IL-4.

The structure of pcD-2A-E3 is illustrated diagramatically in FIG. 2A, and an expanded restriction map of its insert is illustrated in FIG. 2B. The insert was sequenced using both the Maxam and Gilbert approach (*Methods in Enzymology*, Vol. 65, pgs. 499–560 (1980)) and the Sanger approach (*Proc. Natl. Acad. Sci.*, Vol. 74, pgs. 5463–5467 (1977)). The sequence is illustrated in FIG. 1A, along with the deduced amino acid sequence for the longest open reading frame in-phase with the first ATG start codon. The single long open reading frame in the mouse 2A-E3 cDNA clone consists of 140 amino acid residues. Because this lymphokine is a secreted protein, a hydrophobic leader sequence would be expected to precede the sequence for the mature secreted form of the protein. Analysis of the hydrophobicity of the polypeptide and comparison with a proposed consensus sequence for the processing of signal peptides (Perlman et al., *J. Mol. Biol.*, Vol. 167, pgs. 391–409 (1983)) suggest that cleavage of the precursor polypeptide would occur following the serine residue at amino acid position 20 in FIG. 1A. Grabstein et al., *J. Exp. Med.*, Vol. 163, pgs. 1405–1414 (1986), has confirmed that the N-terminal sequence of secreted murine IL-4 begins at the position 21 His of FIG. 1A.

Example II

Preparation of Human IL-4 Via a Murine cDNA Probe to a Human Helper T Cell cDNA Library and Transient Expression in COS 7 Monkey Cells and Mouse L Cells cDNA clones coding for IL-4 were isolated from cDNA libraries constructed from an induced human helper T cell, 2F1, and induced human peripheral blood lymphocytes (PBLs) by way of a murine cDNA probe. Other human cell lines known to produce BCGF activity include variants of the CEM line, available from the ATCC under accession numbers CCL 119, CRL 8436, and TIB 195, and described by Foley et al., in *Cancer*, Vol. 18, pgs. 522–529 (1965), and by Ligler, in *Lymphokine Research*, Vol. 3, pgs. 183–191 (1984). The procedures used in this example are disclosed by Yokota et al., in *Proc. Natl. Acad. Sci.*, Vol. 83, pgs. 5894–5898 (1986) (in press), which is incorporated herein by reference.

A human helper T-cell clone, 2F1, and human PBLs were grown in Iscove's medium supplemented with 3% fetal calf serum. The 2F1 cells were activated with Con A (10 µg/ml) and PBL's were stimulated with 1 ng/ml PMA for 12 hr, after which ConA at 5 mg/ml was added. The cells were harvested 4 hr (2F1) or 10 hr (PBL's) after addition of Con A.

mRNA extraction and cDNA library construction were carried out as described in Example I. A PstI fragment was isolated from the mouse pcD-2A-E3 cDNA clone, labeled by nick translation (1–10$^8$ cpm/µg) and used to probe nitrocellulose filters containing plasmid DNA preparations from ten pools, each representing approximately 1–10$^3$ clones of 2F1 cDNA library. Low stringency hybridization conditions (overnight at 42° C.) were used: 6×SSPE (1×SSPE=180 mM NaCl/10 mM sodium phosphate, pH 7.4/1 mM EDTA) (Maniatis, T. et al., *Molecular Cloning: A Laboratory Manual* (Cold Spring Harbor Laboratory, New York, 1982)), 20% (vol/vol) formamide, 0.1% sodium dodecyl sulfate, yeast carrier tRNA at 100 µl. The filters were washed with 2×SSPE, 0.1% sodium dodecyl sulfate at 37° C.

Figure 2D:
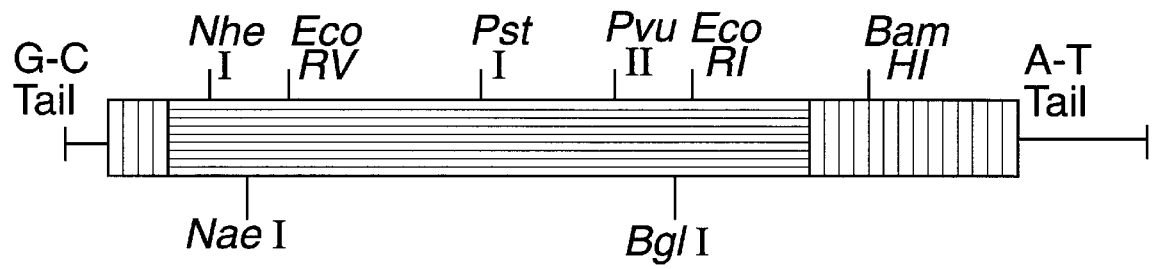
FIG. 2D is a restriction endonuclease cleavage map of the insert of vector pcD-46.

A single clone (pcD-46) was identified in one of the ten pools. Additional clones were obtained by screening the PBL cDNA libraries with a probe constructed from the NheI-EcoRI fragment of pcD-46 (illustrated in the restriction map of FIG. 2D). Analysis by restriction enzymes indicated that the PBL clones were identical in structure to pcD-46.

It was discovered that a guanidine-rich region in the 5', or upstream, direction from the coding region insert pcD-46 inhibited expression of the IL-4 polypeptide. Consequently, the insert of pcD-46 was recloned to remove the guanidine-rich region. The resulting clone is designated pcD-125. It was also discovered that expression was improved by transfecting mouse L cells with pcD-46.

The vector pcD-125 was formed as follows: pcD-46 was cleaved with Sau3A to isolate a fragment containing the 5' 162 nucleotides of the cDNA insert (eliminating the GC segment) and then the fragment was inserted into the BglII site of p101. The plasmid p101 was derived from pcD-mouse IL-3 (see, Yokota, T. et al., [1984] cited above) and is deleted for the sequence from the PstI site at the 5' end of the cDNA to a BglII site within the mouse IL-3 cDNA. A BglII site is included at the junction of the deleted sequence. The Sau3A fragment is fused to the SV40 promoter as in pcD-46, except for the GC stretch. The remainder of the human cDNA was then reconstructed with a HindIII/NheI fragment from pcD-46 which carries the 3' end of the cDNA, the SV40 poly A site and all of the pBR322 sequences of pcD-46.

Supernatants of the pcD-46 and pcD-125 transfected COS 7 and L cells were assayed for BCGF and TCGF activity. TCGF was assayed with an Epstein-Barr virus transformed human helper T cell line JL-EBV, and phytohemagglutinin (PHA) stimulated human peripheral blood lymphocytes (PBLs).

The human helper T-cell clone JL-EBV was stimulated with irradiated (4500 R) cells of a human EBV-transformed B-cell line, and subsequently maintained in RPMI 1640 medium containing 10% human AB serum, 50 micromolar 2-mercaptoethanol (2 ME) and recombinant human IL-2. Human PBLs were stimulated with PHA (20 microgram/ml) and maintained in RPMI 1640 containing 10% fetal calf serum, 50 micromolar 2 ME and recombinant human IL-2. Five to ten days after stimulation, JL-EBV cells or PHA blasts were used as targets in a two-day TCGF assay, using the Mosmann colorimetric method (described above) or in a three-day TCGF assay, using [$^3$H] thymidine incorporation.

Figure 4A:
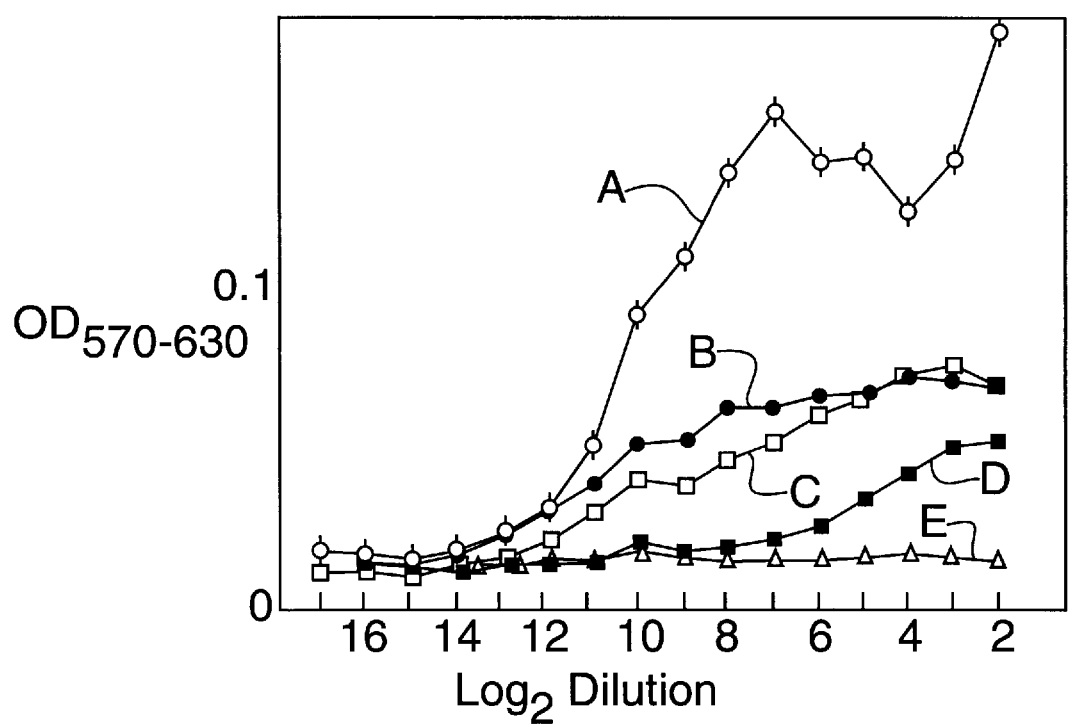
FIG. 4A illustrates the TCGF activities of several pcD-125 transfection supernatants and controls as measured by a colorimetric proliferation assay on the factor-dependent human helper T cell line, JL-EBV.
Figure 4B:
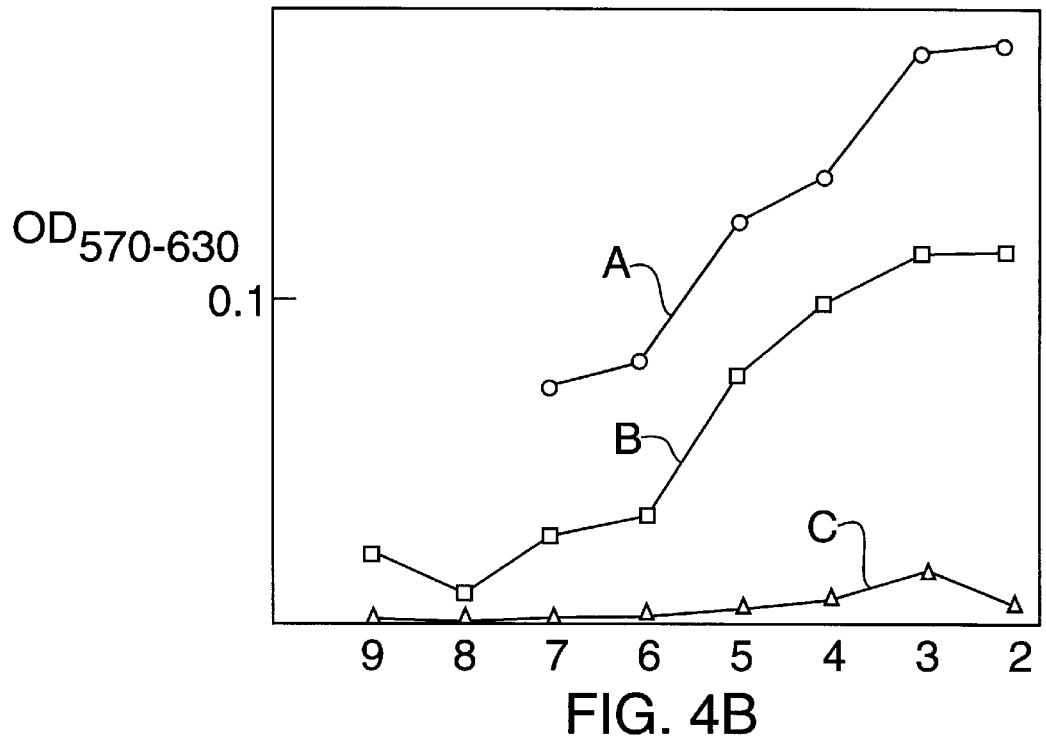
FIG. 4B illustrates the TCGF activities of a pcD-125 transfection supernatant and controls as measure by a calorimetric proliferation assay on PHA-stimulated peripheral blood lymphocytes.
Figure 4C:
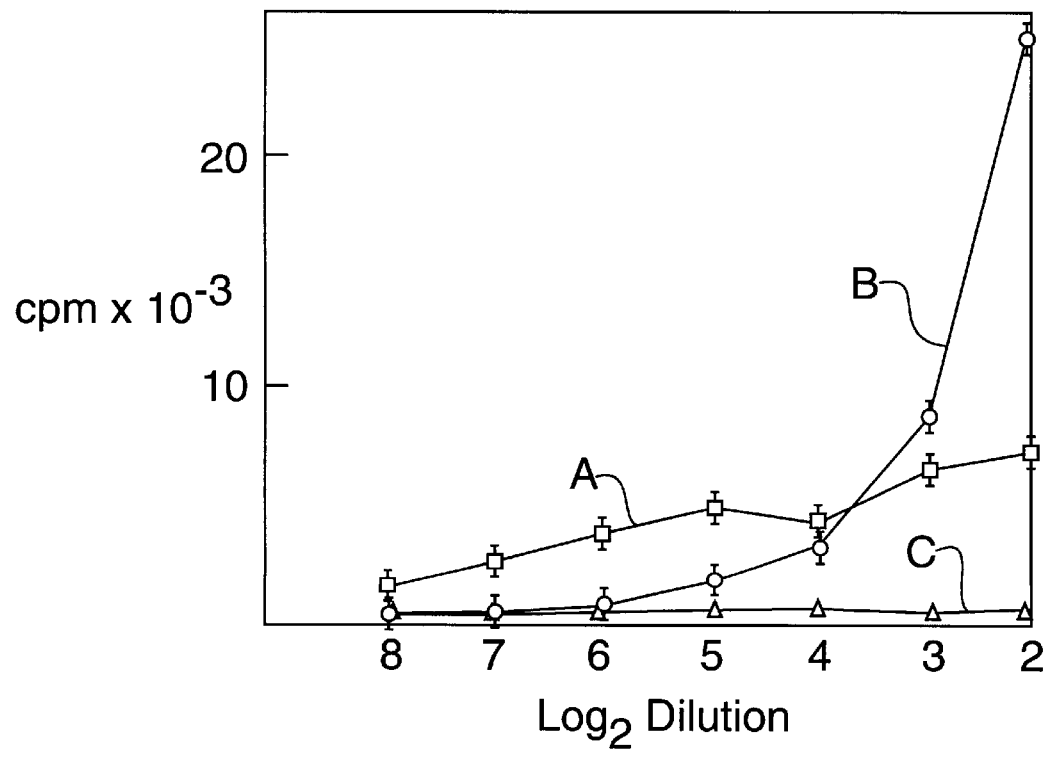
FIG. 4C illustrates the TCGF activities of a pcD-125 transfection supernatant and controls as measured by tritiated thymidine incorporation by PHA-stimulated peripheral blood lymphocytes.
Figure 5A:
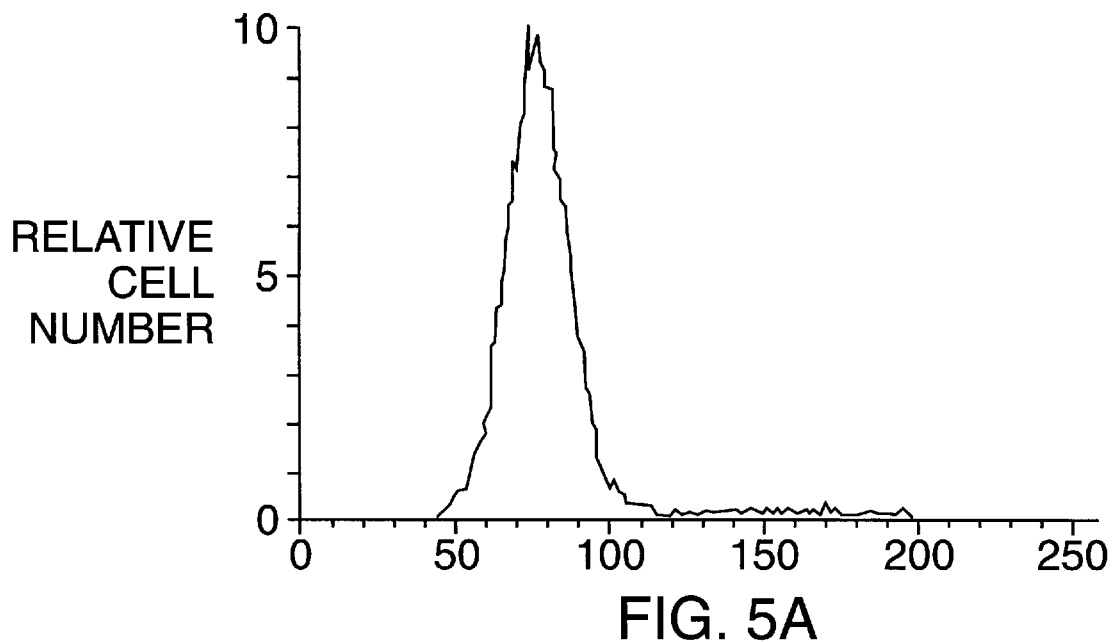
FIG. 5A is a histogram of cell frequency versus fluorescence intensity for a control population of stimulated human tonsilar B cells whose Fc-epsilon receptors have been fluorescently labeled.
Figure 5B:
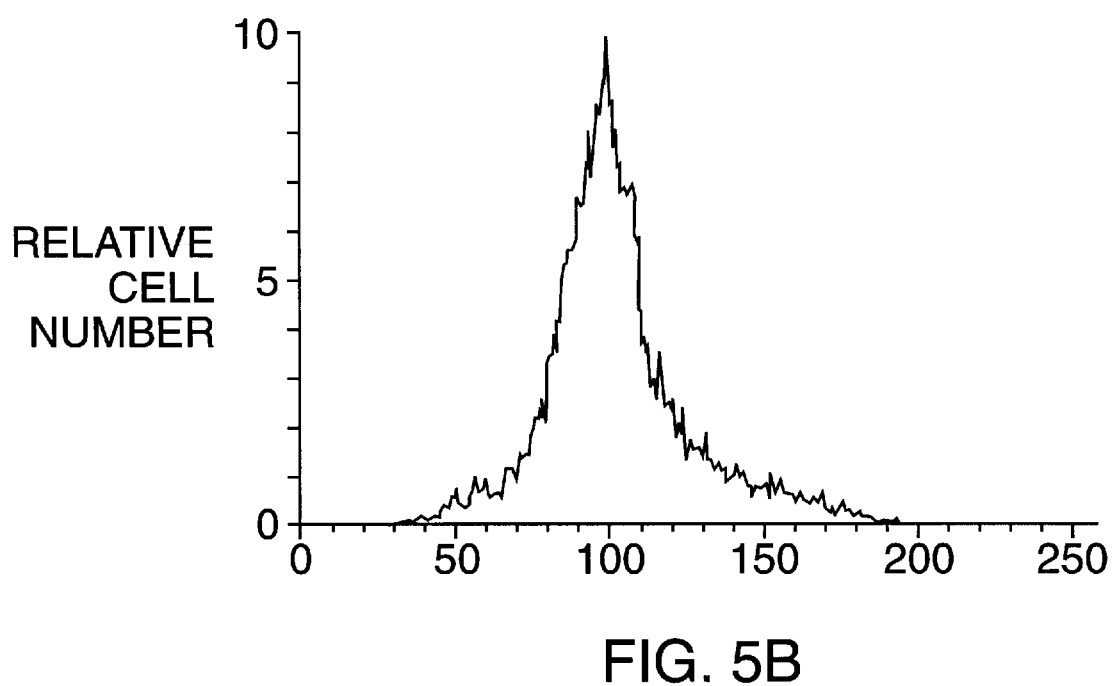
FIG. 5B is a histogram of cell frequency versus fluorescence intensity for a population of stimulated human tonsilar B cells which had been exposed to medium consisting of 0.1% supernatant from pcD-125 transfected COS 7 cells and whose Fc-epsilon receptors have been fluorescently labeled.
Figure 5C:
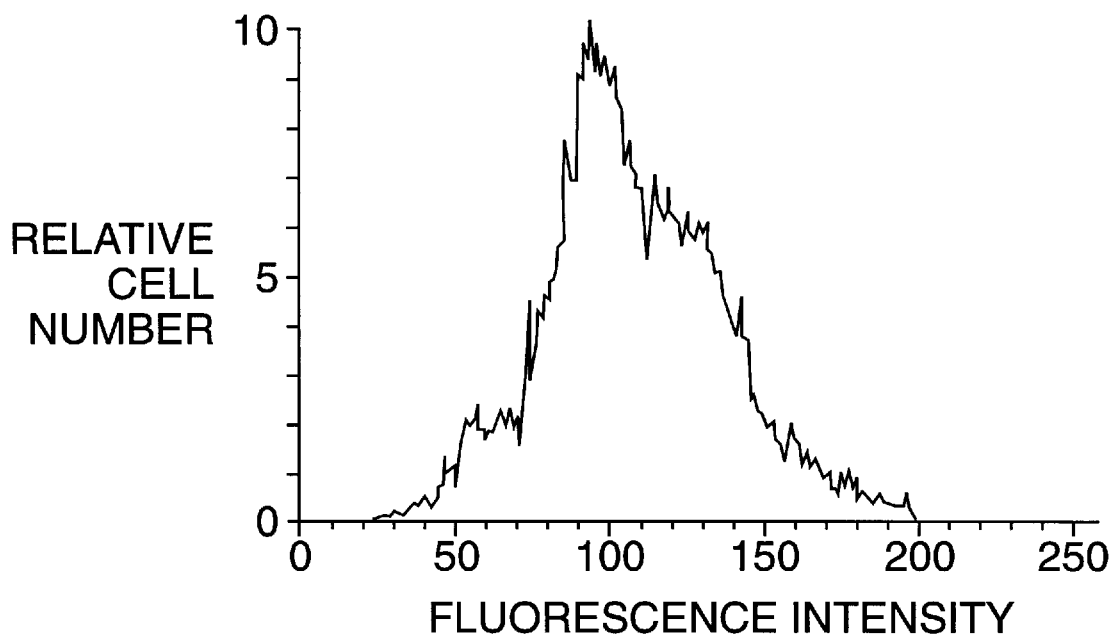
FIG. 5C is a histogram of cell frequency versus fluorescence intensity for a population of stimulated human tonsilar B cells which had been exposed to medium consisting of 1% supernatant from pcD-125 transfected COS 7 cells and whose Fc-epsilon receptors have been fluorescently labeled.
Figure 5D:
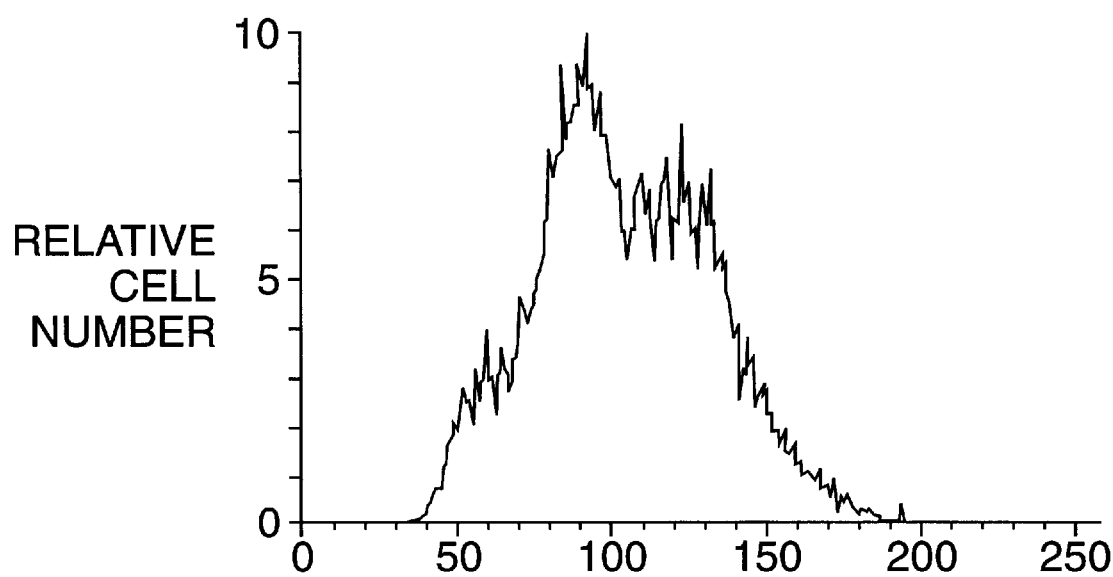
FIG. 5D is a histogram of cell frequency versus fluorescence intensity for a population of stimulated human tonsilar B cells which had been exposed to medium consisting of 10% supernatant from pcD-125 transfected COS 7 cells and whose Fc-epsilon receptors have been fluorescently labeled.

FIG. 4A illustrates the TCGF activities measured by JL-EBV cells (colorimetric assay) of (i) supernatant from COS 7 cells transfected with pcD plasmids expressing human IL-2 (curve A); (ii) supernatant from L cells transfected with pcD-125 (curve B); (iii) supernatant from COS 7 cells transfected with pcD-125 (curve C), (iv) supernatant from COS 7 cells transfected with pcD-46 (curve D), and (v) supernatant from mock transfected COS 7 cells (curve E). FIG. 4B illustrates the TCGF activities measured by PHA stimulated PBLs (colorimetric assay) of (i) supernatant from COS 7 cells transfected with pcD plasmids expressing human IL-2 (curve A), (ii) supernatant from COS 7 cells transfected with pcD-125 (curve B), and (iii) supernatant from mock transfected COS 7 cells (curve C). FIG. 4C illustrates the TCGF activities measured by PHA stimulated PBLs (tritiated thymidine incorporation assay) of (i) supernatant from COS 7 cells transfected with pcD-125 (curve A), (ii) supernatant from COS 7 cells transfected with pcD plasmids expressing human IL-2 (curve B), and (iii) supernatant from mock transfected COS 7 cells (curve C).

BCGF activity of various dilutions of pcD-125 transfection supernatants were compared with the BCGF activity of a BCGF ("commercial BCGF") described by Maizel et al., Proc. Natl. Acad. Sci., Vol. 79, pgs. 5998–6002 (1982), and commercially available from Cytokine Technology International (Buffalo, New York). Table IV illustrates the BCGF activities of various dilutions of COS 7 transfection supernatants on anti-IgM antibody preactivated B cells. B cells were prepared as described in the assay section above.

TABLE IV

Effect of the IL-4 cDNA transfection supernatants on anti-IgM-preactivated B cells

| % (vol/vol) of supernatants added | $^3$H-Thymidine Incorporation (cpm) | | | |
|---|---|---|---|---|
| | Mock-transfection | Clone 125 | Mock-transfection + 10% BCGF | Clone 125 + 10% BCGF |
| 0 | 278 | 278 | 1835 | 1835 |
| 0.2 | 189 | 144 | 1362 | 2303 |
| 1 | 323 | 1313 | 1699 | 3784 |
| 5 | 408 | 4314 | 1518 | 7921 |
| 15 | 397 | 4289 | 1093 | 8487 |

Table V illustrates the BCGF activities of various dilutions of COS 7 transfection supernatants on SAC preactivated B cells (prepared as described above)

TABLE V

Activity of the IL-4 cDNA transfection supernatants on SAC-preactivated B cells

| % (vol/vol) of supernatants added | $^3$H-Thymidine Incorporation (cpm) | | | |
|---|---|---|---|---|
| | Mock-transfection | Clone 125 | Mock-transfection + 10% BCGF | Clone 125 + 10% BCGF |
| 0 | 2237 | 2237 | 12,992 | 12,992 |
| 0.2 | 1789 | 2682 | 13,126 | 5,655 |
| 1 | 740 | 2374 | 13,714 | 6,765 |
| 5 | 1285 | 2826 | 5,848 | 10,023 |
| 15 | 1560 | 4701 | 10,128 | 10,924 |

Although the human IL-4 of the invention and commercial BCGF both display BCGF activity, Mehta et al., in J. Immunol., Vol. 135, pgs. 3298–3302 (1985), demonstrated that TCGF activity can be biochemically separated from the BCGF activity of commercial BCGF, indicating that the activities are caused by separate molecules. Thus, human IL-4 and commercial BCGF are different molecules because TCGF activity is inseparable from BCGF activity in human IL-4, using standard biochemical fractionation techniques.

Supernatants from COS-7 cells transfected with plasmids bearing the human IL-4 cDNA induce the proliferation of normal human T cells and the human T-cell clone JL-EBV, and activity that is similar to mouse IL-4. However, the maximum extent of proliferation of human T cells induced in response to human IL-4 is about half of that induced by human IL-2. The proliferation-inducing activity of IL-4 could not be inhibited by monoclonal antibodies against IL-2 or the IL-2 receptor when tested. These results suggest that IL-4 acts directly on T cells and not by way of the induction of IL-2 and that its activity is not mediated by the IL-2 receptor. The COS-human IL-4 supernatants also stimulate the proliferation of human B cells preactivated with optimal concentrations of anti-IgM antibodies coupled to beads and have additive proliferative capacity with commercial BCGF at saturation levels of the BCGF assay. This suggests that human IL-4 and commercial BCGF operate on B cells by different routes, e.g. possibly by different sets of receptors. The supernatants did not significantly induce proliferation of B cells preactivated with SAC, whereas commercial BCGF purified from supernatants of PBL cultures stimulated with PHA strongly induced the proliferation of SAC-preactivated human B cells. These results further indicate that the human IL-4 cDNA encodes a BCGF activity that is distinct from that present in the commercial BCGF.

Supernatant of pcD-125 transfected COS 7 cells was also tested for its ability to induce Fc-epsilon receptors on tonsilar B cells. Human tonsil cells were dispersed into a single cell suspension using standard techniques. The B cell population was enriched using the protocol described above, and the enriched cells were stimulated with anti-IgM antibody for 24 hours in culture medium at 37° C. Fc-epsilon receptor bearing cells were assayed by a Becton Dickinson FACS IV cell sorter using a fluorescently labeled monoclonal antibody specific for the receptor using the technique disclosed by Bonnefoy et al., in J. Immunol. Meth., Vol. 88, pgs. 25–32 (1986). FIGS. 5A–5D are histograms illustrating cell frequency (ordinate) versus fluorescent intensity (abscissa). Fluorescence intensity is proportional to the number of Fc-epsilon receptors present on a cell. In all the Figures the cells have been stimulated with anti-IgM. FIGS. 5A through 5D correspond to exposures to media consisting of 0%, 0.1%, 1%, and 10% supernatant from pcD-125 transfected COS 7 cells.

The DNA sequence of the cDNA insert of clone #46 was determined and is shown in FIG. 1B. The cDNA insert is 615 bp long, excluding the poly(A) tail. There is a single open reading frame, with the first ATG codon located at 64 nucleotides from the 5' end followed by 153 codons ending with the termination codon TAG at nucleotide positions 523–525. The N-terminal segment of the predicted polypeptide is hydrophobic, as would be expected for a secreted protein.

A comparison between the coding regions of a human and a mouse cDNA of the present invention revealed that the regions of the human cDNA coding sequence in pcD-46 covered by amino acid positions 1-90 and 129-149 share approximately 50% homology with the corresponding regions of the mouse cDNA (2A-E3) coding sequence. These regions, and 5' and 3' untranslated regions, share about 70% homology between the two cDNA sequences from the different species, whereas the region covered by amino acids 91-128 of the human protein shares very limited homology with the corresponding mouse region. In all, six of the seven cysteine residues in the human protein are conserved in the related mouse protein. Some amino acid sequence homology exists between a native form of a human polypeptide of the present invention and mouse IL-3. Amino acid residues 7-16 and 120-127 are 50% and 55% homologous, respectively, to residues 16-27 and 41-49 of the mouse IL-3 precursor polypeptide (Yokota, T. et al., Proc. Natl. Acad. Sci. U.S.A. 81:1070–1074 [1984]).

As described more fully below, human IL-4 purified from pcD-125 transfected COS 7 supernatants was found to be the 129 amino acid polypeptide having the sequence illustrated by FIG. 1C.

Example III
Enhanced Expression of Human IL-4 in COS 7 Monkey cells by Using an Epstein-Barr Virus (EBV) Derived Vector Containing an RSV-LTR Promoter A 10–20 fold enhancement of human IL-4 expression was obtained by recloning the XhoI fragment of pcD-125 into an EBV-derived vector containing a Rous sarcoma virus long terminal repeat (RSV-LTR) promoter. The EBV-derived vector and the RSV-LTR promoter are described in the following references, which are incorporated by reference: Gorman et al., *Proc. Nat. Acad. Sci.*, Vol. 79, pgs. 6777–6781 (1982); and Yates et al., *Nature*, Vol. 313, pgs. 812–815 (1985).

A HindIII/XhoI fragment containing the RSV-LTR promoter was isolated from a pcD plasmid previously constructed from the RSV-LTR containing AccI/HindIII fragment described by Gorman et al. (cited above) and a commercially available pcD vector (e.g. Pharmacia). The above HindIII/XhoI fragment and a HindIII/XhoI fragment from a pL1 plasmid (Pharmacia) containing an SV40 origin of replication (ori) are spliced into plasmid pcDV1 (available from Pharmacia), the orientation of the SV40 ori region not being critical. Between an AatII site and an NdeI site, the resulting pcD vector contains in sequence (from the AatII site) an SV40 ori region, an RSV-LTR promoter, and the SV40 polyA region. After the XhoI fragment of pcD-125 is isolated and inserted into the XhoI site of the just constructed pcD vector, the unique AatII and NdeI sites on the vector are converted into SalI sites using standard techniques. Briefly, the pcD vector is digested with AatII and NdeI, the IL-4 containing fragment is isolated, and the isolated fragment is treated with T4 DNA polymerase in the presence of appropriate concentrations of the nucleoside triphosphates. The 5'→3' DNA polymerase activity of T4 DNA polymerase fills in the 5' protruding ends of the restriction cuts, and the 3'→5' exonuclease activity of T4 DNA polymerase digests the 3' protruding ends of the restriction cuts to leave a blunt ended fragment, to which kinased SalI linkers (New England Biolabs) are ligated using T4 DNA ligase.

Figure 11:
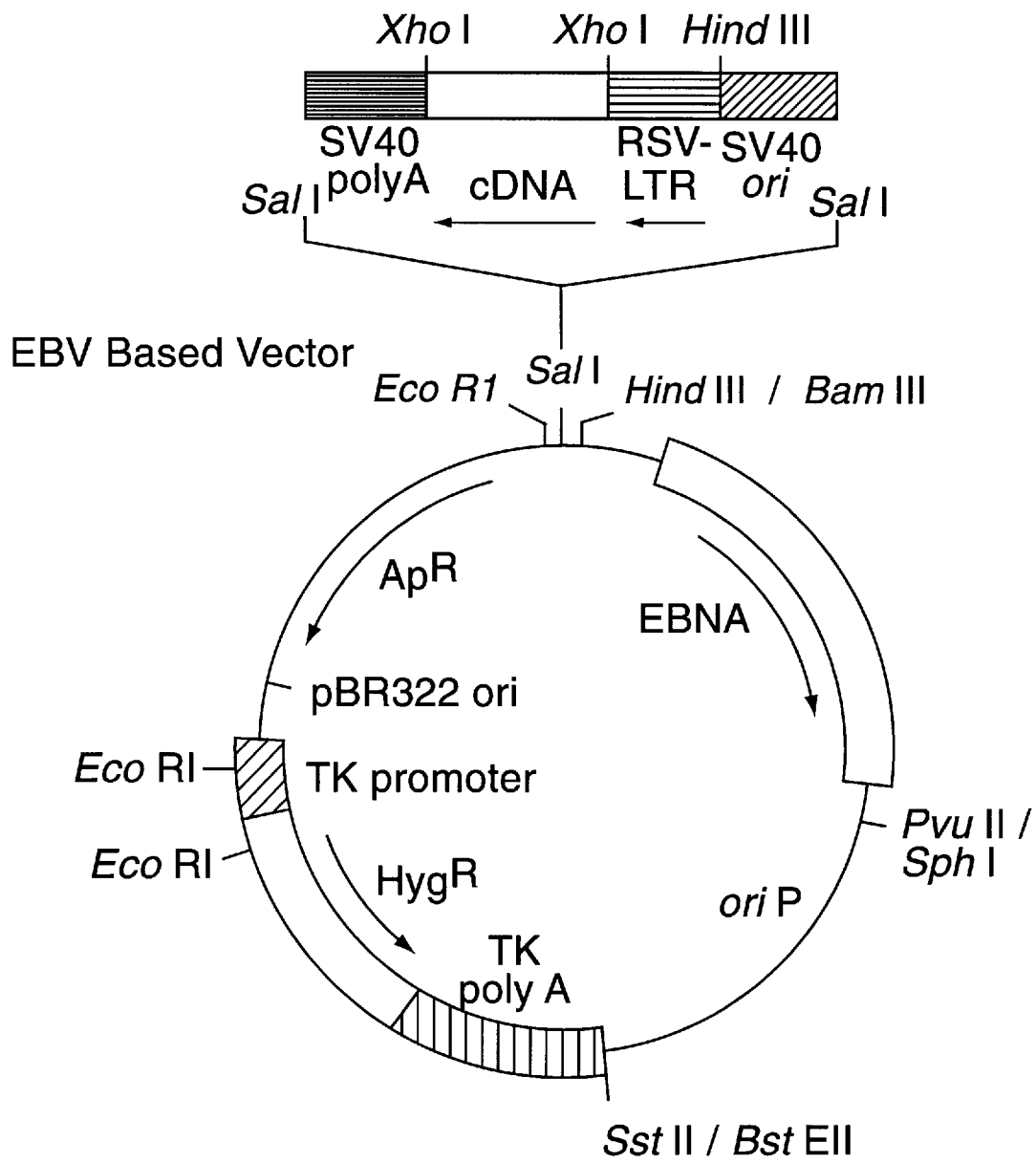
FIG. 11 is a construction map of plasmid pEBV-178 containing human IL-4 cDNA.

The above SalI fragment (illustrated in FIG. 11) is inserted in the EBV-derived vector p201 described by Yates et al. (cited above) at the location of a unique ClaI site, which had been converted to a SalI site using standard techniques. Briefly, p201 (illustrated in FIG. 11) is digested with ClaI and treated with DNA polymerase I (Klenow fragment) and appropriate concentrations of nucleoside triphosphates. This procedure fills in the protruding ends of the ClaI cut to leave a blunt ended fragment. Next, the blunt ends are ligated to a kinased SalI linker. The resulting EBV-derived vector containing the RSV-LTR promoter and human IL-4 cDNA insert is referred to herein as pEBV-178.

pEBV-178 was transfected into COS 7 cells using standard techniques and the culture supernatants were assayed for TCGF activity as a measure of IL-4 expression.

Example IV
Expression of Native Human IL-4 and Mutein $IS^0$ (Ala-Glu-Phe) in *E. coli*

Two vectors containing human IL-4 cDNA inserts were constructed for expression of human IL-4 in *E. coli*: a pIN-III secretion vector which contains the signal peptide sequence of the ompA protein ("pIN-III-ompA2"), and a pUC12 plasmid containing a trpP promoter and an adjacent ribosome binding site (RBS) region ("TRPC11").

A. pIN-III-ompA2

Two vectors were constructed using the pIN-III-ompA2 plasmid, which is described by Ghrayeb et al., in *EMBO Journal*, Vol. 3, pgs. 2437–2442 (1984); and Masui et al., in *Biotechnology*, Vol. 2, pgs. 81–85 (1984). Accordingly, these references are incorporated by reference.

The first vector, designated pIN-III-ompA2(1), was constructed by ligating, in series, the EcoRI/BAMHI digested pIN-III-ompA2 plasmid, a synthetic linker, and the BamHI/EcoRV fragment of pcD-125. The synthetic linker used in this construction resulted in the secretion of a biologically active IL-4 polypeptide having the three extra N-terminal amino acids Ala-Glu-Phe- (i.e. mutein $IL^0$(Ala-Glu-Phe) was secreted). The synthetic linker consisted of the following sequences of nucleotides:

```
AA  TTC  CAC  AAG  TGC  GAT
    G    GTG  TTC  ACG  CTA
```

EcoRI/BamHI digested pIN-III-ompA2 and the BamHI/EcoRV fragment of pcD-125 were mixed in a standard ligation solution (e.g. Maniatis et al., cited above) containing 0.1 micromolar of the synthetic linker. *E. coli* strain Ab1899 was infected by the pIN-III-ompA2(1) plasmid and transformants were selected by colony hybridization using a $^{32}$P-labeled IL-4 cDNA probe. Human IL-4 extracts for assaying were obtained as follows. After sonication, the bacterial cultures were centrifuged, and the supernatant removed from the pellet. The pellet was treated with 1% SDS, 2 mM dithiothreitol, and 6M guanidine. The material was recentrifuged, the supernatant discarded, and the pellet treated at 45° C. with 3% SDS and 2 mM dithiothreitol. The material was again centrifuged, and the supernatant assayed by SDS-PAGE.

pIN-III-ompA(2) was constructed so that the native human IL-4 would be expressed. The three amino acid addition in the pIN-III-ompA(1) construction was eliminated by site-specific mutagenesis of the ompA signal peptide sequence of pIN-III-ompA2. The site-specific mutagenesis was carried out as disclosed by Zoller and Smith (cited above). Briefly, the XbaI/BamHI fragment of pIN-III-ompA2 containing the coding sequence for the ompA signal peptide (see FIG. 1 in Ghrayeb et al., cited above) was purified, mixed with purified XbaI/BamHI digested replicating form (RF) of M13mp19, ligated, transfected into *E. coli* K-12 JM101, and plated. A clear plaque in the presence of IPTG and X-gal was selected, propagated, and single stranded DNAs were prepared, e.g. according to the procedures disclosed by Messing, in *Method in Enzymology*, Vol. 101 (Academic Press, New York, 1983). Separately, the following oligonucleotide primer (23-mer) containing the indicated base substitutions (boxed) was synthesized and phosphorylated.

5'- GGAATTCAGAAGCT [TG] C [G] GCTAC -3'

This sequence introduces a second HindIII site in the signal peptide coding region of the mutated pIN-III-ompA2. The oligonucleotide primer was annealed to the M13mp19 RF containing the XbaI/BamHI fragment of pIN-III-ompA2, and treated with DNA polymerase in the presence of appropriate concentrations of nucleoside triphosphates. The resulting RFs were used to transfect JM101 *E. coli*, and mutant-containing plaques were screened by a labeled oligonucleotide probe. The sequence of the selected RF was confirmed by dideoxy sequencing using a universal M13 primer. The selected RF was propagated, isolated, digested with XbaI and BamHI, and the purified XbaI/BamHI fragment was inserted into an XbaI/BamHI digested pIN-III-ompA2. To form pIN-III-ompA2(2), the mutant pIN-III-ompA2 was propagated, purified, digested with HindIII and BamHI, and mixed with the BamHI/EcoRV fragment of pcD-125 in a standard ligation solution containing 0.1 micromolar of the following synthetic linker:

```
A   GCT   CAC   AAG   TGC   GAT
    GTG   TTC   ACG   CTA
```

*E. coli* strain Ab1899 was infected by the pIN-III-ompA2(2) plasmid and transformants were selected by colony hybridization using a $^{32}$P-labeled IL-4 cDNA probe. IL-4 extracts, prepared as described above, exhibited TCGF activity comparable to supernatants of pcD-125 COS7 cells.

B. TRPC11

The TRPC11 vector was constructed by ligating a synthetic consensus RBS fragment to ClaI linkers (ATGCAT) and by cloning the resulting fragments into ClaI restricted pMT11hc (which had been previously modified to contain the ClaI site). pMT11hc is a small (2.3 kilobase) high copy, AMP$^R$, TET$^S$ derivative of pBR322 that bears the πVX plasmid (described by Maniatis et al., cited above) EcoRI-HindIII polylinker region. It was modified to contain the ClaI site by restricting pMT11hc with EcoRI and BamHI, filling in the resulting sticky ends and ligating with ClaI linker (CATCGATG), thereby restoring the EcoRI and BamHI sites and replacing the SmaI site with a ClaI site.

Figure 12:
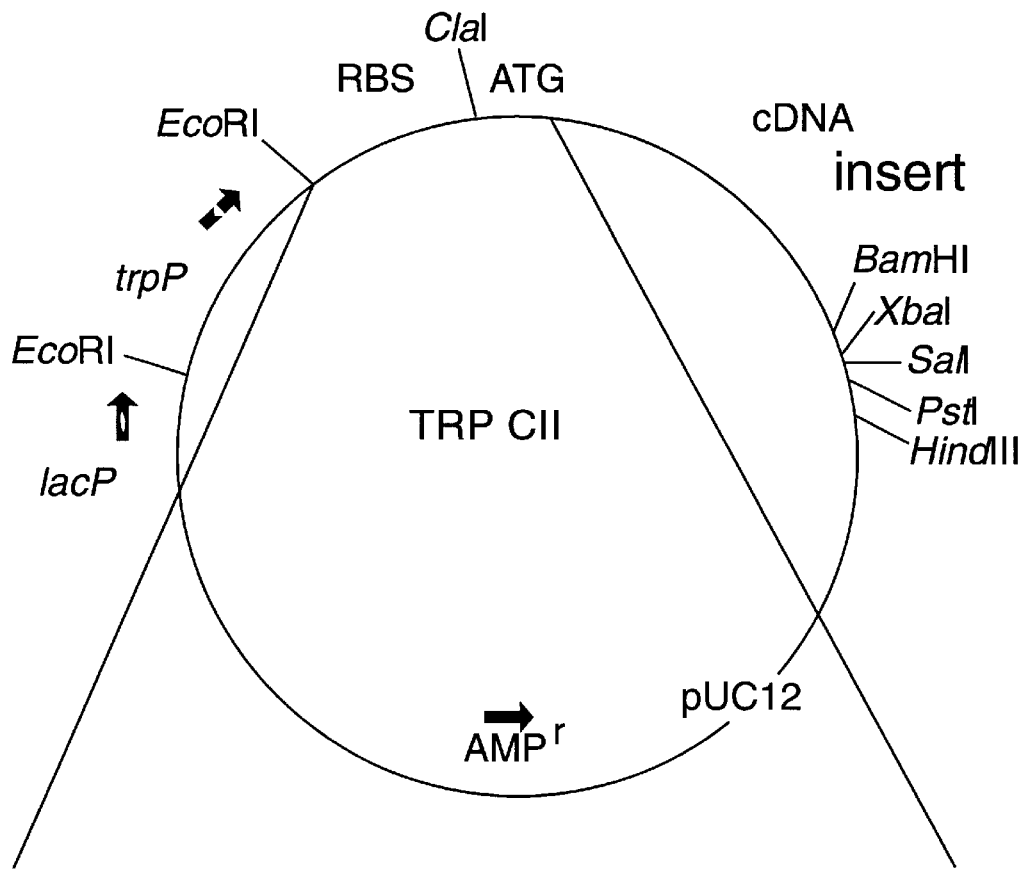
FIG. 12 is a construction map of plasmid TRPC11.

One transformant from the TRPC11 construction had a tandem RBS sequence flanked by ClaI sites. One of the ClaI sites and part of the second copy of the RBS sequence were removed by digesting this plasmid with PstI, treating with Bal31 nuclease, restricting with EcoRI and treating with T4 DNA polymerase in the presence of all four deoxynucleotide triphosphates. The resulting 30–40 bp fragments were recovered via PAGE and cloned into SmaI restricted pUC12. A 248 bp *E. coli* trpP-bearing EcoRI fragment derived from pKC101 (described by Nichols et al. in *Methods in Enzymology*, Vol. 101, pg. 155 (Academic Press, New York 1983)) was then cloned into the EcoRI site to complete the TRPC11 construction, which is illustrated in FIG. 12.

TRPC11 was employed as a vector for human IL-4 cDNA by first digesting it with ClaI and Bam HI, purifying it, and then mixing it with the EcoRV/BamHI fragment of pcD-125 in a standard ligation solution containing 0.1 micromolar of the following synthetic linker:

```
CG   ATG   CAC   AAG   TGC   GAT
     TAC   GTG   TTC   ACG   CTA
```

The insert-containing vector was selected as described above and propagated in *E. coli* K-12 strain JM101. IL-4 was extracted as follows. JM101 cells were sonicated in their culture medium and centrifuged. The pellet was resuspended in 4M guanidine and 2mM dithiothreitol, and again centrifuged. The supernatant was tested for biological activity and found to exhibit TCGF activity comparable to that of supernatants of pcD-125 transfected COS7 cells.

Example V
Preparation of Bovine IL-4 cDNAs Via Mouse and Human IL-4 cDNA Probes to a Bovine Helper T Cell cDNA Library and Transient Expression in COS 7 Monkey Cells cDNA clones coding for IL-4 are isolated from cDNA libraries constructed from induced bovine peripheral blood lymphocytes (PBLs) by way of a combined mouse and human cDNA probes. Alternative sources of bovine cDNAs include several bovine cell lines maintained in the ATCC's NBL animal line collection. Procedures are substantially identical to those described in Example II. Cells are harvested about 10 hours after induction by Con A. mRNA extraction and cDNA library construction are carried out as in Example II.

The mouse and human cDNA probes can be used together as a mixture or sequentially to detect bovine IL-4 cDNAs.

As in Example II, the PstI fragment is isolated from the mouse pcD-2A-E3 cDNA clone. Likewise the PstI fragment is isolated from the human pcD-125 cDNA clone. Several other fragments are also available to construct probes from. Either together or separately the isolated PstI fragments are labeled by nick translation (about $1 \times 10^8$ cpm/microgram) and are used to probe nitrocellulose filters containing plasmid DNA preparations from 10 pools, each representing about 1000 clones of the induced PBL cDNA library. Filter hybridization is carried out as in Example II. Positive scoring clones are identified and propagated.

Example VI
Expression of Native Human IL-4 and Muteins $\Delta^{1-4}$ and IS$^0$(Gly-Asn-Phe-Val-His-Gly) in *Saccharomyces cerevisiae*

Figure 13A:
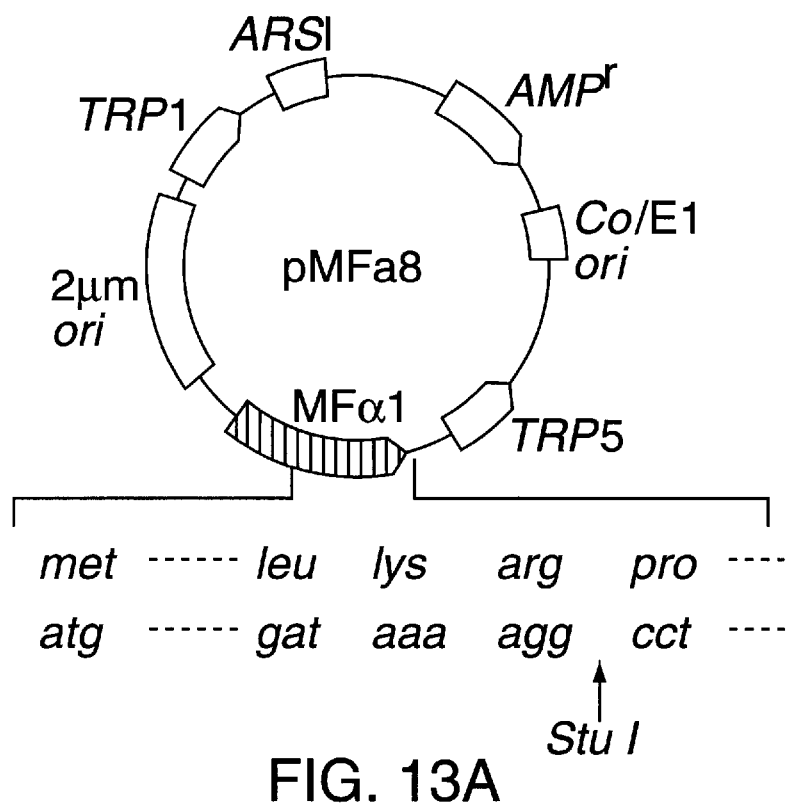
FIG. 13A is a construction map of plasmid pMF-alpha8.

Native human IL-4 cDNA and two mutants thereof were cloned into the plasmid pMF-alpha8 and expressed in the yeast Saccharomyces cerevisiae. The construction and application of pMF-alpha8 for expressing non-yeast proteins is described fully in Miyajima et al., *Gene*, Vol. 37, pgs. 155–161 (1985); and Miyajima et al., *EMBO Journal*, Vol. 5, pgs. 1193–1197 (1986), both of which are incorporated by reference. pMF-alpha8 is deposited with the American Type Culture Collection (Rockville, Md.) under accession number 40140, and a map of the plasmid is illustrated in FIG. 13A (designations in the figure are defined fully in Miyajima et al., *Gene*, cited above).

A. Human IL-4 Mutein $\Delta^{1-4}$

Figure 13B:
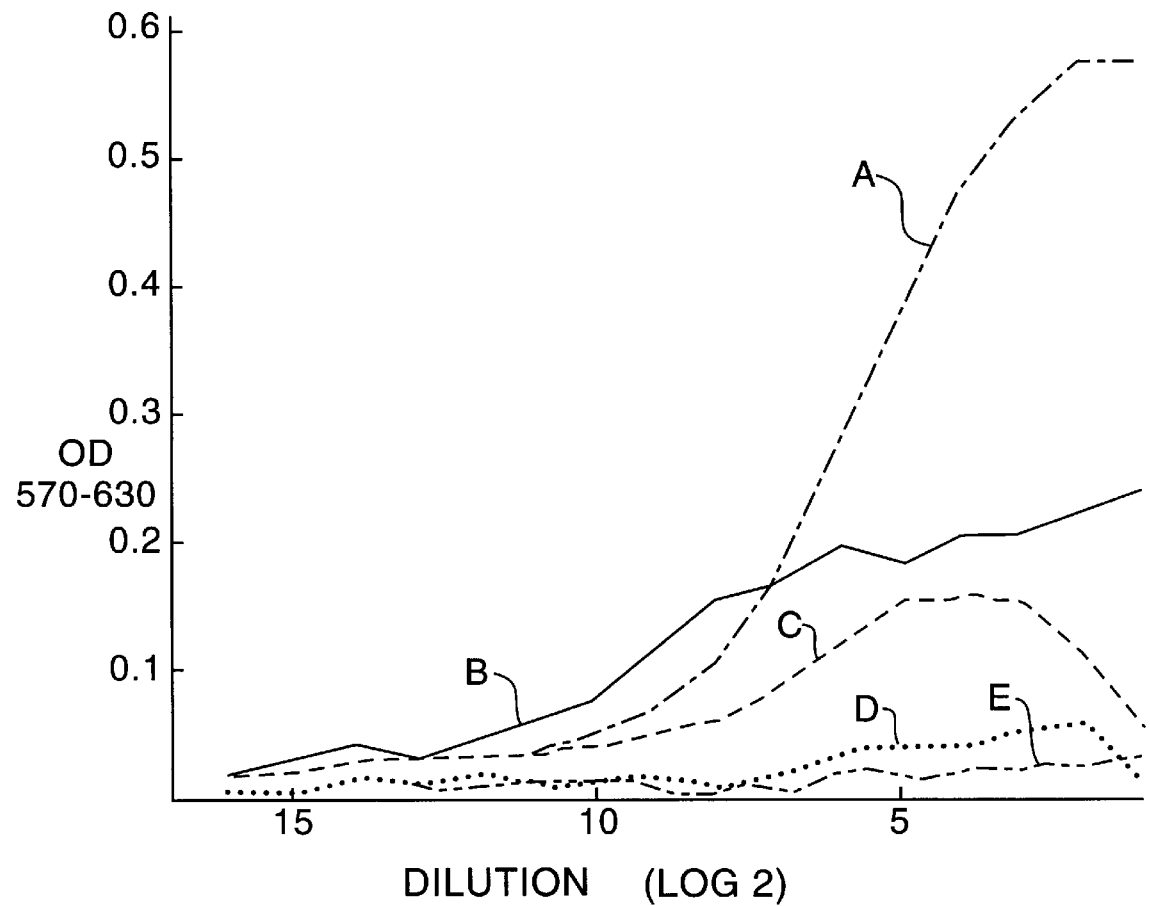
FIG. 13B illustrates the TCGF activities of several transfection supernatants from yeast cultures expressing native human IL-4 and various muteins thereof.

Plasmid pcD-125 was isolated and digested with EcoRV and BamHI. The EcoRV/BamHI fragment containing the human IL-4 cDNA was isolated, treated with DNA polymerase I (Klenow fragment) to fill in the BamHI cut, and kinased (i.e. phosphorylated). pMF-alpha8 was digested with StuI and combined with the kinased EcoRV/BamHI fragment of pcD-125 in a standard ligation solution to form plasmid phIL-4-2. phIL-4-2 was used to transform S. cerevisiae 20B-12 (MATalpha trp1-289 pep4-3), which was obtained from the Yeast Genetic Stock Center, University of California, Berkeley. Yeast cells were grown in synthetic medium containing 0.67% Yeast Nitrogen Base without amino acids, 2% glucose, and 0.5% Casamino acids (Difco). The yeast cells were transformed with the plasmids by the lithium acetate method of Ito et al., *J. Bacteriol.*, Vol. 153, pgs. 163–168 (1983), and transformants were selected in synthetic medium lacking tryptophan. Supernatant of a transformant culture was tested for TCGF activity. FIG. 13B (curve D) illustrates the TCGF activity of several dilutions of the supernatant from phIL-4-2 transformed yeast cells in comparison with other factors (Curve A—human IL-2, Curve B—supernatant from pcD-125 transfected COS 7 cells, and Curve C—supernatants from phIL-4-1 transformed yeast cells). Curve E illustrates the TCGF activity of supernatant from yeast that had been transformed with pMF-alpha8 lacking the IL-4 cDNA insert, i.e. the "mock" transformant.

B. Human IL-4 Mutein IS$^0$(Gly-Asn-Phe-Val-His-Gly).

The pMF-alpha8 insert for expression of mutein IL$^0$(Gly-Asn-Phe-Val-His-Gly) was prepared exactly as for mutein $\Delta^{1-4}$ except that the NaeI/BamHI fragment from pcD-125 was used. The resulting plasmid was designated phIL-4-1. Several dilutions of supernatant from phIL-4-1 transformed yeast cells were tested for TCGF activity. The results are illustrated by Curve C of FIG. 13B. The supernatants were also tested for BCGF activity on both anti-IgM and SAC activated B lymphocytes. The assays were performed as described above, and the results are given in Table VI.

TABLE VI

BCGF Activity of Supernantants of phIL-4-3 Transformed Yeast Cells

| % (vol/vol) of supernatants added | [³H]Thymidine Incorporation (cpm) | |
|---|---|---|
| | SAC activated B Lymphocytes | Anti-IgM Bead Activated B Lymphocytes |
| .0 | 3633 ± 1239 | 641 + 69 |
| 0.09 | 7610 ± 310 | 13221 ± 472 |
| 0.19 | 9235 ± 181 | — |
| 0.39 | 10639 ± 786 | 16681 ± 310 |
| 0.78 | 10372 ± 572 | 18090 ± 1248 |
| 1.56 | 9905 ± 328 | 17631 ± 1216 |
| 3.1211354±836 | 18766 ± 1179 | |
| 6.25 | 10481 ± 541 | 19810 ± 1349 |
| 12.5 | 9641 ± 30 | 18136 ± 1126 |
| 25. | 8253 ± 857 | 14750 ± 1125 |

C. Expression of Native Human IL-4 in Yeast cDNA coding for native human IL-4 was cloned into pMF-alpha8 by first inserting bases upstream of the N-terminal His codon to form a KpnI restriction site. After cleavage by KpnI and treatment by DNA polymerasei, the blunt ended IL-4 cDNA was inserted into the StuI site of pMF-alpha8. The KpnI site was formed by use of standard site-specific mutagenesis. Briefly, pcD-125 was digested with BamHI, the fragment containing the entire human IL-4 cDNA was isolated, and inserted into the BamHI site of M13mp8. Single stranded M13mp8 containing the insert was isolated and hybridized to the following synthetic oligonucleotide which served as a primer:

5' - TCCACGGA  CACAAGTG - 3'

The inserted nucleotides are boxed. The plasmid containing the mutated IL-4 cDNA was identified by an oligonucleotide probe, propagated, isolated, and treated with KnI and BamHI. The KnI/BamHI fragment was isolated, treated with DNA polymerase I (Klenow fragment) to generate blunt ends, kinased, and ligated with StuI digested pMF-alpha8. Yeast was transformed by the resulting pMF-alpha8 plasmids, designated phIL-4-3, as described above, and supernatants were tested for TCGF activity. The supernatants displayed TCGF activity comparable to that observed for supernatants of phIL-4-1 transformed yeast.

Figure 6B:
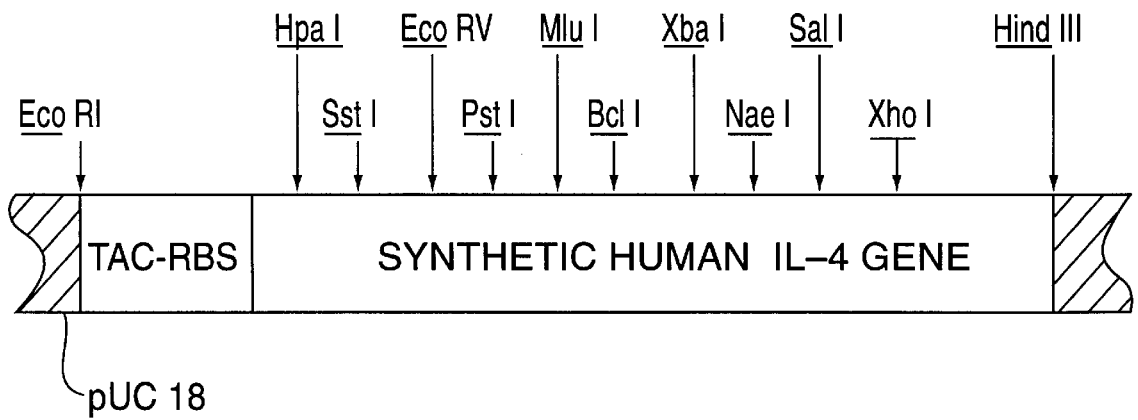
FIG. 6B is a restriction endonuclease cleavage map of a synthetic human IL-4 gene inserted in plasmid PUC18.

Example VII
Construction and Expression of a Synthetic Human IL-4 Gene in E. coli A synthetic human IL-4 gene is constructed which substantially comprises bacterial preferred codons and which includes a series of unique restriction endonuclease sites (referred to herein as "unique restriction sites") which permits rapid and convenient expression of a wide variety of human IL-4 muteins. The nucleotide sequence of the synthetic gene is illustrated in FIG. 6A. Unique restriction sites with respect to plasmid pUC18 are indicated in FIG. 6B. Techniques for constructing and expressing the synthetic gene of this example are standard in the art of molecular biology, e.g. Sproat and Gait, *Nucleic Acids Research*, Vol. 13, pgs. 2959–2977 (1985); Mullenbach et al., *J. Biol. Chem.*, Vol. 261, pgs. 719–722 (1986); Ferretti et al., *Proc. Natl. Acad. Sci.*, Vol. 83, pgs. 599–603 (1986); Wells et al., *Gene*, Vol. 34, pgs. 315–323 (1985); and Estell et al., *Science*, Vol. 233, pgs. 659–663 (1986). Sproat and Gait (cited above) and Ferretti et al. (cited above) are incorporated by reference as guides for applying the technique of gene synthesis. Briefly, the synthetic human IL-4 gene is assembled from a plurality of chemically synthesized double stranded DNA fragments. Base sequences of the synthetic gene are selected so that the assembled synthetic gene contains a series of unique restriction sites.

The series of unique restriction sites defines a series of segments which can be readily excised and replaced with segments having altered base sequences. The synthetic fragments are inserted either directly or after ligation with other fragments into a suitable vector, such as a pUC plasmid, or the like. The above-mentioned segments roughly correspond to the "cassettes" of Wells et al. (cited above). The synthetic fragments are synthesized using standard techniques, e.g. Gait, *Oligonucleotide Synthesis: A Practical Approach* (IRL Press, Oxford, UK, 1984). Preferably an automated synthesizer is employed, such as an Applied Biosystems, Inc. (Foster City, Calif.) model 380A. pUC plasmids and like vectors are commercially available, e.g. Pharmacia-PL, or Boehringer-Mannheim. Cloning and expression can be carried out in standard bacterial systems, for example *E. coli* K-12 strain JM101, JM103, or the like, described by Viera and Messing, in *Gene*, Vol. 19, pgs. 259–268 (1982).

Restriction endonuclease digestions and ligase reactions are performed using standard protocols, e.g. Maniatis et al., *Molecular Cloning: A Laboratory Manual* (Cold Spring Harbor Laboratory, New York, 1982).

The alkaline method (Maniatis et al., cited above) is used for small scale plasmid preparations. For large scale preparations a modification of the alkaline method is used in which an equal volume of isopropanol is used to precipitate nucleic acids from the cleared lysate. Precipitation with cold 2.5M ammonium acetate is used to remove RNA prior to cesium chloride equilibrium density centrifugation and detection with ethidium bromide.

For filter hybridizations Whatman 540 filter circles are used to lift colonies which are then lysed and fixed by successive treatments with 0.5M NaOH, 1.5M NaCl; 1M Tris.HCl pH8.0, 1.5M NaCl (2 min each); and heating at 80° C. (30 min). Hybridizations are in 6×SSPE, 20% formamide, 0.1% sodium dodecylsulphate (SDS), 100 μg/ml *E. coli* tRNA, 100 μg/ml Coomassie Brilliant Blue G-250 (Biorad) at 42° C. for 6 hrs using $^{32}$P-labelled (kinased) synthetic DNAs. (20×SSPE is prepared by dissolving 174 g of NaCl, 27.6 g of $NaH_2PO_4.H_2O$, and 7.4 g of EDTA in 800 ml of $H_2O$. pH is adjusted to 7.4 with NaOH, volume is adjusted to 1 liter, and sterilized by autoclaving).

Filters are washed twice (15 min, room temperature) with lxSSPE, 0.1% SDS. After autoradiography (Fuji RX film), positive colonies are located by aligning the regrown colonies with the blue-stained colonies on the filters.

DNA is sequenced by either the chemical degradation method of Maxam and Gilbert, *Methods in Enzymology*, Vol. 65, pg. 499 (1980), or by the dideoxy method, Sanger et al. *Proc. Natl. Acad. Sci.*, Vol. 74, pg. 5463 (1977). Templates for the dideoxy reactions are either single stranded DNAs of relevant regions recloned into M13mp vectors, e.g. Messing et al. *Nucleic Acids Res.*, Vol. 9, pg. 309 (1981), or double-Stranded DNA prepared by the minialkaline method and denatured with 0.2M NaOH (5 min, room temperature) and precipitated from 0.2M NaOH, 1.43M ammonium acetate by the addition of 2 volumes of ethanol. Dideoxy reactions are done at 42° C.

DNA is synthesized by phosphoramidite chemistry using Applied Biosystems 380A synthesizers. Synthesis, deprotection, cleavage and purification (7M urea PAGE, elution, DEAE-cellulose chromatography) are done as described in the 380A synthesizer manual. Complementary strands of synthetic DNAs to be cloned (400 ng each) are mixed and phosphorylated with polynucleotide kinase in a reaction volume of 50 μl. This DNA is ligated with 1 μg of vector DNA digested with appropriate restriction enzymes, and ligations are in a volume of 50 μl at room temperature for 4 to 12 hours. Conditions for phosphorylation, restriction enzyme digestions, polymerase reactions, and ligation have been described (Maniatis et al., cited above). Colonies are scored for lacZ+ (when desired) by plating on L agar supplemented with ampicillin, isopropyl-l-thio-beta-D-galactoside (IPTG) (0.4 mM) and 5-bromo-4-chloro-3-indolyl-beta-D-galactopyranoside (x-gal) (40 μg/ml).

The TAC-RBS vector is constructed by filling-in with DNA polymerase the single BamHI site of the tacP-bearing plasmid pDR540 (Pharmacia). This was then ligated to unphosphorylated synthetic oligonucleotides (Pharmacia) which form a double-stranded fragment encoding a consensus ribosome binding site (RBS, GTAAGGAGGTTTAAC). After ligation, the mixture was phosphorylated and religated with the SstI linker ATGAGCTCAT. This complex was then cleaved with SstI and EcoRI, and the 173 bp fragment isolated via polyacrylamide gel electrophoresis (PAGE) and cloned into EcoRI-SstI restricted pUC18 (Pharmacia) (as described below). The sequence of the RBS-ATG-polylinker regions of the final construction (called TAC-RBS) is shown in FIG. 8.

The synthetic human IL-4 gene is assembled into a pUC18 plasmid in six steps. At each step inserts free of deletions and/or inserts can be detected after cloning by maintaining the lacZ(α) gene of pUC18 in frame with the ATG start codon inserted in step 1. Clones containing deletion and/or insertion changes can be filtered out by scoring for blue colonies on L-ampicillin plates containing x-gal and IPTG. Alternatively, at each step sequences of inserts can be readily confirmed using a universal sequencing primer on small scale plasmid DNA preparations, e.g. available from Boehringer Mannheim.

In step 1 the TAC-RBS vector is digested with SstI, treated with T4 DNA polymerase (whose 3' exonuclease activity digests the 3' protruding strands of the SstI cuts to form blunt end fragments), and after deactivation of T4 DNA polymerase, treated with EcoRI to form a 173 base pair (bp) fragment containing the TAC-RBS region and having a blunt end at the ATG start codon and the EcoRI cut at the opposite end. Finally, the 173 bp TAC-RBS fragment is isolated.

In step 2 the isolated TAC-RBS fragment of step 1 is mixed with EcoRI/SstI digested plasmid pUC18 and synthetic fragment 1A/B, which as shown in FIG. 7A has a blunt end at its upstream terminus and a staggered end corresponding to an SstI cut at its downstream terminus. The fragments are ligated to form the pUC18 of step 2.

In step 3 synthetic fragments 2A/B and 3A/B (illustrated in FIGS. 7B and 7C) are mixed with SstI/BamHI digested pUC18 of step 2 (after amplification and purification) and ligated to form pUC18 of step 3. Note that the downstream terminus of fragment 2A/B contains extra bases which form the BamHI staggered end. These extra bases are cleaved in step 4. Also fragments 2A/B and 3A/B have complementary 9 residue single stranded ends which anneal upon mixture, leaving the upstream SstI cut of 2A/B and the downstream BamHI cut of 3A/B to ligate to the pUC18.

In step 4 MluI/XbaI digested pUC18 of step 3 (after amplification and purification) is repurified, mixed with synthetic fragment 4A/B (FIG. 7D), and ligated to form pUC18 of step 4.

In step 5 XbaI/SalI digested pUC18 of step 4 (after amplification and purification) is mixed with synthetic fragment of 5A/B (FIG. 7E) and ligated to form the pUC18 of step 5.

In step 6 SalI/HindIII digested pUC18 of step 5 (after amplification and purification) is mixed with synthetic fragment 6A/B (FIG. 7F) and ligated to form the final construction.

FIG. 6B is a cleavage map of the unique restriction sites present in the pUC18 construction just described. When the disclosed synthetic human IL-4 gene is used as an insert of pUC18 each pair of unique restriction sites defines a segment which can be readily excised and replaced with altered synthetic segments. The set of unique restriction sites includes EcoRI, HpaI, SacI (SstI), EcoRV, PstI, MluI, BclI, XbaI, NaeI, SalI, XhoI, and HindIII.

The pUC18 containing the synthetic IL-4 gene is inserted in *E. coli* K-12 strain JM101. After culturing, protein is extracted from the JM101 cells and dilutions of the extracts are tested for biological activity.

Example VIII

Construction and Expression of Human IL-4 Mutein Ile$^{52}$ in *E. coli*

Leu at position 52 (relative to the N-terminus of the native human IL-4) is changed to Ile to form human IL-4 mutein Ile$^{52}$. The pUC18 plasmid of Example VII containing the synthetic human IL-4 gene of FIG. 6A is digested with PstI and MluI and purified. The above purified pUC18 is mixed with the synthetic double stranded fragment illustrated below and ligated. The altered part of the base sequence is boxed. The resulting pUC18 is transfected into *E. coli* K-12 strain JM101, or the like, and expressed.

```
     GA  GCT  GCT  ACC  GTT |ATC| CGT
ACG  TCT  CGA  CGA  TGG  CAA |TAG| GCA

CAG  TTC  TAC  TCT  CAC  CAC  GAA  AAA
GTC  AAG  ATG  AGA  GTG  GTG  CTT  TTT

GAC  A
CTG  TGC  GC
```

PstI/MluI Replacement Fragment For Generating Human IL-4 Mutein Ile$^{52}$

After culturing, protein is extracted from the JM101 cells using standard techniques, and dilutions of the extracts are tested for biological activity.

Example IX

Construction and Expression of Human IL-4 Mutein (Ile$^{52}$, Asp$^{111}$)

The modified pUC18 plasmid of Example VIII (containing the Ile$^{52}$ coding sequence) is digested with SalI and XhoI, and the large fragment is isolated. The isolated fragment is mixed with the synthetic double stranded fragment illustrated below in a standard ligation solution. The altered part of the sequence is boxed. The resulting plasmid is transfected into *E. coli* K-12 strain JM101, or the like, and expressed.

```
TCG  ACT  CTG  GAA |GAC| TTC  C
     GA   GAC  CTT |CTG| AAG  GAG  CT
```

SalI/XhoI Replacement Fragment

After culturing, protein is extracted from the JM101 cells using standard techniques, and dilutions of the extracts are tested for biological activity.

Example X
Sequence of Human IL-4 Purified from Transfection Supernatants

Human IL-4 was purified from culture supernatants of cells transiently transfected with vectors containing human IL-4 cDNA. The sequence of the secreted native human IL-4 was determined from the purified material.

A. Biological Assay for Purification

TCGF activity was used to assay human IL-4 during the separation procedures. The assay was substantially the same as that described in Example II. Briefly, blood from a healthy donor was drawn into a heparinized tube and layered onto Ficoll-Hypaque; e.g., 5 ml of blood per 3 ml Ficoll-Hypaque in a 15 ml centrifuge tube. After centrifugation at 3000×g for 20 minutes, cells at the interface were aspirated and diluted in a growth medium consisting of RPMI 1640 containing 10% fetal calf serum, 50 micromolar 2-mercaptoethanol, 20 microgram/ml phytohemagglutinin (PHA), and recombinant human IL-2. After 5–10 days of incubation at 37° C., the PHA-stimulated peripheral blood lymphocytes (PBLs) were washed and used in 2 day calorimetric assays, Mossmann, *J. Immunol. Methods*, Vol. 65, pgs. 55–63 (1983). Serial two fold dilutions of the IL-4 standard (supernatants from either pcD-125 or pEBT-178 transfected COS 7 cells) or the fraction to be tested were performed in 96 well trays utilizing the growth medium described above to yield a final volume of 50 microliters/well. 50 microliters of the PHA stimulated PBLs at about 4–8×10$^6$ cells/ml were added to each well and the trays were incubated at 37° C. for 2 days. Cell growth was then measured according to Mosmann (cited above).

Units of human IL-4 TCGF activity are defined with respect to supernatants of either pcD-125 transfected COS 7 cells (Example II) or pEBV-178 transfected COS 7 cells (Example III).

For purification, units are based on the activity of pcD-125 transfection supernatants, which are produced as follows. About 1×10$^6$ COS-7 cells are seeded onto 100 mm tissue culture plates containing Dulbecco's Modified Eagle's medium (DME), 10% fetal calf serum, and 4 mM L-glutamine. About 24 hours after seeding, the medium is aspirated from the plates and the cells are washed twice with serum free buffered (50 mM Tris) DME. To each plate is added 4 ml serum free buffered DME (with 4 mM L-glutamine), 80 microliters DEAE-dextran, and 5 micrograms of pcD-125 DNA. The cells are incubated in this mixture for 4 hours at 30° C., after which the mixture is aspirated off and the cells are washed once with serum free buffered DME. After washing, 5 ml of DME with 4 mM L-glutamine, 100 micromolar Chloroquine, and 2% fetal calf serum is added to each plate, the cells are incubated for 3 hours, and then twice washed with serum free buffered DME. Next, 5 ml DME with 4 mM L-glutamine and 4% fetal calf serum is added and the cells are incubated at 37° C. for 24 hours. Afterwards the cells are washed 1–3 times with DME or PBS, 5 ml serum free DME (with 4 mM L-glutamine) is added, and the cells are incubated at 37° C. until culture supernatants are harvested 5 days later.

One unit, as used herein, is the amount of factor which in one well (0.1 ml) stimulates 50% maximal proliferation of 2×10$^4$ PHA stimulated PBLs over a 48 hour period.

B. Purification

Purification was accomplished by a sequential application of cation exchange chromatography, gel filtration and reverse-phase high pressure liquid chromatography. All operations were performed at 4° C.

After removing the COS 7 cells by centrifugation, the supernatant was concentrated about 10 fold by ultrafiltration and stored at −80° C. until further processed. IL-4 titers were determined by assaying for the ability of the protein to stimulate proliferation of phytohemagglutinin-induced human peripheral blood lymphocytes, i.e. by TCGF activity using the standard assay described above.

Concentrated COS 7 supernatant, having TCGF activity of about 10$^4$–10$^6$ units/ml and a protein content of about 15–20 mg/ml, is dialyzed against 2 changes of 50 mM sodium HEPES, pH 7.0 over a 24 hour period (each change being approximately 10–15 times the volume of one concentrate). The dialysate was applied to a column (1×2.5 cm) of S-Sepharose (flow rate: 0.2 ml/min) pre-equilibrated with 50 mM sodium HEPES, pH 7.0. The column were washed with 15 column volumes of equilibrating buffer followed by elution with 20 column volumes of a linear sodium chloride gradient extending from 0 to 0.5M sodium chloride in 50 mM sodium HEPES, pH 7.0. The gradient was terminated with an isocratic elution consisting of 5 column volumes of 50 mM sodium HEPES, 0.5M NaCl, pH 7.0. 1.5 ml and 1.8 ml fractions were collected from respective batches. IL-4 titers were found for both chromatographies to elute between 300 mM and 500 mM sodium chloride.

The fraccontaining the S-Sepharose columns containing IL-4 titers were combined for total separate volumes of 9.0 and 10.8 ml. Both volumes were concentrated to 1.9 ml by ultrafiltration using an Amicon YM5 membrane (molecular weight cut-off: 5000). The recovery of protein from this step was about 80%. The concentrated IL-4 solution was applied to a Sephadex G-100 column (1.1×58 cm) pre-equilibrated in 50 mM HEPES, 0.4M NaCl, pH 7.0 and the column was eluted with the same buffer at 0.15 ml/min. A total of 50 fractions (1.0 ml/fraction) was collected and analyzed for IL-4 titers. A peak in biological activity was observed at an apparent molecular weight of 22,000 daltons. The Sephadex G-100 was calibrated for apparent molecular determination with bovine serum albumin (65,000 daltons), carbonic anhydrase (30,000 daltons) and cytochrome C (11,700 daltons).

Figure 10:
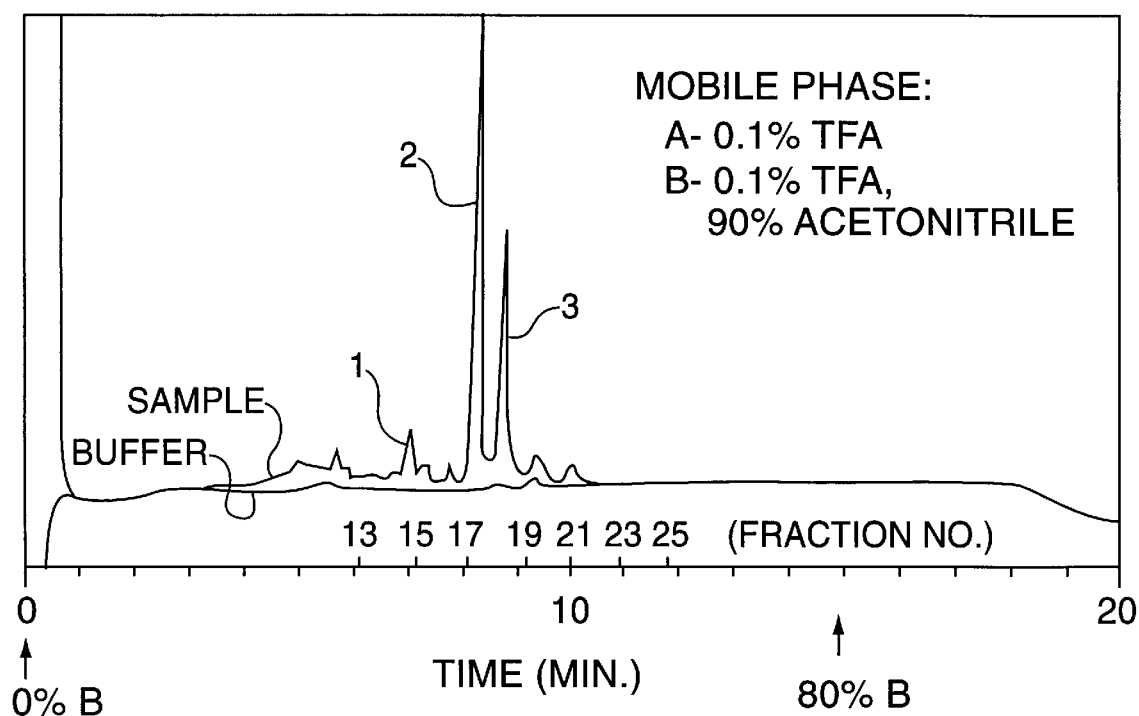
FIG. 10 illustrates the 215 nm absorption profile in the final human IL-4 purification step, which consisted of reversed-phase HPLC on a C-4 column.

A fraction from the Sephadex G-100 column containing IL-4 activity was concentrated 3–4 fold in vacuo and was injected onto a Vydac C-4 guard column (4.6×20 mm). A linear gradient of 0 to 72% (v/v) acetonitrile in 0.1% (v/v) trifluoroacetic acid (TFA) was produced in 15 minutes at a column temperature of 35° and a flow rate of 1.0 ml/min. Three peaks resulted that were detected at 214 nm with retention times of 7, 8.2 and 8.7 min. (peaks 1, 2, and 3 of FIG. 10, respectively). A 40 microliter aliquot of peak 2 (8.2 min. elution time) was lyophilized and redissolved in minimal essential medium containing 10% fetal calf serum. This solution showed a positive TCGF response. A 300 microliter aliquot of peak 2 was evaporated to dryness and redissolved in 200 ul of 0.1% (w/v) sodium dodecyl sulfate (SDS). A 2 ul aliquot was diluted in 200 ul of 1% (v/v) TFA and rechromatographed. The HPLC of this sample demonstrated a single peak at 215 nm. Peak 2 material indicated an activity of about 7×10$^8$ units/mg.

C. Amino Acid Sequence Analysis

Amino Acid sequence determination was performed by automated gas-phase Edman degradation (Hewick, R. M., Hunkapillar, M. W., Hood, L. E. and Dryer, W. J. (1981) J. Biol. Chem. 256: 7990.) employing an Applied Biosystems microsequenator. A 90 microliter aliquot of the peak 2 HPLC fraction, dissolved in 0.1% SDS as described above was applied to the glass fiber filter cartridge in the presence of Polybrene. Amino acid sequence information was obtained up to the 35th residue. The N-terminal sequence was determined as follows His—Lys—_—Asp—Ile—Thr—Leu—Gln—Glu—
    Ile—Ile—Lys—Thr—Leu—Asn—Ser—Leu—Thr—
    Glu—Gln—Lys—Thr—Leu—_—Thr—Glu—Leu—
    _—Val—Thr—Asp—Ile—Phe—Ala—Ala wherein the blanks indicate the lack of an identifiable amino acid.

Blanks in the the amino-terminus at positions 3 and 23 were consistent with the presence of cysteine, which can not be detected in this system. The blank at position 28, corresponding to a threonine in the cDNA-predicted sequence, may have been due either to the variability of phenylthiohydantoin-threonine detection or to the presence of O-linked glycosylation or esterification.

A 100 microliter aliquot of the HPLC fraction on which the amino-terminal sequence was performed was evaporated to dryness and redissolved in 70% formic acid. A 50-fold molar excess of cyanogen bromide was added and the solution was allowed to stand at room temperature for 2.5 hours. The cleaved protein was sequenced on the Applied Biosystems gas-phase sequenator, as described above. Two sequences were identifiable:

(1) Arg-Glu-Lys-Tyr-Ser-Lys
(2) His-Lys-_-Asp-Ile-Thr

Sequence (1) is identical to the sequence predicted from the cDNA to have been released following cyanogen bromide cleavage of the methionine residue at position 120. The last 2 residues of the C-terminus may have been present but may not have been detectable due to insufficient sample. Sequence (2) is identical to the amino-terminal sequence obtained for the native IL-4 protein, as described above. The relative amounts of amino-terminal and carboxyl-terminal phenylthiohydantoin-amino acids released suggested equimolar amounts of both sequences in the sample. This result supports the conclusion that the protein sample that was sequenced contained predominantly a single polypeptide chain with amino and carboxyl termini predicted from the cDNA sequence of human IL-4.

Example XI
Construction and Expression of Human IL-4 Mutein (Ile$^{52}$, $\Delta^{71}$, IS$^{94}$(Ala))

The modified pUC18 plasmid of Example VIII (containing the Ile$^{52}$ coding sequence) is digested with MluI and BclI, and the large fragment is isolated. The isolated fragment is mixed with the synthetic double stranded fragment illustrated below in a standard ligation solution. The resulting plasmid is transfected into E. coli K-12 JM101, or the like, and propagated.

```
CG    CGT TGT CTC GGC GCC ACT
      A ACA GAG CCG CGG TGA

GCG   CAG TTC CAC CGT CAC AAA GAG CT
CGC   GTC AAG GTG GCA GTG TTT GTC GAC TAG
 ↑
Deletion
```

MluI/BclI Replacement Fragment

The modified plasmid is isolated and digested with XbaI and NaeI, and the large fragment is isolated. The isolated fragment is mixed with the synthetic double stranded fragment illustrated below in a standard ligation solution. The added codon is boxed. The resulting plasmid is transfected into E. coli K-12 strain JM101, or the like, and expressed.

```
CTA   GAC  CGT  AAC  CTG  TGG  GGC
      TG   GCA  TTG  GAC  ACC  CCG

CTG   GCC  GCC
GAC   CGG  CGG
```

XbaI/NaeI Replacement Fragment

After culturing, protein is extracted from the JM101 cells using standard techniques, and dilutions of the extracts are tested for biological activity.

Example XII
Induction of DR Antigens on Cells from a Patient Suffering from Bare Lymphocyte Syndrome Bare lymphocyte syndrome is characterized by the lack of expression of class I and/or class II BLA antigens on cell surfaces, and is frequently associated with severe immunodeficiency, e.g. Touraine, Lancet, pgs. 319–321 (Feb. 7, 1981); Touraine and Bethel, Human Immunology, Vol. 2, pgs. 147–153 (1981); and Sullivan et al., J. Clin. Invest., Vol. 76, pgs. 75–79 (1985). It was discovered that human IL-4 was capable of inducing the expression of the class II DR antigen on the surfaces of cells derived from a patient suffering from bare lymphocyte syndrome.

Figure 9:
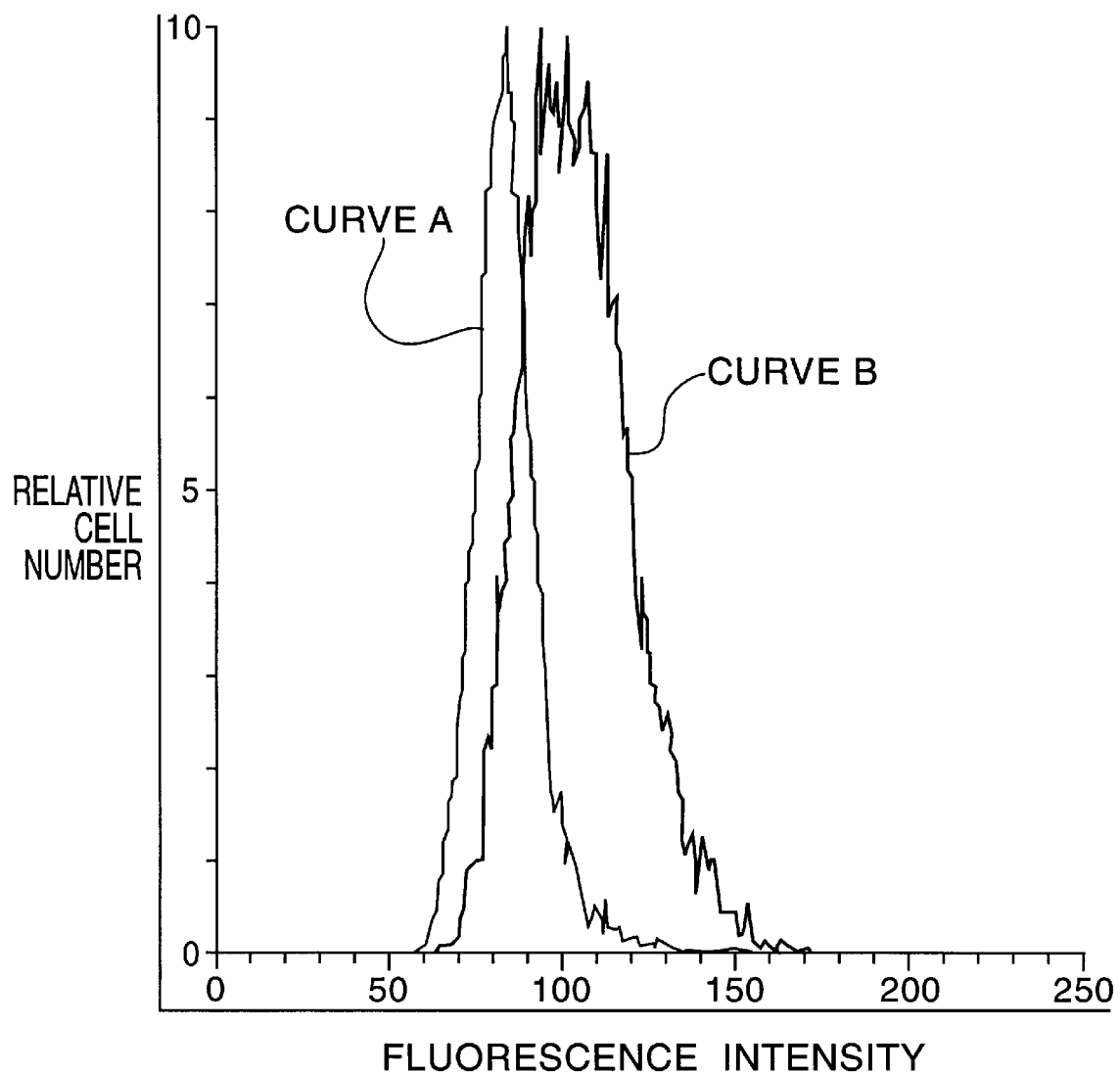
FIG. 9 illustrates histograms of cell frequency versus fluorescence intensity for populations of cells derived from a patient with bare lymphocyte syndrome. The cells were stained with fluorescently labeled anti-DR monoclonal antibodies.

Peripheral blood lymphocytes (PBLs) were obtained from a patient suffering from non-expression of HLA class II antigens. B cells were purified from the PBLs essentially as described above, and a B cell line (designated UD31) was established by transformation with Epstein-Barr virus (EBV). The EBV-transformed cells were cultured for 48 hours in Yssel's defined medium (described above) with 2% fetal calf serum and a 5% (v/v) concentration of supernatant from pcD-125 transfected COS 7 cells. The cells were harvested, fixed, stained with fluorescently labeled anti-DR monoclonal antibody (e.g. Becton Dickinson, L243), and analyzed flow cytometrically. FIG. 9 illustrates histograms of cell frequency versus fluorescence intensity for a control population of the EBV-transformed cells harvested prior to IL-4 treatment (Curve A), and for the population of EBV-transformed cells after IL-4 treatment (Curve B).

The descriptions of the foregoing embodiments of the invention have been presented for purpose of illustration and description. They are not intended to be exhaustive or to limit the invention to the precise forms disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

Applicants have deposited cDNA clones pcD-2A-E3, pcD-46 (pcD-2F1-13), pcD-125, and yeast vector pMF-alpha8 with the American Type Culture Collection, Rockville, Md., U.S.A. (ATCC), under accession numbers 53330, 53337, 67029, and 40140, respectively. These deposits were made under conditions as provided under ATCC's agreement for Culture Deposit for Patent Purposes, which assures that these deposits will be made available to the US Commissioner of Patents and Trademarks pursuant to 35 USC 122 and 37 CFR 1.14, and will be made available to the public upon issue of a U.S. patent, which requires this deposit to be maintained. Availability of the deposited strains is not to be construed as a license to practice the invention in contravention of the rights granted under the authority of any government in accordance with its patent laws.

We claim:

1. A fused polypeptide comprising an antigenic polypeptide comprising a plurality of non-overlapping segments of at least 6 amino acid residues each found in the amino acid sequence of FIG. 1B or a conservative substituent variant thereof, said antigenic polypeptide being fused with a heterologous protein.

2. A fused polypeptide comprising an antigenic polypeptide comprising a sequence found in a human interleukin-4 selected from the group consisting of:

a) Met-Gly-Leu-Thr-Ser-Gln-Leu-Leu-Pro-Pro-Leu-Phe-Phe-Leu-Leu-Ala-Cys-Ala-Gly-Asn-Phe-Val-His-Gly;

b) His-Lys-Cys-Asp-Ile-Thr-Leu-Gln-Glu-Ile-Ile-Lys-Thr-Leu-Asn-Ser-Leu-Thr-Glu-Gln-Lys-Thr-Leu-Cys-Thr-Glu-Leu-Thr-Val-Thr-Asp-Ile-Phe-Ala-Ala;

c) Ser-Lys-Asn-Thr-Thr-Glu-Lys-Glu-Thr-Phe-Cys-Arg-Ala-Ala-Thr-Val-Leu-Arg-Gln-Phe-Tyr-Ser-His-His-Glu-Lys-Asp-Thr-Arg-Cys-Leu;

d) Gly-Ala-Thr-Ala-Gln-Gln-Phe-His-Arg-His-Lys-Gln-Leu-Ile-Arg-Phe-Leu-Lys-Arg-Leu-Asp-Arg-Asn-Leu-Trp-Gly-Leu-Ala-Gly-Leu-Asn-Ser-Cys-Pro-Val-Lys-Glu-Ala; or e) Asn-Gln-Ser-Thr-Leu-Glu-Asn-Phe-Leu-Glu-Arg-Leu-Lys-Thr-Ile-Met-Arg-Glu-Lys-Tyr-Ser, said antigenic polypeptide being fused with a heterologous polypeptide.

* * * * *